(12) United States Patent
Osterhout et al.

(10) Patent No.: US 9,139,853 B2
(45) Date of Patent: Sep. 22, 2015

(54) ORGANISMS FOR THE PRODUCTION OF CYCLOHEXANONE

(71) Applicant: Genomatica, Inc., San Diego, CA (US)

(72) Inventors: Robin E. Osterhout, San Diego, CA (US); Anthony P. Burgard, Bellefonte, PA (US); Mark J. Burk, San Diego, CA (US); Priti Pharkya, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 0 days.

(21) Appl. No.: 14/172,079

(22) Filed: Feb. 4, 2014

(65) Prior Publication Data

US 2014/0356919 A1 Dec. 4, 2014

Related U.S. Application Data

(62) Division of application No. 12/780,802, filed on May 14, 2010, now Pat. No. 8,663,957.

(60) Provisional application No. 61/178,791, filed on May 15, 2009.

(51) Int. Cl.

| | |
|---|---|
| *C12N 9/16* | (2006.01) |
| *C12N 9/88* | (2006.01) |
| *C12N 1/20* | (2006.01) |
| *C12P 7/26* | (2006.01) |
| *C12N 9/00* | (2006.01) |
| *C12N 15/52* | (2006.01) |
| *C12N 15/70* | (2006.01) |

(52) U.S. Cl.
CPC ... *C12P 7/26* (2013.01); *C12N 9/16* (2013.01); *C12N 9/88* (2013.01); *C12N 9/93* (2013.01); *C12N 15/52* (2013.01); *C12N 15/70* (2013.01)

(58) Field of Classification Search
CPC . A61K 47/482; A61K 47/48892; C12N 9/16; C12N 9/88; C12N 9/93
USPC .......................................................... 435/41
See application file for complete search history.

(56) References Cited

U.S. PATENT DOCUMENTS 8,663,957 B2 * 3/2014 Osterhout et al. ............ 435/148

* cited by examiner

*Primary Examiner* — Tekchand Saidha
(74) *Attorney, Agent, or Firm* — Jones Day

(57) ABSTRACT

A non-naturally occurring microbial organism has cyclohexanone pathways that include at least one exogenous nucleic acid encoding a cyclohexanone pathway enzyme. A pathway includes a 2-ketocyclohexane-1-carboxyl-CoA hydrolase (acting on C—C bond), a 2-ketocyclohexane-1-carboxylate decarboxylase and an enzyme selected from a 2-ketocyclohexane-1-carboxyl-CoA hydrolase (acting on thioester), a 2-ketocyclohexane-1-carboxyl-CoA transferase, and a 2-ketocyclohexane-1-carboxyl-CoA synthetase. A pathway includes an enzyme selected from a 6-ketocyclohex-1-ene-1-carboxyl-CoA hydrolase (acting on C—C bond), a 6-ketocyclohex-1-ene-1-carboxyl-CoA synthetase, a 6-ketocyclohex-1-ene-1-carboxyl-CoA hydrolase (acting on thioester), a 6-ketocyclohex-1-ene-1-carboxyl-CoA transferase, a 6-ketocyclohex-1-ene-1-carboxyl-CoA reductase, a 6-ketocyclohex-1-ene-1-carboxylate decarboxylase, a 6-ketocyclohex-1-ene-1-carboxylate reductase, a 2-ketocyclohexane-1-carboxyl-CoA synthetase, a 2-ketocyclohexane-1-carboxyl-CoA transferase, a 2-ketocyclohexane-1-carboxyl-CoA hydrolase (acting on thioester), a 2-ketocyclohexane-1-carboxylate decarboxylase, and a cyclohexanone dehydrogenase. A pathway includes an adipate semialdehyde dehydratase, a cyclohexane-1,2-diol dehydrogenase, and a cyclohexane-1,2-diol dehydratase. A pathway includes a 3-oxopimelate decarboxylase, a 4-acetylbutyrate dehydratase, a 3-hydroxycyclohexanone dehydrogenase, a 2-cyclohexenone hydratase, a cyclohexanone dehydrogenase and an enzyme selected from a 3-oxopimeloyl-CoA synthetase, a 3-oxopimeloyl-CoA hydrolase (acting on thioester), and a 3-oxopimeloyl-coA transferase. Each these pathways can include a PEP carboxykinase. A method for producing cyclohexanone includes culturing these non-naturally occurring microbial organisms.

6 Claims, 7 Drawing Sheets

ORGANISMS FOR THE PRODUCTION OF CYCLOHEXANONE

This application is a divisional of U.S. Ser. No. 12/780,802 filed May 14, 2010, now U.S. Pat. No. 8,663,957, which claims the benefit of priority of U.S. Provisional Application No. 61/178,791, filed May 15, 2009, the entire contents of each of which are incorporated herein by reference.

BACKGROUND OF THE INVENTION

The present invention relates generally to biosynthetic processes and organisms capable of producing organic compounds. More specifically, the invention relates to non-naturally occurring organisms that can produce the commodity chemical cyclohexanone.

Cyclohexanone is an important chemical precursor of Nylon 6 and Nylon 66. Oxidation of cyclohexanone with nitric acid results in the formation of adipic acid, a key building block for Nylon 66. Cyclohexanone oximation and subsequent Beckmann rearrangement forms the basis for the preparation of caprolactam, a precursor to Nylon 6.

The cost of cyclohexanone is mainly subject to the raw material cost of pure benzene. Cyclohexanone is chemically synthesized by oxidation of cyclohexane using a cobalt catalyst, resulting in a mixture of cyclohexanone and cyclohexanol called "KA oil". Alternatively, cyclohexanone can be produced by partial hydrogenation of phenol.

Thus, there exists a need to develop microorganisms and methods of their use to produce cyclohexanone from inexpensive and renewable feedstocks. The present invention satisfies this need and provides related advantages as well.

SUMMARY OF THE INVENTION

In some aspects, the present invention provides a non-naturally occurring microbial organism that includes a microbial organism having a cyclohexanone pathway having at least one exogenous nucleic acid encoding a cyclohexanone pathway enzyme expressed in a sufficient amount to produce cyclohexanone. In some embodiments, the cyclohexanone pathway includes a PEP carboxykinase, a 2-ketocyclohexane-1-carboxyl-CoA hydrolase (acting on C—C bond), a 2-ketocyclohexane-1-carboxylate decarboxylase and an enzyme selected from the group consisting of a 2-ketocyclohexane-1-carboxyl-CoA hydrolase (acting on thioester), a 2-ketocyclohexane-1-carboxyl-CoA transferase, and a 2-ketocyclohexane-1-carboxyl-CoA synthetase.

In other embodiments, the cyclohexanone pathway includes an enzyme selected from a PEP carboxykinase, a 6-ketocyclohex-1-ene-1-carboxyl-CoA hydrolase (acting on C—C bond), a 6-ketocyclohex-1-ene-1-carboxyl-CoA synthetase, a 6-ketocyclohex-1-ene-1-carboxyl-CoA hydrolase (acting on thioester), a 6-ketocyclohex-1-ene-1-carboxyl-CoA transferase, a 6-ketocyclohex-1-ene-1-carboxyl-CoA reductase, a 6-ketocyclohex-1-ene-1-carboxylate decarboxylase, a 6-ketocyclohex-1-ene-1-carboxylate reductase, a 2-ketocyclohexane-1-carboxyl-CoA synthetase, a 2-ketocyclohexane-1-carboxyl-CoA transferase, a 2-ketocyclohexane-1-carboxyl-CoA hydrolase (acting on thioester), a 2-ketocyclohexane-1-carboxylate decarboxylase, and a cyclohexanone dehydrogenase.

In further embodiments, the cyclohexanone pathway includes a PEP carboxykinase, an adipate semialdehyde dehydratase, a cyclohexane-1,2-diol dehydrogenase, and a cyclohexane-1,2-diol dehydratase.

In yet further embodiments, the cyclohexanone pathway includes a PEP carboxykinase, a 3-oxopimelate decarboxylase, a 4-acetylbutyrate dehydratase, a 3-hydroxycyclohexanone dehydrogenase, a 2-cyclohexenone hydratase, a cyclohexanone dehydrogenase and an enzyme selected from the group consisting of a 3-oxopimeloyl-CoA synthetase, a 3-oxopimeloyl-CoA hydrolase (acting on thioester), and a 3-oxopimeloyl-coA transferase.

In some aspects, the present invention provides a method for producing cyclohexanone, comprising culturing a non-naturally occurring microbial organism having a cyclohexanone pathway having at least one exogenous nucleic acid encoding a cyclohexanone pathway enzyme expressed in a sufficient amount to produce cyclohexanone, under conditions and for a sufficient period of time to produce cyclohexanone. In some embodiments, the cyclohexanone pathway includes a PEP carboxykinase, a 2-ketocyclohexane-1-carboxyl-CoA hydrolase (acting on C—C bond), a 2-ketocyclohexane-1-carboxylate decarboxylase and an enzyme selected from the group consisting of a 2-ketocyclohexane-1-carboxyl-CoA hydrolase (acting on thioester), a 2-ketocyclohexane-1-carboxyl-CoA transferase, and a 2-ketocyclohexane-1-carboxyl-CoA synthetase.

In other embodiments of the method a set of cyclohexanone pathway enzymes are selected from (a) PEP carboxykinase, 6-ketocyclohex-1-ene-1-carboxyl-CoA hydrolase (acting on C—C bond), 6-ketocyclohex-1-ene-1-carboxylate decarboxylase, cyclohexanone dehydrogenase, and an enzyme selected from 6-ketocyclohex-1-ene-1-carboxyl-CoA synthetase, 6-ketocyclohex-1-ene-1-carboxyl-CoA hydrolase (acting on thioester), and 6-ketocyclohex-1-ene-1-carboxyl-CoA transferase; (b) PEP carboxykinase, 6-ketocyclohex-1-ene-1-carboxyl-CoA hydrolase (acting on C—C bond), 6-ketocyclohex-1-ene-1-carboxylate reductase, 2-ketocyclohexane-1-carboxylate decarboxylase, and an enzyme selected from 6-ketocyclohex-1-ene-1-carboxyl-CoA synthetase, 6-ketocyclohex-1-ene-1-carboxyl-CoA hydrolase (acting on thioester), and 6-ketocyclohex-1-ene-1-carboxyl-CoA transferase; and (c) PEP carboxykinase, 6-ketocyclohex-1-ene-1-carboxyl-CoA hydrolase (acting on C—C), 6-ketocyclohex-1-ene-1-carboxyl-CoA reductase, 2-ketocyclohexane-1-carboxylate decarboxylase, and an enzyme selected from 2-ketocyclohexane-1-carboxyl-CoA synthetase, 2-ketocyclohexane-1-carboxyl-CoA transferase, 2-ketocyclohexane-1-carboxyl-CoA hydrolase (acting on thioester).

In still further embodiments of the method, the cyclohexanone pathway includes a PEP carboxykinase, an adipate semialdehyde dehydratase, a cyclohexane-1,2-diol dehydrogenase, and a cyclohexane-1,2-diol dehydratase.

In yet further embodiments of the method, the cyclohexanone pathway includes a PEP carboxykinase, a 3-oxopimelate decarboxylase, a 4-acetylbutyrate dehydratase, a 3-hydroxycyclohexanone dehydrogenase, a 2-cyclohexenone hydratase, a cyclohexanone dehydrogenase and an enzyme selected from a 3-oxopimeloyl-CoA synthetase, a 3-oxopimeloyl-CoA hydrolase (acting on thioester), and a 3-oxopimeloyl-coA transferase.

DETAILED DESCRIPTION OF THE INVENTION

Figure 1:
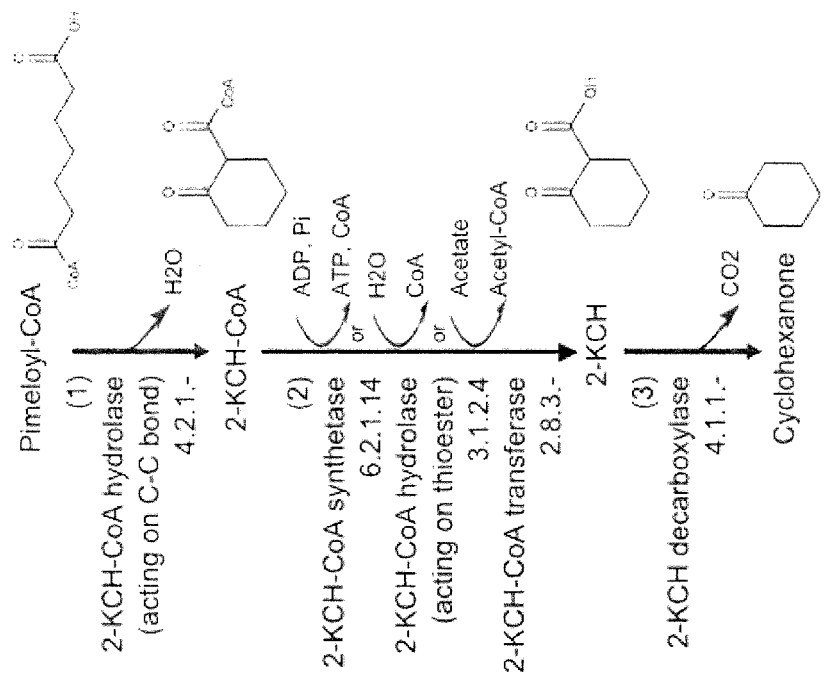
FIG. 1 shows the transformation of pimeloyl-CoA to cyclohexanone. Abbreviations are: 2-KCH-CoA=2-ketocyclohexane-1-carboxyl-CoA, 2-KCH=2-ketocyclohexane-1-carboxylate.

This invention is directed, in part, to non-naturally occurring microorganisms that express genes encoding enzymes that catalyze cyclohexanone production via fermentation from a renewable sugar feedstock. The theoretical yield of cyclohexanone starting from glucose as a raw material is 0.75 mol/mol glucose (0.409 g/g) as shown below in Equation 1:

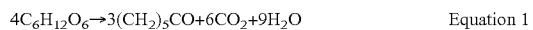

$$4C_6H_{12}O_6 \rightarrow 3(CH_2)_5CO + 6CO_2 + 9H_2O \quad \text{Equation 1}$$

In accordance with some embodiments, a cyclohexanone biosynthetic pathway involves a pimeloyl-CoA intermediate. This pathway uses channeling of flux towards the synthesis of pimeloyl-CoA, an intermediate of biotin biosynthetic pathways in bacteria, archaea and some fungi (168). Although pimeloyl-CoA is a widespread metabolite, the pathways involved in producing this intermediate have not been fully elucidated. In some embodiments, the present invention provides energetically favorable routes for synthesizing pimeloyl-CoA. The routes disclosed herein for the synthesis of pimeloyl-CoA can be applied to produce cyclohexanone from central metabolic precursors. In additional embodiments, a route for synthesizing cyclohexanone via enzymes in a benzoyl-CoA degradation pathway is disclosed. This pathway does not proceed through pimeloyl-CoA as an intermediate, but does pass through a potential pimeloyl-CoA precursor, 3-hydroxypimeloyl-CoA. In a further embodiment, the present invention provides a pathway from adipate semialdehyde to cyclohexanone. This pathway relates to Applicants previous disclosure related to routes to adipate as disclosed in U.S. patent application Ser. No. 12/413,355, not yet published. In still further embodiments, a pathway to cyclohexanone from 3-oxopimeloyl-CoA via the intermediate 4-acetylbutyrate is described herein.

For each pathway, enzymes are identified with their corresponding GenBank identifier. The sequences for enzymes listed in this report can be used to identify homologue proteins in GenBank or other databases through sequence similarity searches (e.g. BLASTp). The resulting homologue proteins and their corresponding gene sequences provide additional DNA sequences for transformation into *Escherichia coli* or other microorganisms.

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes or proteins within a cyclohexanone biosynthetic pathway.

A metabolic modification refers to a biochemical reaction that is altered from its naturally occurring state. Therefore, non-naturally occurring microorganisms can have genetic modifications to nucleic acids encoding metabolic polypeptides or, functional fragments thereof. Exemplary metabolic modifications are disclosed herein.

As used herein, the term "isolated" when used in reference to a microbial organism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsisted in non-naturally occurring environments. Specific examples of isolated microbial organisms include partially pure microbes, substantially pure microbes and microbes cultured in a medium that is non-naturally occurring.

As used herein, the terms "microbial," "microbial organism" or "microorganism" is intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, the term "CoA" or "coenzyme A" is intended to mean an organic cofactor or prosthetic group (nonprotein portion of an enzyme) whose presence is required for the activity of many enzymes (the apoenzyme) to form an active enzyme system. Coenzyme A functions in certain condensing enzymes, acts in acetyl or other acyl group transfer and in fatty acid synthesis and oxidation, pyruvate oxidation and in other acetylation.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

"Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

It is understood that when more than one exogenous nucleic acid is included in a microbial organism that the more than one exogenous nucleic acids refers to the referenced encoding nucleic acid or biosynthetic activity, as discussed above. It is further understood, as disclosed herein, that such more than one exogenous nucleic acids can be introduced into the host microbial organism on separate nucleic acid molecules, on polycistronic nucleic acid molecules, or a combination thereof, and still be considered as more than one exogenous nucleic acid. For example, as disclosed herein a microbial organism can be engineered to express two or more exogenous nucleic acids encoding a desired pathway enzyme or protein. In the case where two exogenous nucleic acids encoding a desired activity are introduced into a host microbial organism, it is understood that the two exogenous nucleic acids can be introduced as a single nucleic acid, for example, on a single plasmid, on separate plasmids, can be integrated into the host chromosome at a single site or multiple sites, and still be considered as two exogenous nucleic acids. Similarly, it is understood that more than two exogenous nucleic acids can be introduced into a host organism in any desired combination, for example, on a single plasmid, on separate plasmids, can be integrated into the host chromosome at a single site or multiple sites, and still be considered as two or more exogenous nucleic acids, for example three exogenous nucleic acids. Thus, the number of referenced exogenous nucleic acids or biosynthetic activities refers to the number of encoding nucleic acids or the number of biosynthetic activities, not the number of separate nucleic acids introduced into the host organism.

The non-naturally occurring microbal organisms of the invention can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications be greater than 50 generations, including indefinitely.

Those skilled in the art will understand that the genetic alterations, including metabolic modifications exemplified herein, are described with reference to a suitable host organism such as E. coli and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the E. coli metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art will understand that the orthologous gene harboring the metabolic activity to be introduced or disrupted is to be chosen for construction of the non-naturally occurring microorganism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of mycoplasma 5'-3' exonuclease and Drosophila DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Therefore, in identifying and constructing the non-naturally occurring microbial organisms of the invention having cyclohexanone biosynthetic capability, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionally related genes.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% can represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

In some embodiments, the present invention provides a non-naturally occurring microbial organism that includes a microbial organism having a cyclohexanone pathway having at least one exogenous nucleic acid encoding a cyclohexanone pathway enzyme expressed in a sufficient amount to produce cyclohexanone. The cyclohexanone pathway includes a PEP carboxykinase, a 2-ketocyclohexane-1-carboxyl-CoA hydrolase (acting on C—C bond), a 2-ketocyclohexane-1-carboxylate decarboxylase and an enzyme selected from a 2-ketocyclohexane-1-carboxyl-CoA hydrolase (acting on thioester), a 2-ketocyclohexane-1-carboxyl-CoA transferase, and a 2-ketocyclohexane-1-carboxyl-CoA synthetase. Such a microbial organism can also include two exogenous nucleic acids, each encoding a cyclohexanone pathway enzyme. In other embodiments such an organism can include three exogenous nucleic acids each encoding a cyclohexanone pathway enzyme. In yet further embodiments such an organism can include four exogenous nucleic acids, each encoding a cyclohexanone pathway enzyme. Any exogenous nucleic acid can be provided as a heterologous nucleic acid. Such anon-naturally occurring microbial organism can be provided in (and cultured in) a substantially anaerobic culture medium.

Organisms having a cyclohexanone pathway for converting pimeloyl-CoA to cyclohexanone can include a PEP carboxykinase. The PEP carboxykinase can be encoded by one or more genes selected from PCK1, pck, and pckA. Organisms having a cyclohexanone pathway for converting pimeloyl-CoA to cyclohexanone can include a 2-ketocyclohexane-1-carboxyl-CoA hydrolase (acting on C—C bond). Such an enzyme is run in the reverse direction to cyclize pimeloyl-CoA as shown in FIG. 1. The 2-ketocyclohexane-1-carboxyl-CoA hydrolase (acting on C—C bond) can be encoded by one or more genes selected from badI, syn__01653, syn__01654, syn__02400, syn__03076, syn__01309, and menB. Organisms having a cyclohexanone pathway for converting pimeloyl-CoA to cyclohexanone can include a 2-ketocyclohexane-1-carboxylate decarboxylase. The 2-ketocyclohexane-1-carboxylate decarboxylase can be encoded by one or more genes selected from adc, cbei__3835, CLL_A2135, and RBAM__030030. Organisms having a cyclohexanone pathway for converting pimeloyl-CoA to cyclohexanone can also include a 2-ketocyclohexane-1-carboxyl-CoA hydrolase (acting on thioester). The 2-ketocyclohexane-1-carboxyl-CoA hydrolase (acting on thioester) can be encoded by one or more genes selected from acot12, gctA, gctB, and ACH1. Organisms having a cyclohexanone pathway for converting pimeloyl-CoA to cyclohexanone can also include a 2-ketocyclohexane-1-carboxyl-CoA transferase. The 2-ketocyclohexane-1-carboxyl-CoA transferase can be encoded by one or more genes selected from pcaI, pcaJ, catI, catJ, HPAG1__0676, HPAG__10677, ScoA, ScoB, OXCT1, OXCT2, ctfA, ctfB, atoA, and atoD. Organisms having a cyclohexanone pathway for converting pimeloyl-CoA to cyclohexanone can also include a 2-ketocyclohexane-1-carboxyl-CoA synthetase. The 2-ketocyclohexane-1-carboxyl-CoA synthetase can be encoded by one or more genes selected from AF1211, AF1983, scs, PAE3250, sucC, sucD, aliA, phl, phlB, paaF, and bioW.

Figure 2:
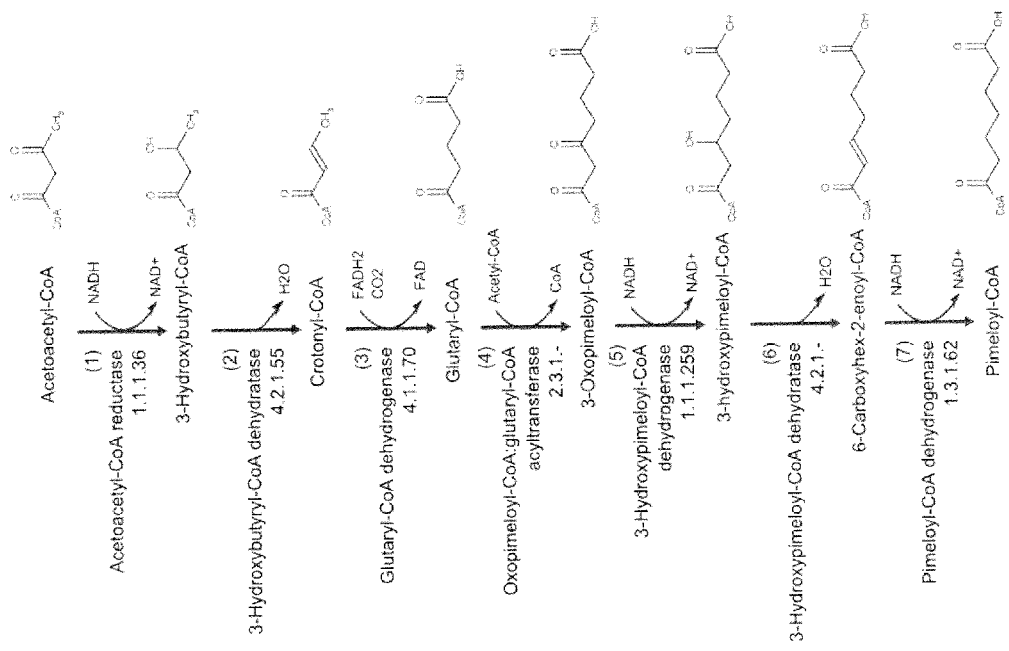
FIG. 2 shows the transformation of acetoacetyl-CoA to pimeloyl-CoA.

In some embodiments, the non-naturally occurring microbial organism has a native pimeloyl-CoA pathway, while in other embodiments a pimeloyl-CoA pathway can be provided by addition of further exogenous nucleic acids encoding a pimeloyl-CoA pathway enzyme for the production of pimeloyl-CoA from acetoacetyl-CoA, as shown in FIG. 2. Thus, a microbial organism can further include a pimeloyl-CoA pathway that includes at least one exogenous nucleic acid encoding a pimeloyl-CoA pathway enzyme expressed in a sufficient amount to produce pimeloyl-CoA. The pimeloyl-CoA pathway includes an acetoacetyl-CoA reductase, a 3-hydroxybutyryl-CoA dehydratase, a glutaryl-CoA dehydrogenase, a oxopimeloyl-CoA:glutaryl-CoA acyltransferase, a 3-hydroxypimeloyl-CoA dehydrogenase, a 3-hydroxypimeloyl-CoA dehydratase, and a pimeloyl-CoA dehydrogenase. Any number of enzymes can be provided exogenously to provide a non-naturally occurring microbial organism with a complete pimeloyl-CoA pathway for the production of pimeloyl-CoA. For example, the organism can include two, three, four, five, six, seven, that is up to all exogenous nucleic acids each encoding a pimeloyl-CoA pathway enzyme.

Organisms having a pimeloyl-CoA pathway for converting acetoacetyl-CoA to pimeloyl-CoA can include an acetoacetyl-CoA reductase. The acetoacetyl-CoA reductase can be encoded by one or more genes selected from Fox2, phaB, phbB, hbd, Msed_1423, Msed_0399, Msed_0389, Msed_1993, Hbd2, Hbd1 HSD17B10, pimF, facdB, syn_01310, and syn_01680.

Organisms having a pimeloyl-CoA pathway for converting acetoacetyl-CoA to pimeloyl-CoA can include a 3-hydroxybutyryl-CoA dehydratase. The 3-hydroxybutyryl-CoA dehydratase can be encoded by one or more genes selected from the group consisting of crt, crt1, pimF, syn_01309, syn_01653, syn_01654, syn_02400, syn_03076, ech, paaA, paaB, phaA, phaB, maoC, paaF, paaG, fadA, fadB, fadI, fadJ, and fadR.

Organisms having a pimeloyl-CoA pathway for converting acetoacetyl-CoA to pimeloyl-CoA can include a glutaryl-CoA dehydrogenase. The glutaryl-CoA dehydrogenase can be encoded by one or more genes selected from gcdH, gcdR, PP_0157, gcvA, gcd, gcdR, syn_00480, syn_01146, gcdA, gcdC, gcdD, gcdB, FN0200, FN0201, FN204, syn_00479, syn_00481, syn_01431, and syn_00480.

Organisms having a pimeloyl-CoA pathway for converting acetoacetyl-CoA to pimeloyl-CoA can include an oxopimeloyl-CoA:glutaryl-CoA acyltransferase. The oxopimeloyl-CoA:glutaryl-CoA acyltransferase can be encoded by one or more genes selected from bktB, pimB, syn_02642, phaA, h16_A1713, pcaF, h16_B1369, h16_A0170, h16_A0462, h16_A1528, h16_B0381, h16_B0662, h16_B0759, h16_B0668, h16_A1720, h16_A1887, phbA, Rmet_1362, Bphy_0975, atoB, thlA, thlB, ERG10, and catF.

Organisms having a pimeloyl-CoA pathway for converting acetoacetyl-CoA to pimeloyl-CoA can include a 3-hydroxypimeloyl-CoA dehydrogenase. The 3-hydroxypimeloyl-CoA dehydrogenase can be encoded by one or more genes selected from Fox2, phaB, phbB, hbd, Msed_1423, Msed_0399, Msed_0389, Msed_1993, Hbd2, Hbd1, HSD17B10, pimF, fadB, syn_01310, and syn_01680.

Organisms having a pimeloyl-CoA pathway for converting acetoacetyl-CoA to pimeloyl-CoA can include a 3-hydroxypimeloyl-CoA dehydratase. The 3-hydroxypimeloyl-CoA dehydratase is encoded by one or more genes selected from the group consisting of crt, era, pimF, syn_01309, syn_01653, syn_01654, syn_02400, syn_03076, ech, paaA, paaB, phaA, phaB, maoC, paaF, paaG, fadA, fadB, fadI, fadJ, and fadR.

Organisms having a pimeloyl-CoA pathway for converting acetoacetyl-CoA to pimeloyl-CoA can include a pimeloyl-CoA dehydrogenase. The pimeloyl-CoA dehydrogenase can be encoded by one or more genes selected from bcd, etfA, etfB, TER, TDE0597, syn_02587, syn_02586, syn_01146, syn_00480, syn_02128, syn_01699, syn_02637, syn_02636, pimC, pimD, acad1, and acad.

In some embodiments, the present invention provides a non-naturally occurring microbial organism that includes a microbial organism having a cyclohexanone pathway having at least one exogenous nucleic acid encoding a cyclohexanone pathway enzyme expressed in a sufficient amount to produce cyclohexanone. The cyclohexanone pathway includes an enzyme selected from a PEP carboxykinase, a 6-ketocyclohex-1-ene-1-carboxyl-CoA hydrolase (acting on C—C bond), a 6-ketocyclohex-1-ene-1-carboxyl-CoA synthetase, a 6-ketocyclohex-1-ene-1-carboxyl-CoA hydrolase (acting on thioester), a 6-ketocyclohex-1-ene-1-carboxyl-CoA transferase, a 6-ketocyclohex-1-ene-1-carboxyl-CoA reductase, a 6-ketocyclohex-1-ene-1-carboxylate decarboxylase, a 6-ketocyclohex-1-ene-1-carboxylate reductase, a 2-ketocyclohexane-1-carboxyl-CoA synthetase, a 2-ketocyclohexane-1-carboxyl-CoA transferase, a 2-ketocyclohexane-1-carboxyl-CoA hydrolase (acting on thioester), a 2-ketocyclohexane-1-carboxylate decarboxylase, and a cyclohexanone dehydrogenase. Combinations of the foregoing enzymes are capable of converting 3-hydroxypimeloyl-CoA to cyclohexanone, as exemplified in FIG. 3.

The non-naturally occurring microbial organism that can convert 3-hydroxypimeloyl-CoA to cyclohexanone can include any number of exogenous enzymes to complete a cyclohexanone pathway, including two, three, four, five, up to all the enzymes in the pathway. Any number of such exogenous nucleic acids can be a heterologous nucleic acid. Such a non-naturally occurring microbial organism can be provided in (and cultured in) a substantially anaerobic culture medium.

Exemplary sets of enzymes constituting a complete set of cyclohexanone pathway enzymes for converting 3-hydroxypimeloyl-Coa to cyclohexanone include, without limitation, (a) PEP carboxykinase, 6-ketocyclohex-1-ene-1-carboxyl-CoA hydrolase (acting on C—C bond), 6-ketocyclohex-1-ene-1-carboxylate decarboxylase, cyclohexanone dehydrogenase, and an enzyme selected from the group consisting of 6-ketocyclohex-1-ene-1-carboxyl-CoA synthetase, 6-ketocyclohex-1-ene-1-carboxyl-CoA hydrolase (acting on thioester), and 6-ketocyclohex-1-ene-1-carboxyl-CoA transferase; (b) PEP carboxykinase, 6-ketocyclohex-1-ene-1-carboxyl-CoA hydrolase (acting on C—C bond), 6-ketocyclohex-1-ene-1-carboxylate reductase, 2-ketocyclohexane-1-carboxylate decarboxylase, and an enzyme selected from the group consisting of 6-ketocyclohex-1-ene-1-carboxyl-CoA synthetase, 6-ketocyclohex-1-ene-1-carboxyl-CoA hydrolase (acting on thioester), and 6-ketocyclohex-1-ene-1-carboxyl-CoA transferase; and (c) PEP carboxykinase, 6-ketocyclohex-1-ene-1-carboxyl-CoA hydrolase (acting on C—C bond), 6-ketocyclohex-1-ene-1-carboxyl-CoA reductase, 2-ketocyclohexane-1-carboxylate decarboxylase, and an enzyme selected from the group consisting of 2-ketocyclohexane-1-carboxyl-CoA synthetase, 2-ketocyclohexane-1-carboxyl-CoA transferase, and 2-ketocyclohexane-1-carboxyl-CoA hydrolase (acting on thioester).

Organisms having a cyclohexanone pathway for converting 3-hydroxypimeloyl-CoA to cyclohexanone can include a PEP carboxykinase. The PEP carboxykinase can be encoded by one or more genes selected from the group consisting of PCK1, pck, and pckA.

Organisms having a cyclohexanone pathway for converting 3-hydroxypimeloyl-CoA to cyclohexanone can include a 6-ketocyclohex-1-ene-1-carboxyl-CoA hydrolase (acting on C—C bond). The 6-ketocyclohex-1-ene-1-carboxyl-CoA hydrolase (acting on C—C bond) can be encoded by one or more genes selected from bzdY, oah, bamA, syn_01653, syn_02400, syn_03076, and syn_01309.

Organisms having a cyclohexanone pathway for converting 3-hydroxypimeloyl-CoA to cyclohexanone can include a 6-ketocyclohex-1-ene-1-carboxyl-CoA synthetase. The 6-ketocyclohex-1-ene-1-carboxyl-CoA synthetase can be encoded by one or more genes selected from AF1211, AF1983, scs, PAE3250, sucC, sucD, aliA, phl, phlB, paaF, and bioW.

Organisms having a cyclohexanone pathway for converting 3-hydroxypimeloyl-CoA to cyclohexanone can include a 6-ketocyclohex-1-ene-1-carboxyl-CoA hydrolase (acting on thioester). The 6-ketocyclohex-1-ene-1-carboxyl-CoA hydrolase (acting on thioester) can be encoded by one or more genes selected from the group consisting of acot12, gctA, gctB, and ACH1.

Organisms having a cyclohexanone pathway for converting 3-hydroxypimeloyl-CoA to cyclohexanone can include a 6-ketocyclohex-1-ene-1-carboxyl-CoA transferase. The 6-ketocyclohex-1-ene-1-carboxyl-CoA transferase can be encoded by one or more genes selected from pcaI, pcaJ, catI, catJ, HPAG1_0676, HPAG1_0677, ScoA, ScoB, OXCT1, OXCT2, ctfA, ctfB, atoA, and atoD.

Organisms having a cyclohexanone pathway for converting 3-hydroxypimeloyl-CoA to cyclohexanone can include a 6-ketocyclohex-1-ene-1-carboxyl-CoA reductase. The 6-ketocyclohex-1-ene-1-carboxyl-CoA reductase can be encoded by one or more genes selected from bcd, etfA, etfB, TER, TDE0597, syn_02587, syn_02586, syn_01146, syn_00480, syn_02128, syn_01699, syn_02637, syn_02636, pimC, pimD, acad1, and acad.

Organisms having a cyclohexanone pathway for converting 3-hydroxypimeloyl-CoA to cyclohexanone can include a 6-ketocyclohex-1-ene-1-carboxylate decarboxylase. The 6-ketocyclohex-1-ene-1-carboxylate decarboxylase can be encoded by one or more genes selected from adc, cbei_3835, CLL_A2135, and RBAM_030030.

Organisms having a cyclohexanone pathway for converting 3-hydroxypimeloyl-CoA to cyclohexanone can include a 6-ketocyclohex-1-ene-1-carboxylate reductase. The 6-ketocyclohex-1-ene-1-carboxylate reductase can be encoded by one or more genes selected from NtRed1, AtDBR1, P2, PulR, PtPPDBR, YML131W, ispR, AT3G61220, cbr, CBR1, CHO—CR, YIR036c, enr and fadH.

Organisms having a cyclohexanone pathway for converting 3-hydroxypimeloyl-CoA to cyclohexanone can include a 2-ketocyclohexane-1-carboxyl-CoA synthetase. The 2-ketocyclohexane-1-carboxyl-CoA synthetase can be encoded by one or more genes selected from AF1211, AF1983, scs, PAE3250, sucC, sucD, aliA, phl, phlB, paaF, and bioW.

Organisms having a cyclohexanone pathway for converting 3-hydroxypimeloyl-CoA to cyclohexanone can include a 2-ketocyclohexane-1-carboxyl-CoA transferase. The 2-ketocyclohexane-1-carboxyl-CoA transferase can be encoded by one or more genes selected from pcaI, pcaJ, catI, catJ, HPAG1_0676, HPAG1_0677, ScoA, ScoB, OXCT1, OXCT2, ctfA, ctfB, atoA, and atoD.

Organisms having a cyclohexanone pathway for converting 3-hydroxypimeloyl-CoA to cyclohexanone can include a 2-ketocyclohexane-1-carboxyl-CoA hydrolase (acting on thioester). The 2-ketocyclohexane-1-carboxyl-CoA hydrolase (acting on thioester) can be encoded by one or more genes selected from acot12, gctA, gctB, and ACH1.

Organisms having a cyclohexanone pathway for converting 3-hydroxypimeloyl-CoA to cyclohexanone can include a 2-ketocyclohexane-1-carboxylate decarboxylase. The 2-ketocyclohexane-1-carboxylate decarboxylase can be encoded by one or more genes selected from adc, cbei_3835, CLL_A2135, and RBAM_030030.

Organisms having a cyclohexanone pathway for converting 3-hydroxypimeloyl-CoA to cyclohexanone can include a cyclohexanone dehydrogenase. The cyclohexanone dehydrogenase can be encoded by one or more genes selected from NtRed1, AtDBR1, P2, PulR, PtPPDBR, YML131W, ispR, AT3G61220, cbr, CBR1, CHO—CR, YIR036c, enr and fadH.

Organisms having a cyclohexanone pathway for converting 3-hydroxypimeloyl-CoA to cyclohexanone can include a 3-hydroxypimeloyl-CoA pathway that includes at least one exogenous nucleic acid encoding a 3-hydroxypimeloyl-CoA pathway enzyme expressed in a sufficient amount to produce 3-hydroxypimeloyl-CoA. The 3-hydroxypimeloyl-CoA pathway includes a acetoacetyl-CoA, a 3-hydroxybutyryl-CoA dehydratase, a glutaryl-CoA dehydrogenase, a oxopimeloyl-CoA:glutaryl-CoA acyltransferase, and a 3-hydroxypimeloyl-CoA dehydrogenase, as previously discussed with respect to FIG. 2. Any number of exogenous nucleic acids encoding a 3-hydroxypimeloyl-CoA enzyme can be provided in a non-naturally occurring microbial organism, including two, three, four, five, that is, up to all the enzymes to convert acetoacetyl-CoA to 3-hydroxypimeloyl-CoA as shown in FIG. 2. The same sets of genes used in the pathway for the production of pimeloyl-CoA can be used in a 3-hydroxypimeloyl-CoA pathway, leaving out the final dehydration and reduction steps used to produce pimeloyl-CoA.

Figure 4:
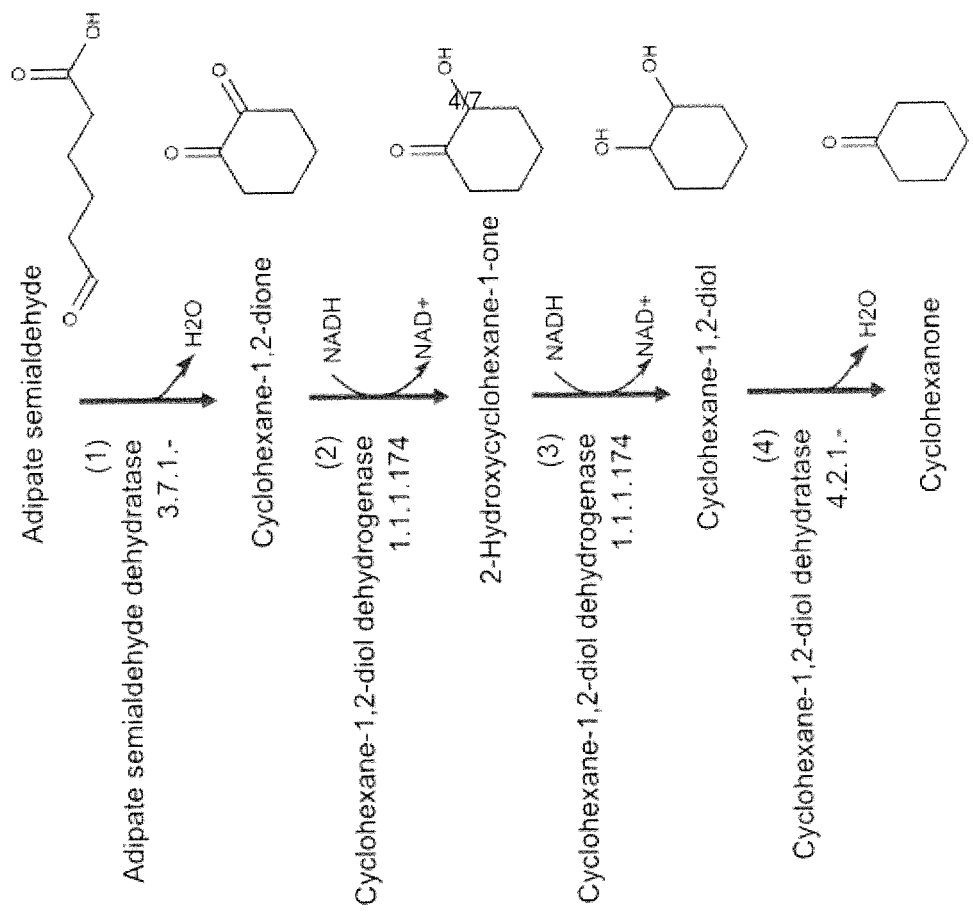
FIG. 4 shows the transformation of adipate semialdehyde to cyclohexanone.

In yet further embodiments, the present invention provides a non-naturally occurring microbial organism that includes a microbial organism having a cyclohexanone pathway having at least one exogenous nucleic acid encoding a cyclohexanone pathway enzyme expressed in a sufficient amount to produce cyclohexanone, as shown in FIG. 4. The cyclohexanone pathway includes a PEP carboxykinase, an adipate semialdehyde dehydratase, a cyclohexane-1,2-diol dehydrogenase, and a cyclohexane-1,2-diol dehydratase. Any number of these enzymes in the cyclohexanone pathway can be included by providing an appropriate exogenous nucleic acid, including up to all the nucleic acids encoding each of the enzymes in the complete pathway. The non-naturally occurring microbial organism can include for example, two exogenous nucleic acids each encoding a cyclohexanone pathway enzyme. In other embodiments, the organism can include three exogenous nucleic acids each encoding a cyclohexanone pathway enzyme. In still further embodiments, the non-naturally occurring microbial organism can include four exogenous nucleic acids each encoding a cyclohexanone pathway enzyme. Any of the nucleic acids added exogenously can be provided a heterologous nucleic acid. Such non-naturally occurring microbial organism can be provided in (and cultured in) a substantially anaerobic culture medium.

Organisms having a cyclohexanone pathway for converting adipate semialdehyde to cyclohexanone can include a PEP carboxykinase. The PEP carboxykinase can be encoded by one or more genes selected from PCK1, pck, and pckA.

Organisms having a cyclohexanone pathway for converting adipate semialdehyde to cyclohexanone can include a cyclohexane-1,2-diol dehydrogenase. The cyclohexane-1,2-diol dehydrogenase can be encoded by one or more genes selected from chnA, Rmet_1335, PP_19-16, ARA 1, BDH1, GCY1, YPR1, GRE3, and YIR036c.

Organisms having a cyclohexanone pathway for converting adipate semialdehyde to cyclohexanone can include a cyclohexane-1,2-diol dehydratase. The cyclohexane-1,2-diol dehydratase can be encoded by one or more genes selected from pddC, pddB, pddA, pduC, pduD, pduE, dhaB, dhaC, dhaE, dhaB1, dhaB2, rdhtA, rdhtB, ilvD, iolE, ddrA, ddrB, pduG, and pduH.

Figure 5:
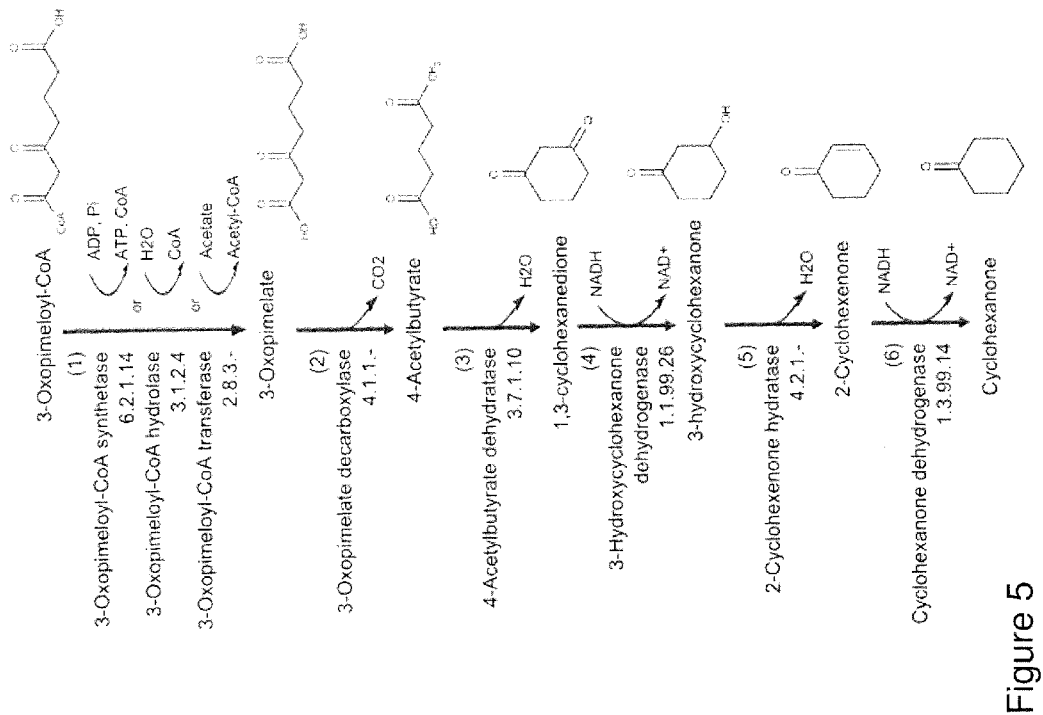
FIG. 5 shows the transformation of 3-oxopimeloyl-CoA to cyclohexanone.

In still further embodiments, the invention provides a non-naturally occurring microbial organism that includes a microbial organism having a cyclohexanone pathway having at least one exogenous nucleic acid encoding a cyclohexanone pathway enzyme expressed in a sufficient amount to produce cyclohexanone. The cyclohexanone pathway includes a PEP carboxykinase, a 3-oxopimelate decarboxylase, a 4-acetylbutyrate dehydratase, a 3-hydroxycyclohexanone dehydrogenase, a 2-cyclohexenone hydratase, a cyclohexanone dehydrogenase and an enzyme selected from a 3-oxopimeloyl-CoA synthetase, a 3-oxopimeloyl-CoA hydrolase (acting on thioester), and a 3-oxopimeloyl-coA transferase. Such an organism converts 3-oxopimeloyl-CoA to cyclohexanone as shown in FIG. 5. The microbial organism can include two, three, four, five, six, seven, that is up to all the enzymes in a cyclohexanone pathway by providing exogenous nucleic acids each encoding a cyclohexanone pathway enzyme. The non-naturally occurring microbial organism can provide any number of these nucleic as a heterologous nucleic acid. Additionally, such organisms can be provided in (or cultured in) a substantially anaerobic culture medium.

Organisms having a cyclohexanone pathway for converting 3-oxopimeloyl-CoA to cyclohexanone can include a PEP carboxykinase. The PEP carboxykinase can be encoded by one or more genes selected from PCK1, pck, and pckA.

Organisms having a cyclohexanone pathway for converting 3-oxopimeloyl-CoA to cyclohexanone can include a 3-oxopimelate decarboxylase. The 3-oxopimelate decarboxylase can be encoded by one or more genes selected from adc, cbei_3835, CLL_A2135, and RBAM_030030.

Organisms having a cyclohexanone pathway for converting 3-oxopimeloyl-CoA to cyclohexanone can include a 3-hydroxycyclohexanone dehydrogenase. The 3-hydroxycyclohexanone dehydrogenase can be encoded by one or more genes selected from YMR226c, YDR368w, YOR120w, YGL157w, YGL039w, chnA, Rmet_1335, PP_1946, ARA1, BDH1, GCY1, YPR1, GRE3 and YIR036c.

Organisms having a cyclohexanone pathway for converting 3-oxopimeloyl-CoA to cyclohexanone can include a 2-cyclohexenone hydratase. The 2-cyclohexenone hydratase can be encoded by one or more genes selected from aroD, aroQ, HIDH, and HIDM.

Organisms having a cyclohexanone pathway for converting 3-oxopimeloyl-CoA to cyclohexanone can include a cyclohexanone dehydrogenase. The cyclohexanone dehydrogenase can be encoded by one or more genes selected from NtRed1, AtDBR1, P2, PulR, PtPPDBR, YML131W, ispR, AT3G61220, cbr, CBR1, CHO—CR, YIR036c, enr and fadH.

Organisms having a cyclohexanone pathway for converting 3-oxopimeloyl-CoA to cyclohexanone can include a 3-oxopimeloyl-CoA synthetase. The 3-oxopimeloyl-CoA synthetase can be encoded by one or more genes selected from AF1211, AF1983, scs, PAE3250, sucC, sucD, aliA, phl, phiB, paaF, and bioW.

Organisms having a cyclohexanone pathway for converting 3-oxopimeloyl-CoA to cyclohexanone can include a 3-oxopimeloyl-CoA hydrolase. The 3-oxopimeloyl-CoA hydrolase can be encoded by one or more genes selected from the group consisting of acot12, gctA, gctB, and ACH1.

Organisms having a cyclohexanone pathway for converting 3-oxopimeloyl-CoA to cyclohexanone can include a 3-oxopimeloyl-CoA transferase. The 3-oxopimeloyl-CoA transferase can be encoded by one or more genes selected from pcaI, peaJ, catI, catJ, HPAG1_0676, HPAG1_0677, ScoA, ScoB, OXCT1, OXCT2, ctfA, ctfB, atoA, and atoD.

Organisms having a cyclohexanone pathway for converting 3-oxopimeloyl-CoA to cyclohexanone can include a 3-oxopimeloyl-CoA pathway that includes at least one exogenous nucleic acid encoding a 3-oxopimeloyl-CoA pathway enzyme expressed in a sufficient amount to produce 3-oxopimeloyl-CoA. The 3-oxopimeloyl-CoA pathway includes an acetoacetyl-CoA, a 3-hydroxybutyryl-CoA dehydratase, a glutaryl-CoA dehydrogenase, and a oxopimeloyl-CoA:glutaryl-CoA acyltransferase, as previously discussed with respect to FIG. 2. Any number of exogenous nucleic acids encoding a 3-oxopimeloyl-CoA enzyme can be provided in a non-naturally occurring microbial organism, including two, three, four, that is, up to all the enzymes to convert acetoacetyl-CoA to 3-oxopimeloyl-CoA as shown in FIG. 2. The same sets of genes used in the pathway for the production of pimeloyl-CoA can be used in a 3-oxopimeloyl-CoA pathway, leaving out the final ketone reduction, dehydration and olefin reduction steps used to produce pimeloyl-CoA.

In an additional embodiment, the invention provides a non-naturally occurring microbial organism having a cyclohexanone pathway, wherein the non-naturally occurring microbial organism comprises at least one exogenous nucleic acid encoding an enzyme or protein that converts a substrate to a product selected from the group consisting of pimeloyl-CoA to 2-ketocyclohexane-1-carboxyl-CoA, 2-ketocyclohexane-1-carboxyl-CoA to 2-ketocyclohexane-1-carboxylate, and 2-ketocyclohexane-1-carboxylate to cyclohexanone. Thus, the invention provides a non-naturally occurring microbial organism containing at least one exogenous nucleic acid encoding an enzyme or protein, where the enzyme or protein converts the substrates and products of a cyclohexanone pathway, such as that shown in FIG. 1.

In an additional embodiment, the invention provides a non-naturally occurring microbial organism having a pimeloyl-CoA pathway, wherein the non-naturally occurring microbial organism comprises at least one exogenous nucleic acid encoding an enzyme or protein that converts a substrate to a product selected from the group consisting of acetoacetyl-CoA to 3-hydroxybutyryl-CoA, 3-hydroxybutyryl-CoA to crotonyl-CoA, crotonyl-CoA to glutaryl-CoA, glutaryl-CoA to 3-oxopimeloyl-CoA, 3-oxopimeloyl-CoA to 3-hydroxypimeloyl-CoA, 3-hydroxypimeloyl-CoA to 6-carboxyhex-2-enoyl-CoA, and 6-carboxyhex-2-enoyl-CoA to pimeloyl-CoA. Thus, the invention provides a non-naturally occurring microbial organism containing at least one exogenous nucleic acid encoding an enzyme or protein, where the enzyme or protein converts the substrates and products of a cyclohexanone pathway, such as that shown in FIG. 2.

In an additional embodiment, the invention provides a non-naturally occurring microbial organism having a cyclohexanone pathway, wherein the non-naturally occurring microbial organism comprises at least one exogenous nucleic acid encoding an enzyme or protein that converts a substrate to a product selected from the group consisting of 3-hydroxypimeloyl-CoA to 6-ketocyclohex-1-ene-1-carboxyl-CoA, 6-ketocyclohex-1-ene-1-carboxyl-CoA to 6-ketocyclohex-1-ene-1-carboxylate, 6-ketocyclohex-1-ene-1-carboxylate to 2-cyclohexenone, and 2-cyclohexenone to cyclohexanone. Thus, the invention provides a non-naturally occurring microbial organism containing at least one exogenous nucleic acid encoding an enzyme or protein, where the enzyme or protein converts the substrates and products of a cyclohexanone pathway, such as that shown in FIG. 3.

In an additional embodiment, the invention provides a non-naturally occurring microbial organism having a cyclohexanone pathway, wherein the non-naturally occurring microbial organism comprises at least one exogenous nucleic acid encoding an enzyme or protein that converts a substrate to a product selected from the group consisting of 3-hydroxypimeloyl-CoA to 6-ketocyclohex-1-ene-1-carboxyl-CoA, 6-ketocyclohex-1-ene-1-carboxyl-CoA to 6-ketocyclohex-1-ene-1-carboxylate, 6-ketocyclohex-1-ene-1-carboxylate to 2-ketocyclohexane-1-carboxylate, and 2-ketocyclohexane-1-carboxylate to cyclohexanone. Thus, the invention provides a non-naturally occurring microbial organism containing at least one exogenous nucleic acid encoding an enzyme or protein, where the enzyme or protein converts the substrates and products of a cyclohexanone pathway, such as that shown in FIG. 3.

In an additional embodiment, the invention provides a non-naturally occurring microbial organism having a cyclohexanone pathway, wherein the non-naturally occurring microbial organism comprises at least one exogenous nucleic acid encoding an enzyme or protein that converts a substrate to a product selected from the group consisting of 3-hydroxypimeloyl-CoA to 6-ketocyclohex-1-ene-1-carboxyl-CoA, 6-ketocyclohex-1-ene-1-carboxyl-CoA to 2-ketocyclohexane-1-carboxyl-CoA, 2-ketocyclohexane-1-carboxyl-CoA to 2-ketocyclohexane-1-carboxylate, and 2-ketocyclohexane-1-carboxylate to cyclohexanone. Thus, the invention provides a non-naturally occurring microbial organism containing at least one exogenous nucleic acid encoding an enzyme or protein, where the enzyme or protein converts the substrates and products of a cyclohexanone pathway, such as that shown in FIG. 3.

In an additional embodiment, the invention provides a non-naturally occurring microbial organism having a cyclohexanone pathway, wherein the non-naturally occurring microbial organism comprises at least one exogenous nucleic acid encoding an enzyme or protein that converts a substrate to a product selected from the group consisting of adipate semialdehyde to cyclohexane-1,2-dione, cyclohexane-1,2-dione to 2-hydroxycyclohexan-1-one, 2-hydroxycyclohexan-1-one to cyclohexane-1,2-diol, and cyclohexane-1,2-diol to cyclohexanone. Thus, the invention provides a non-naturally occurring microbial organism containing at least one exogenous nucleic acid encoding an enzyme or protein, where the enzyme or protein converts the substrates and products of a cyclohexanone pathway, such as that shown in FIG. 4.

In an additional embodiment, the invention provides a non-naturally occurring microbial organism having a cyclohexanone pathway, wherein the non-naturally occurring microbial organism comprises at least one exogenous nucleic acid encoding an enzyme or protein that converts a substrate to a product selected from the group consisting of 3-oxopimeloyl-CoA to 3-oxopimelate, 3-oxopimelate to 4-acetylbutyrate, 4-acetylbutyrate to 1,3-cyclohexanedione, 1,3-cyclohexanedione to 3-hydroxycyclohexanone, 3-hydroxycyclohexanone to 2-cyclohexenone, and 2-cyclohexenone to cyclohexanone. Thus, the invention provides a non-naturally occurring microbial organism containing at least one exogenous nucleic acid encoding an enzyme or protein, where the enzyme or protein converts the substrates and products of a cyclohexanone pathway, such as that shown in FIG. 5.

In an additional embodiment, the invention provides a non-naturally occurring microbial organism having a pimeloyl-CoA pathway, wherein the non-naturally occurring microbial organism comprises at least one exogenous nucleic acid encoding an enzyme or protein that converts a substrate to a product selected from the group consisting of 2,6-diaminoheptanedioc acid to 6-aminohept-2-enedioic acid, 6-aminohept-2-enedioic acid to 2-aminoheptanedioic acid, 2-aminoheptanedioic acid to 6-carboxyhex-2-eneoate, 6-carboxyhex-2-eneoate to pimelate, and pimelate to pimeloyl-CoA. Thus, the invention provides a non-naturally occurring microbial organism containing at least one exogenous nucleic acid encoding an enzyme or protein, where the enzyme or protein converts the substrates and products of a cyclohexanone pathway, such as that shown in FIG. 7.

Figure 3:
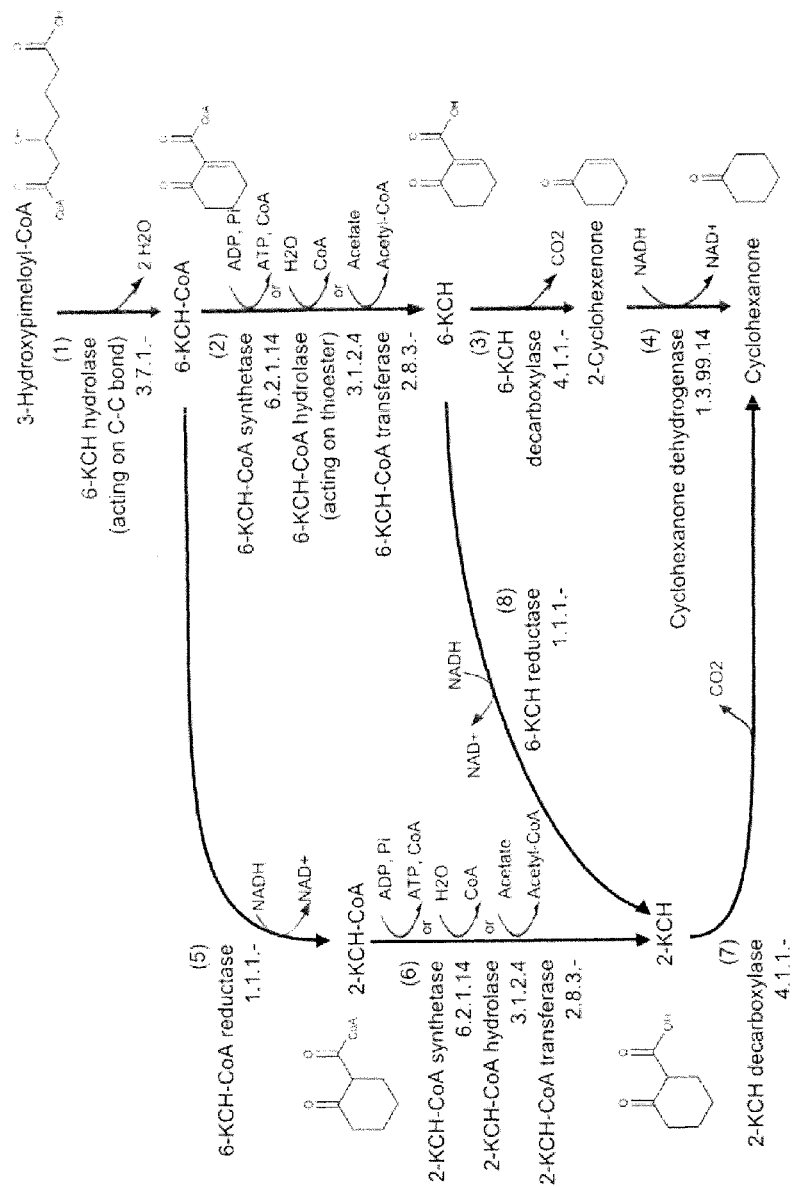
FIG. 3 shows the transformation of 3-hydroxypimeloyl-CoA to cyclohexanone. Abbreviations: 6-KCH-CoA=6-ketocyclohex-1-ene-1-carboxyl-CoA, 6-KCH=6-carboxyhex-1-ene-1-carboxylate, 2KCH-CoA=2-ketocyclohexane-1-carboxyl-CoA, 2-KCH=2-ketocyclohexane-1-carboxylate.
Figure 6:
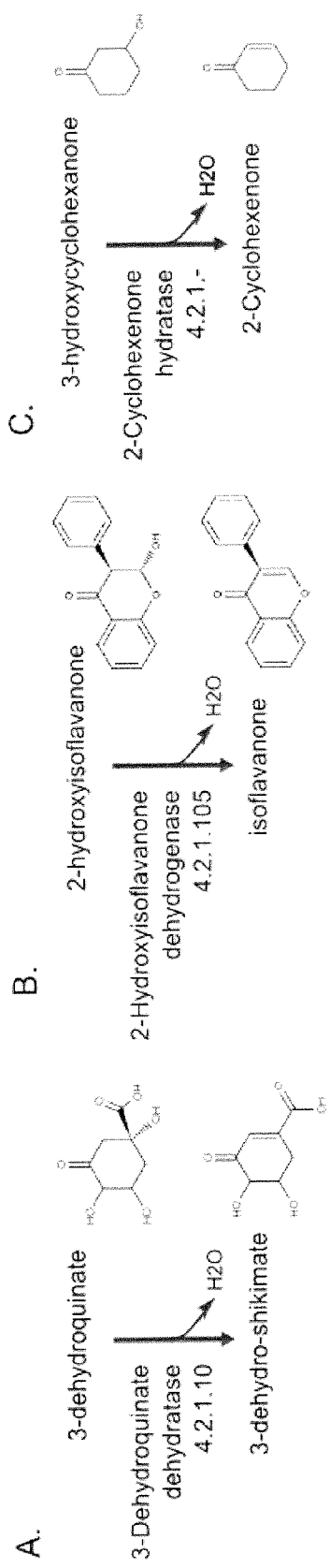
FIG. 6 shows the enzymatic activities of A) 3-dehydroquinate dehydratase, B) 2-hydroxyisoflavanone dehydrogenase, and C) 2-cyclohexenone hydratase.
Figure 7:
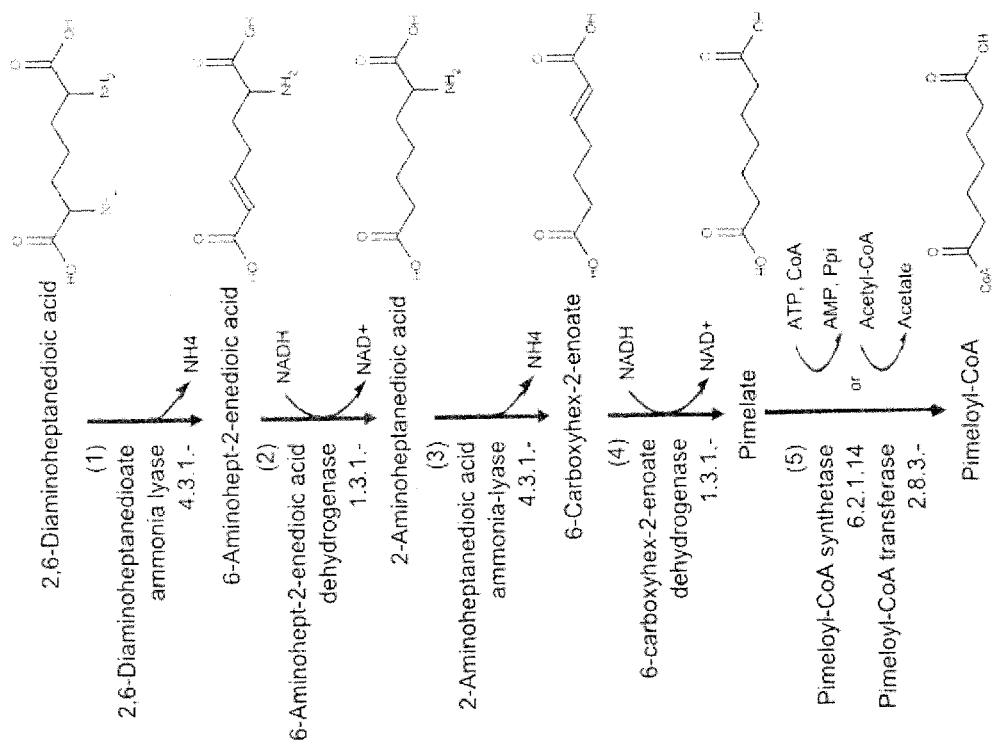
FIG. 7 shows a route to pimeloyl-CoA from 2,6-diaminopimelate.

While generally described herein as a microbial organism that contains a cyclohexanone pathway, it is understood that the invention additionally provides a non-naturally occurring microbial organism comprising at least one exogenous nucleic acid encoding a cyclohexanone pathway enzyme expressed in a sufficient amount to produce an intermediate of a cyclohexanone pathway. For example, as disclosed herein, a cyclohexanone pathway is exemplified in FIGS. 1-5 and 7. Therefore, in addition to a microbial organism containing a cyclohexanone pathway that produces cyclohexanone, the invention additionally provides a non-naturally occurring microbial organism comprising at least one exogenous nucleic acid encoding a cyclohexanone pathway enzyme, where the microbial organism produces a cyclohexanone pathway intermediate, for example, 2-KCH-CoA or 2-KCH as shown in FIG. 1, 3-hydroxybutyryl-CoA, crotonyl-CoA, glutaryl-CoA, 3-oxopimeloyl-CoA, 3-hydroxypimeloyl-CoA, or pimeloyl-CoA as shown in FIG. 2, 2-KCH, 2-KCB-CoA, 6-KCH-CoA, 6-KCH, or 2-cyclohexenone, as shown in FIG. 3, cyclohexane-1,2-dione, 2-hydroxycyclohexane-1-one, or cyclohexan-1,2-diol, as shown in FIG. 4, 3-oxopimelate, 4-acetylbutyrate, 1,3-cyclohexanedione, 3-hydroxycyclohexanone, or 2-cyclohexenone, as shown in FIGS. 5, and 6-aminohept-2-enedioc acid, 2-aminoheptanedioic acid, 6-carboxyhex-2-enoate, or pimelate, as shown in FIG. 7.

It is understood that any of the pathways disclosed herein, as described in the Examples and exemplified in the Figures, including the pathways of FIGS. 1-5 and 7, can be utilized to generate a non-naturally occurring microbial organism that produces any pathway intermediate or product, as desired. As disclosed herein, such a microbial organism that produces an intermediate can be used in combination with another microbial organism expressing downstream pathway enzymes to produce a desired product. However, it is understood that a non-naturally occurring microbial organism that produces a cyclohexanone pathway intermediate can be utilized to produce the intermediate as a desired product.

The invention is described herein with general reference to the metabolic reaction, reactant or product thereof, or with specific reference to one or more nucleic acids or genes encoding an enzyme associated with or catalyzing, or a protein associated with, the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction, and reference to any of these metabolic constituents also references the gene or genes encoding the enzymes that catalyze or proteins involved in the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes or a protein associated with the reaction as well as the reactants and products of the reaction.

In some embodiments, a cyclohexanone pathway includes enzymes that convert pimeloyl-CoA to cyclohexanone in three enzymatic steps as shown in FIG. 1. In this route, pimeloyl-CoA is cyclized to 2-ketocyclohexane-1-carboxyl- CoA (2KCH-CoA) by 2-ketocyclohexane-1-carboxyl-CoA hydrolase (acting on C—C bond). The 2KCH-CoA hydrolase is run in the reverse, i.e. ring-closing direction as shown in FIG. 1. The CoA ester is then converted to 2-ketocyclohexane-1-carboxylate by reaction of 2-ketocyclohexane-1-carboxyl-CoA with a CoA synthetase, hydrolase or transferase. Finally decarboxylation of 2-ketocyclohexane-1-carboxylate yields cyclohexanone.

The energetics and theoretical cyclohexanone yield of this pathway, shown in Table 1, are dependent on: 1) the type of enzyme utilized for removing the CoA moiety in step 2, 2) the biosynthetic pathway for producing pimeloyl-CoA, and 3) the ability of PEP carboxykinase to operate in the ATP-generating direction.

TABLE 1

|  | Cyclohexanone (mol/mol glucose) | ATP @ max yield (mol/mol glucose) |
| --- | --- | --- |
| Hydrolase | 0.738 | 0 |
| Hydrolase, PPCKr | .075 | 0.31 |
| Transferase | 0.75 | 0.56 |
| Transferase, PPCKr | 0.75 | 1.06 |

A strain that produces pimeloyl-CoA as described herein, with a transferase or synthetase in step (2), and a reversible PEP carboxykinase has a theoretical yield of 0.75 moles of cyclohexanone per mole glucose utilized (0.41 g/g). This strain has an energetic yield of 1.06 moles ATP per mole glucose utilized.

Enzymes for each step of a cyclohexanone pathway are described below. In some embodiments, native pathways for producing pimeloyl-CoA can be utilized, while in other embodiments novel pathways for synthesizing pimeloyl-CoA from central metabolic precursors are used.

The first step of the pathway involves formation of 2-ketocyclohexane-1-carboxyl-CoA from pimeloyl-CoA as shown in step 1 of FIG. 1. This transformation has been indicated to occur in the ring-closing direction in *Syntrophus aciditrophicus* during growth on crotonate (Mouttaki et al., *Appl. Environ. Micobiol.* 73:930-938 (2007)). This enzyme activity was also demonstrated in cell-free extracts of *S. aciditrophicus* in co-culture with another microbe during growth on benzoate (Elshahed et al., *Appl. Environ. Microbiol.* 67:1728-1738 (2001)). An enzyme catalyzing this activity in the ring-opening direction has been characterized in *Rhodopseudomonas palustris*, where it is encoded by badI (Pelletier et al., *J. Bacteriol.* 180:2330-2336 (1998)). The *R. palustris* enzyme has been expressed in *E. coli* where it was assayed for enzymatic activity in the ring-opening direction; however, such activity was not observed (Egland et al., *Proc. Natl. Acad. Sci. U.S.A.* 94:6484-6489 (1997)). Several genes in the *S. aciditrophicus* genome bear sequence homology to the badI gene of *R. palustris* (McInerney et al., *Proc. Natl Acad. Sci. U.S.A.* 104:7600-7605 (2007)), including syn_01653 (38%), syn_03076 (33%), syn_02400 (33%), syn_03076 (30%) and syn_01309 (31%). The protein sequences for exemplary gene products can be found using the following GenBank accession numbers shown below in Table 2.

TABLE 2

| Protein | GenBank ID | GI Number | Organism |
| --- | --- | --- | --- |
| badI | NP_946006.1 | 39933730 | Rhodopseudomonas palustris |
| syn_01653 | YP_463074.1 | 85860872 | Syntrophus aciditrophicus |
| syn_01654 | YP_463073.1 | 85860871 | Syntrophus aciditrophicus |

TABLE 2-continued

| Protein | GenBank ID | GI Number | Organism |
| --- | --- | --- | --- |
| syn_02400 | YP_462924.1 | 85860722 | Syntrophus aciditrophicus |
| syn_03076 | YP_463118.1 | 85860916 | Syntrophus aciditrophicus |
| syn_01309 | YP_461962.1 | 85859760 | Syntrophus aciditrophicus |

Napthoyl-CoA synthetase (EC 4.1.3.36), an enzyme participating in menaquinone biosynthesis, catalyzes the ring-closing conversion of succinyl-benzoyl-CoA to 1,4-dihydroxy-2-napthoyl-CoA. The badI gene product of *R. palustris* shares as much as 53% sequence identity with 1,4-dihydroxynapthoyl-CoA synthetase homologs in other organisms (Eberhard et al., *J. Am. Chem. Soc.* 126:7188-7189 (2004)), and enzymes catalyzing this transformation can demonstrate 2-ketocyclohexane-1-carboxyl-CoA hydrolase (acting on C—C bond) activity in the ring-closing direction. Such enzymes are found in *Escherichia coli* (Sharma et al., *J. Bacteriol.* 174:5057-5062 (1992)), *Bacillus subtilis* (Driscoll et al., *J. Batceriol.* 174:5063-5071 (1992)), *Staphylococcus aureus* (Ulaganathan et al., *Acta Crstyallogr. Sect. F. Struct. Biol. Cyst. Commun.* 63:908-913 (2007)) and *Geobacillus kaustophilus* (Kanajunia et al., *Acta Crstyallogr. Sect. F. Struct. Biol. Cyst. Commun.* 63:103-105 (2007)). Additionally, structural data is available for the enzymes from *Mycobacterium tuberculosis* (Johnston et al., *Acta Crstyallogr. D. Biol. Crystallogr.* 61:1199-1206 (2005)), *S. aureus* (Ulaganathan et al., supra) and *Geobacillus kaustophilus* (Kanaujia et al., supra). The protein sequences for exemplary gene products can be found using the following GenBank accession numbers shown below in Table 3.

TABLE 3

| Protein | GenBank ID | GI Number | Organism |
| --- | --- | --- | --- |
| menB | AAC75322 | 1788597 | Escherichia coli K12 sp. MG1655 |
| menB | AAC37016 | 143186 | Bacillus subtilis |
| menB | NP_215062 | 15607688 | Mycobacterium tuberculosis |
| menB | BAB57207 | 14246815 | Staphylococcus aureus |
| menB | BAD77158 | 56381250 | Geobacillus kaustophilus |

The reaction of 2-ketocyclohexane-1-carboxyl-CoA to 2-ketocyclohexane-1-carboxylate, shown in FIG. 1, step 2, can be accomplished by a CoA hydrolase, transferase or synthetase. 3-oxoacid CoA transferases include 3-oxoadipate CoA-transferase (EC 2.8.3.6), 3-oxoacid CoA transferase (2.8.3.5) and acetate-acetoacetate CoA-transferase (2.8.3.-). 3-Oxoadipate CoA transferase (EC 2.8.3.6) catalyzes the transfer of the CoA moiety from succinyl-CoA to 3-oxoadipate, a molecule close in structure to 3-oxopimelate. Participating in beta-ketoadipate pathways for aromatic compound degradation (Harwood et al., *Annu. Rev. Microbiol.* 50:553-590 (1996)), this enzyme has been characterized in *Pseudomonas putida* (Parales et al., *Bacteriol.* 174:4657-4666 (1992)), *Acinetobacter calcoaceticus* (sp. ADP1) (Dal et al., *Appl. Environ. Microboiol.* 71:1025-1034 (2005); Yeh et al., *J. Biol. Chem.* 256:1565-1569 (1981) and *Pseudomonas knackmussii* (formerly sp. B13) (Gobel et al., *J. Bacteriol.* 184:216-223 (2002); Kaschabek et al., *J. Bacteriol* 184:207-215 (2002). The protein sequences for exemplary gene products can be found using the following GenBank accession numbers shown below in Table 4.

TABLE 4

| Protein | GenBank ID | GI Number | Organism |
|---|---|---|---|
| pcaI | Q01103.2 | 24985644 | *Pseudomonas putida* |
| pcaJ | P0A102.2 | 26990657 | *Pseudomonas putida* |
| pcaI (catI) | AAC37146.1 | 684991 | *Acinetobacter calcoaceticus* (sp. ADP1) |
| pcaJ (catJ) | AAC37147.1 | 141776 | *Acinetobacter calcoaceticus* (sp. ADP1) |
| catI | Q8VPF3.1 | 75404583 | *Pseudomonas knackmussii* |
| catJ | Q8VPF2.1 | 75404582 | *Pseudomonas knackmussii* |

Another CoA transferase for this reaction step is succinyl-CoA:3-ketoacid-CoA transferase. This enzyme converts succinate to succinyl-CoA while converting a 3-ketoacyl-CoA to a 3-ketoacid. Exemplary succinyl-CoA:3:ketoacid-CoA transferases are present in *Helicobacter pylori* (Corthesy-Theulaz et al., *J. Biol. Chem.* 272:25659-25667 (1997)), *Bacillus subtilis* (Stols et al., *Protein. Expr. Purif.* 53:396-403 (2007), and *Homo sapiens* (Fukao et al., *Genomics* 68:144-)51 (2000); Tanaka et al., *Mol. Hum. Reprod.* 8:16-23 (2002)). The protein sequences for exemplary gene products can be found using the following GenBank accession numbers shown below in Table 5.

TABLE 5

| Protein | GenBank ID | GI Number | Organism |
|---|---|---|---|
| HPAG1_0676 | YP_627417 | 108563101 | *Helicobacter pylori* |
| HPAG1_0677 | YP_627418 | 108563102 | *Helicobacter pylori* |
| ScoA | NP_391778 | 16080950 | *Bacillus subtilis* |
| ScoB | NP_391777 | 16080949 | *Bacillus subtilis* |
| OXCT1 | NP_000427 | 4557817 | *Homo sapiens* |
| OXCT2 | NP_071403 | 11545841 | *Homo sapiens* |

Acetate-acetoacetate CoA transferase naturally transfers the CoA moiety from acetoacetyl-CoA to acetate, forming acetyl-CoA and acetoacetate. Exemplary enzymes include the gene products of ctfAB in *Clostridium acetobutylicum* (Weisenborn et al., *App. Environ. Microbiol.* 55:323-329 (1989)), atoAD from *Escherichia coli* K12 (Sramek et al., *Arch. Biohem. Biophys.* 171:14-26 (1975)), and ctfAB from *Clostridium saccharoperbutylacetonicum* (Kosaka et al. Bopsco. Biotechnol. Biochem. 71:58-68 (2007)). The *Clostridium acetobutylicum* enzyme has been functionally expressed in *E. coli* (Cary et al., *Appl. Environ. Microbiol.* 56:1576-1583 (1990)). The CoA transferase in *E. coli* K12, encoded by atoA and atoD, has a fairly broad substrate specificity and has been shown to react with alternate 3-oxoacyl-CoA substrates (Sramek et al., supra). This enzyme is induced at the transcriptional level by acetoacetate, so modification of regulatory control can be performed to utilize this enzyme in a pathway (Pauli et al., *Euro. J. Biochem.* 29:553-562 (1972)). The protein sequences for exemplary gene products can be found using the following GenBank accession numbers shown below in Table 6.

TABLE 6

| Protein | GenBank ID | GI Number | Organism |
|---|---|---|---|
| ctfA | NP_149326.1 | 15004866 | *Clostridium acetobutylicum* |
| ctfB | NP_149327.1 | 15004867 | *Clostridium acetobutylicum* |
| atoA | NP_416726 | 2492994 | *Escherichia coli* K12 substr MG1655 |
| atoD | NP_416725 | 2492990 | *Escherichia coli* K12 substr MG1655 |
| ctfA | AAP42564.1 | 31075384 | *Clostridium saccharoperbutylacetonicum* |
| ctfB | AAP42565.1 | 31075385 | *Clostridium saccharoperbutylacetonicum* |

One ATP synthetase is ADP-forming acetyl-CoA synthetase (ACD, EC 6.2.1.13), an enzyme that couples the conversion of acyl-CoA esters to their corresponding acids with the concomitant synthesis of ATP. Although this enzyme has not been shown to react with 2-ketocyclohexane-1-carboxyl-CoA as a substrate, several enzymes with broad substrate specificities have been described in the literature. ACD I from *Archaeoglobus fulgidus*, encoded by AF1211, was shown to operate on a variety of linear and branched-chain substrates including isobutyrate, isopentanoate, and fumarate (Musfeldt et al., J. Bacteriol. 184:636-644 (2002)). A second reversible ACD in *Archaeoglobus fulgidus*, encoded by AF1983, was also shown to have a broad substrate range with high activity on cyclic compounds phenylacetate and indoleacetate (Musfeldt et al., supra). The enzyme from *Haloarcula marismortui* (annotated as a succinyl-CoA synthetase) accepts propionate, butyrate, and branched-chain acids (isovalerate and isobutyrate) as substrates, and was shown to operate in the forward and reverse directions (Brasen et al., *Arch. Microbiol.* 182:277-287 (2004)). The ACD encoded by PAE3250 from hyperthermophilic crenarchaeon *Pyrobaculum aerophilum* showed the broadest substrate range of all characterized ACDs, reacting with acetyl-CoA, isobutyryl-CoA (preferred substrate) and phenylacetyl-CoA (Brasen et al., supra). Directed evolution or engineering can be used to modify this enzyme to operate at the physiological temperature of the host organism. The enzymes from *A. fulgidus, H. marismortui* and *P. aerophilum* have all been cloned, functionally expressed, and characterized in *E. coli* (Brasen et al., supra; Musfeldt et al, supra). An additional enzyme is encoded by sucCD in *E. coli*, which naturally catalyzes the formation of succinyl-CoA from succinate with the concomitant consumption of one ATP, a reaction which is reversible in vivo (Buck et al., *Biochemistry* 24:6245-6252 (1985)). The protein sequences for exemplary gene products can be found using the following GenBank accession numbers shown below in Table 7.

TABLE 7

| Protein | GenBank ID | GI Number | Organism |
|---|---|---|---|
| AF1211 | NP_070039.1 | 11498810 | *Archaeoglobus fulgidus* DSM 4304 |
| AF1983 | NP_070807.1 | 11499565 | *Archaeoglobus fulgidus* DSM 4304 |
| scs | YP_135572.1 | 55377722 | *Haloarcula marismortui* ATCC 43049 |
| PAE3250 | NP_560604.1 | 18313937 | *Pyrobaculum aerophilum* str. IM2 |
| sucC | NP_415256.1 | 16128703 | *Escherichia coli* |
| sucD | AAC73823.1 | 1786949 | *Escherichia coli* |

Another possibility is mutating an AMP-forming CoA ligase to function in the reverse direction. The AMP-forming cyclohexanecarboxylate CoA-ligase from *Rhodopseudomonas palustris*, encoded by aliA, is active on a substrate similar to 2-ketocyclohexane-1-carboxyl-CoA, and alteration of the active site has been shown to impact the substrate specificity of the enzyme (Samanta et al., *Mol. Microbiol.* 55:1151-1159 (2005)). This enzyme also functions as a cyclohex-1-ene-1-carboxylate CoA-ligase during anaerobic benzene ring degradation (Egland et al., supra). It is unlikely, however, that the native form of this enzyme can function in the ATP-generating direction, as is required for formation of cyclohexane-1-carboxylate. Protein engineering or directed evolution can be used achieve this functionality. Additional exemplary CoA ligases include two characterized phenylacetate-CoA ligases from *P. chrysogenum* (Lamas-Maceiras et al., *Biochem. J.* 395:147-155 (2006); Wang et al., *Biochem. Biophys. Res. Commun.* 360:453-458 (2007)), the phenylacetate-CoA ligase from *Pseudomonas putida* (Martinez-Blanco et al., *Biol. Chem.* 265:7085-7090 (1990), and the 6-carboxyhexanoate-CoA ligase from *Bacillus subtilis* (Bower et al., *J. Bacteriol.* 178:4122-4130 (1996)). The protein sequences for exemplary gene products can be found using the following GenBank accession numbers shown below in Table 8.

TABLE 8

| Protein | GenBank ID | GI Number | Organism |
|---|---|---|---|
| aliA | AAC23919 | 2190573 | *Rhodopseudomonas palustris* |
| phl | CAJ15517.1 | 77019264 | *Penicillium chrysogenum* |
| phlB | ABS19624.1 | 152002983 | *Penicillium chrysogenum* |
| paaF | AAC24333.2 | 22711873 | *Pseudomonas putida* |
| bioW | NP_390902.2 | 50812281 | *Bacillus subtilis* |

2-Ketocyclohexane-1-carboxyl-CoA can also be hydrolyzed to 2-ketocyclohexane-1-carboxylate by a CoA hydrolase. Several eukaryotic acetyl-CoA hydrolases (EC 3.1.2.1) have broad substrate specificity. The enzyme from *Rattus norvegicus* brain (131) can react with butyryl-CoA, hexanoyl-CoA and malonyl-CoA. The enzyme from the mitochondrion of the pea leaf is active on diverse substrates including acetyl-CoA, propionyl-CoA, butyryl-CoA, palmitoyl-CoA, oleoyl-CoA, succinyl-CoA, and crotonyl-CoA (Zeiher et al., *Plant. Physiol.* 94:20-27 (1990)). Additionally, a glutaconate CoA-transferase from *Acidaminococcus fermentans* was transformed by site-directed mutagenesis into an acyl-CoA hydrolase with activity on glutaryl-CoA, acetyl-CoA and 3-butenoyl-CoA (Mack et al., *FEBS Lett.* 405:209-212 (1997)). This indicates that the enzymes encoding succinyl-CoA:3-ketoacid-CoA transferases and acetoacetyl-CoA:acetyl-CoA transferases can also serve as CoA hydrolase enzymes but would require certain mutations to change their function. The acetyl-CoA hydrolase, ACH1, from *S. cerevisiae* represents another hydrolase (Buu et al., *J. Biol. Chem.* 278:17203-17209 (2003)). The protein sequences for exemplary gene products can be found using the following GenBank accession numbers shown below in Table 9.

TABLE 9

| Protein | GenBank ID | GI Number | Organism |
|---|---|---|---|
| acot12 | _570103.1 | 18543355 | *Rattus norvegicus* |
| gctA | CAA57199 | 559392 | *Acidaminococcus fermentans* |
| gctB | CAA57200 | 559393 | *Acidaminococcus fermentans* |
| ACH1 | NP_009538 | 6319456 | *Saccharomyces cerevisiae* |

In the final step of the pathway cyclohexanone is formed by the decarboxylation of 2-ketocyclohexane carboxylate (FIG. 2, step 3). This reaction is catalyzed by a 3-oxoacid decarboxylase such as acetoacetate decarboxylase (EC 4.1.1.4). The acetoacetate decarboxylase from *Clostridium acetobutylicum*, encoded by adc, has a broad substrate range and has been shown to decarboxylate 2-ketocyclohexane carboxylate to yield cyclohexanone (Benner et al., *J. Am. Chem. Soc.* 103:993-994 (1981); Rozzel et al., *J. Am. Chem. Soc.* 106: 4937-4941 (1984)). The acetoacetate decarboxylase from *Bacillus polymyxa*, characterized in cell-free extracts, also has a broad substrate specificity for 3-keto acids and has been shown to decarboxylate the alternative substrate 3-oxopentanoate (Matiasek et al., *Curr. Microbiol.* 42:276-281 (2001)). Additional acetoacetate decarboxylase enzymes are found in *Clostridium beijerinckii* (Ravagnani et al., *Mol. Microbiol.* 37:1172-1185 (2000)) and *Clostridium saccharoperbutylacetonicum* (Kosaka et al., *Biosci. Biotechnol. Biochem.* 71:58-68 (2007)). Genes in other organisms, including *Clostridium botulinum* and *Bacillus amyloliquefaciens* FZB42, can be inferred by sequence homology. Decarboxylation of 3-oxoacids can also occur spontaneously in the absence of enzymes (Matiasek et al., supra)). The protein sequences for exemplary gene products can be found using the following GenBank accession numbers shown below in Table 10.

TABLE 10

| Protein | GenBank ID | GI Number | Organism |
|---|---|---|---|
| adc | NP_149328.1 | 15004868 | *Clostridium acetobutylicum* ATCC 824 |
| cbei_3835 | YP_001310906.1 | 150018652 | *lostridium beijerinckii* NCIMB 8052 |
| adc | AAP42566.1 | 31075386 | *Clostridium saccharoperbutylacetonicum* |
| CLL_A2135 | YP_001886324.1 | 187933144 | *Clostridium botulinum* |
| RBAM_030030 | YP_001422565.1 | 154687404 | *Bacillus amyloliquefaciens* FZB42 |

Although the net conversion of phosphoenolpyruvate to oxaloacetate is redox-neutral, the mechanism of this conversion is important to the overall energetics of the cyclohexanone production pathway. One enzyme for the conversion PEP to oxaloacetate is PEP carboxykinase which simultaneously forms an ATP while carboxylating PEP. In most organisms, however, PEP carboxykinase serves a gluconeogenic function and converts oxaloacetate to PEP at the expense of one ATP. *S. cerevisiae* is one such organism whose native PEP carboxykinase, PCK1, serves a gluconeogenic role (Valdes-Hevia et al., *FEBS Lett.* 258:313-316 (1989)). *E. coli* is another such organism, as the role of PEP carboxykinase in producing oxaloacetate is believed to be minor when compared to PEP carboxylase, which does not form ATP, possibly due to the higher $K_m$ for bicarbonate of PEP carboxykinase (Kim et al., *Appl. Environ Microbial.* 70:1238-1241 (2004)). Nevertheless, activity of the native *E. coli* PEP carboxykinase from PEP towards oxaloacetate has been recently demonstrated in ppc mutants of *E. coli* K-12 (Kwon et al., *J. Microbial. Biotechnol.* 16:1448-1452 (2006)). These strains exhibited no growth defects and had increased succinate production at high $NaHCO_3$ concentrations. In some organisms, particularly rumen bacteria, PEP carboxykinase is quite efficient in producing oxaloacetate from PEP and generating ATP. Examples of PEP carboxykinase genes that have been cloned into *E. coli* include those from *Mannheimia succiniciproducens* (Lee et al., *Biotechnol. Bioprocess. Eng.* 7:95-99 (2002)), *Anaerobiospirillum succiniciproducens* (Laivenieks et al., *Appl. Environ. Microbiol.* 63:2273-2280 (1997)), and *Actinobacillus succinogenes* (Kim et al., supra)). Internal experiments have also found that the PEP carboxykinase enzyme encoded by *Haemophilus influenza* is highly efficient at forming oxaloacetate from PEP. The protein sequences for exemplary gene products can be found using the following GenBank accession numbers shown below in Table 11.

TABLE 11

| Protein | GenBank ID | GI Number | Organism |
|---|---|---|---|
| PCK1 | NP_013023 | 6322950 | Saccharomyces cerevisiae |
| pck | NP_417862.1 | 16131280 | Escherichia coli |
| pckA | YP_089485.1 | 52426348 | Mannheimia succiniciproducens |
| pckA | O09460.1 | 3122621 | Anaerobiospirillum succiniciproducens |
| pckA | Q6W6X5 | 75440571 | Actinobacillus succinogenes |
| pckA | P43923.1 | 1172573 | Haemophilus influenza |

Pimeloyl-CoA is an intermediate of biotin biosynthesis. The enzymatic steps catalyzing biotin formation from pimeloyl-CoA are well-known and have been studied in several organisms, including *Escherichia coli, Bacillus subtilis* and *Bacillus sphaericus*, but pathways for synthesizing pimeloyl-CoA are not fully elucidated. In gram-negative bacteria such as *E. coli* the gene products of bioC and bioH are required for pimeloyl-CoA synthesis and strains deficient in these genes require addition of exogenous biotin to support growth (Del Campillo-Campbell et al., *J. Bacteriol.* 94:2065-2066 (1967)). The bioC gene product is thought to serve as a specific acyl-carrier protein catalyzing the stepwise condensation of malonyl-CoA units (Lemoine et al., *Mol. Microbiol.* 19:645-647 (1996)). The BioH protein contains a CoA binding site and is thought to function as an acyltransferase, shifting pimeloyl from BioC to CoA (Akatsuka et al., *Gene* 302: 185-192 (2003); Lemoine et al., supra)). A novel feature of BioC would then be to restrict the acyl-transfer to a starter malonyl-CoA unit, and to limit chain extension to two extender units (Lernoine et al., supra)). A $^{13}C$ labeling study in *E. coli* demonstrated that pimeloyl-CoA is derived from three acetate units and one unit of bicarbonate, implying that the synthetic mechanism is analogous to that of fatty acid and polyketide synthesis (Sanyai et al., *J. Am. Chem. Soc.* 116: 2637-2638 (1994)). Gram-positive bacteria, such as *B. subtilis* and *B. sphaericus*, utilize a different pathway for synthesizing pimeloyl-CoA from pimelate, but this pathway is also poorly understood. In all biotin-producing organisms, open questions remain about the exact metabolic transformations involved, the function of gene products in the biotin operon, the role of classical fatty acid biosynthetic complex(es), the nature of the carrier protein, and pathway regulation.

Fatty acid and polyketide synthesis pathways are well-understood. In the first step of fatty acid synthesis, acetyl-CoA carboxylase consumes one ATP equivalent to form malonyl-CoA from acetyl-CoA and bicarbonate (Barber et al., *Biochim. Biophys. Acta* 1733:1-28 (2005)). If the pimeloyl-CoA carbon skeleton is composed of 3 extender units of malonyl-CoA, as proposed by Lemoine (Lemoin et al., supra)), three ATP equivalents are required. If the other required enzymatic activities (malonyl-CoA acyltransferase, beta-ketoacyl synthase, beta-ketoacyl reductase, beta-hydroxyacyl dehydratase, and enoyl-CoA reductase) are catalyzed by enzymes analogous to the common fatty acid complex, the net reaction for synthesizing one mole of pimeloyl-CoA from 3 acetyl-CoA building blocks becomes:

3Acetyl-CoA+3ATP+4NADH+
Bicarbonate→Pimeloyl-CoA+4NAD$^+$+3ADP+
3Pi+2CoA+H$^+$

Such a pathway is costly from an energetic standpoint, and moreover is not able to achieve the maximum theoretical yield of cyclohexanone, in a strain containing the enzymatic activities to convert pimeloyl-CoA to cyclohexanone. Under anaerobic conditions this pathway is predicted to achieve a maximum yield of 0.7 moles of cyclohexanone per mole glucose utilized. As the pathway is energetically limited, no ATP is available to support cell growth and maintenance at the maximum product yield. These facts indicate that aerobic conditions are required to achieve high cyclohexanone yields via a pathway similar to fatty acid biosynthesis. Another potential challenge is that this pathway will face competition from the well-known fatty acid ACP for malonyl-CoA extender units.

Attempts to engineer biotin-overproducing strains have had moderate success, although the development of cost-effective strains remains a technical challenge (Streit et al., *Appl. Microbiol. Biotechnol.* 61:21-31 (2003)). Strategies applied to improve biotin production, such as mutagenesis, cloning and/or overexpression of genes involved in the early stages of pimeloyl-CoA synthesis, could also be applied to improve cyclohexanone production.

In accordance with some embodiments of the present invention, pimeloyl-CoA is synthesized from acetoacetyl-CoA in seven enzymatic steps as shown in FIG. 2. This pathway occurs naturally in some organisms that degrade benzoyl-CoA. Although this pathway normally operates in the degradative direction, there is evidence that the bacterium *Syntrophus aciditrophicus* is able to grow on crotonate as a carbon source and form pimeloyl-CoA, providing evidence that the enzymes in this pathway can operate in the synthetic direction (Mouttaki et al., supra).

In the pathway shown in FIG. 2, the 3-keto group of acetoacetyl-CoA is reduced and dehydrated to form crotonyl-CoA. Glutaryl-CoA is formed from the reductive carboxylation of crotonyl-CoA. A beta-ketothiolase then combines glutaryl-CoA with acetyl-CoA to form 3-oxopimeloyl-CoA. Reduction and dehydration yield the 2-enoyl-CoA, which is then reduced to pimeloyl-CoA.

The reduction of acetoacetyl-CoA to 3-hydroxybutyryl-CoA is catalyzed by 3-hydroxyacyl-CoA dehydrogenase, also called acetoacetyl-CoA reductase (EC 1.1.1.36). This enzyme participates in polyhydroxybutyrate biosynthesis in many organisms, and has also been used in metabolic engineering strategies for overproducing PHB and 3-hydroxyisobutyrate (Liu et al., *Appl. Microbiol. Biotechnol.* 76:811-818 (2007); Qui et al., *Appl. Microbiol. Biotechnol.* 69:537-542 (2006)). The enzyme from *Candida tropicalis* is a component of the peroxisomal fatty acid beta-oxidation multifunctional enzyme type 2 (MFE-2). The dehydrogenase B domain of this protein is catalytically active on acetoacetyl-CoA. The domain has been functionally expressed in *E. coli*, a crystal structure is available, and the catalytic mechanism is well-understood (Yliantilla et al., *J. Mol. Biol.* 358 1286-1295 (2006), Ylianttila et al., *Biochem. Biophys. Res. Commun.* 324:25-30 (2004)). Acetoacetyl-CoA reductase has also been studied for its role in acetate assimilation in *Rhodobacter sphaeroides* (Alber et al., *Mol. Microbiol.* 61:297-309 (2006)). The enzyme from *Zoogloea ramigera* has a very low Km for acetoacetyl-CoA and has been cloned and overproduced in *E. coli* (Ploux et al., *Eur J. Biochem.* 174:177-182 (1988)). The enzyme from *Paracoccus denitrificans* has been functionally expressed and characterized in *E. coli* (Yabutani et al., *FEMS Microbiol. Lett.* 133:85-90 (1995)). The protein sequences for exemplary gene products can be found using the following GenBank accession numbers shown below in Table 11.

TABLE 11

| Protein | GenBank ID | GI Number | Organism |
|---|---|---|---|
| Fox2 | Q02207 | 399508 | Candida tropicalis |
| phaB | YP_353825 | 77464321 | Rhodobacter sphaeroides |
| phbB | P23238 | 130017 | Zoogloea ramigera |
| phaB | BAA08358 | 675524 | Paracoccus denitrificans |

The conversion of acetoacetyl-CoA to 3-hydroxybutyryl-CoA can also be catalyzed by acetoacetyl-CoA reductase, also known as 3-hydroxyacyl dehydrogenase (EC 1.1.1.35). Exemplary enzymes include hbd from *C. acetobutylicum* (Boynton et al., *J. Bacteriol.* 178:3015-3024 (1996)), hbd from *C. beijerinckii* (Colby et al., *Appl. Environ Microbiol.* 58:3297-3302 (1992)) and a number of similar enzymes from *Metallosphaera sedula* (Berg et al., *Science* 318:1782-1786 (2007)). Additional genes include Hbd1 (C-terminal domain) and Hbd2 (N-terminal domain) in *Clostridium kluyveri* (Hillmer et al., *FEBS Lett.* 21:351-354 (1972)) and HSD17B10 in *Bos Laurus* (Wakil et al., *J. Biol. Chem.* 207:631-638 (1954)). The protein sequences for exemplary gene products can be found using the following GenBank accession numbers shown below in Table 12.

TABLE 12

| Protein | GenBank ID | GI Number | Organism |
|---|---|---|---|
| hbd | NP_349314.1 | 15895965 | Clostridium acetobutylicum |
| hbd | AAM14586.1 | 20162442 | Clostridium beijerinckii |
| Msed_1423 | YP_001191505 | 146304189 | Metallosphaera sedula |
| Msed_0399 | YP_001190500 | 146303184 | Metallosphaera sedula |
| Msed_0389 | YP_001190490 | 146303174 | Metallosphaera sedula |
| Msed_1993 | YP_001192057 | 146304741 | Metallosphaera sedula |
| Hbd2 | EDK34807.1 | 146348271 | Clostridium kluyveri |
| Hbd1 | EDK32512.1 | 146345976 | Clostridium kluyveri |
| HSD17B10 | O02691.3 | 3183024 | Bos taurus |

The gene product of pimF in *Rhodopseudomonas palustris*, predicted to encode a 3-hydroxy-acyl-CoA dehydratase, can also function as a 3-hydroxyacyl-CoA dehydrogenase during pimeloyl-CoA degradation (Harrison et al., *Microbiology* 151:727-736 (2005)). The gene product of fadB catalyzes these two functions during fatty acid beta-oxidation in *E. coli* (Yang et al., *Biochem.* 30:6788-6795 (1991)). 3-Hydroxyacyl-CoA dehydrogenase genes in *S. aciditrophicus*, inferred by sequence homology and genomic context, include syn_01310 and syn_01680 (McInerney et al., *Proc. Natl. Acad. Sci. U.S.A.* 104:7600-7605 (2007)). The protein sequences for exemplary gene products can be found using the following GenBank accession numbers shown below in Table 13.

TABLE 13

| Protein | GenBank ID | GI Number | Organism |
|---|---|---|---|
| pimF | CAE29158 | 39650635 | Rhodopseudomonas palustris |
| fadB | P21177 | 119811 | Escherichia coli |
| syn_01310 | YP_461961 | 85859759 | Syntrophus aciditrophicus |
| syn_01680 | ABC78882 | 85723939 | Syntrophus aciditrophicus |

3-Hydroxybutyryl-CoA dehydratase (EC 4.2.1.55), also called crotonase, dehydrates 3-hydroxyisobutyryl-CoA to form crotonoyl-CoA (FIG. 3, step 2). Crotonase enzymes are required for n-butanol formation in some organisms, particularly *Clostridial* species, and also comprise one step of the 3-hydroxypropionate/4-hydroxybutyrate cycle in thermoacidophilic Archaea of the genera *Sulfolobus*, *Acidianus*, and *Metallosphaera*. Exemplary genes encoding crotonase enzymes can be found in *C. acetobutylicum* (Atsumi et al., *Metab. Eng.* 10:305-311 (2007); Boynton et al., supra), *C. kluyveri* (Hillmer et al., supra), and *Metallosphaera sedula* (Berg et al., supra). The gene product of pimF in *Rhodopseudomonas palustris* is predicted to encode a 3-hydroxy-acyl-CoA dehydratase that participates in pimeloyl-CoA degradation (Harrison et al., *Microbiol.* 151:727-736 (2005)). A number of genes in *S. aciditrophicus* were identified by sequence similarity to the 3-hydroxybutyryl-CoA dehydratases of *C. acetobutylicum* and *C. kluyveri*. The protein sequences for exemplary gene products can be found using the following GenBank accession numbers shown below in Table 14.

TABLE 14

| Protein | GenBank ID | GI Number | Organism |
|---|---|---|---|
| crt | NP_349318.1 | 15895969 | Clostridium acetobutylicum |
| crt1 | YP_001393856.1 | 153953091 | Clostridium kluyveri |
| pimF | CAE29158 | 39650635 | Rhodopseudomonas palustris |
| syn_01309 | YP_461962 | 85859760 | Syntrophus aciditrophicus |
| syn_01653 | YP_463074 | 85860872 | Syntrophus aciditrophicus |
| syn_01654 | YP_463073.1 | 85860871 | Syntrophus aciditrophicus |
| syn_02400 | YP_462924.1 | 85860722 | Syntrophus aciditrophicus |
| syn_03076 | YP_463074.1 | 85860872 | Syntrophus aciditrophicus |

Enoyl-CoA hydratases (EC 4.2.1.17) also catalyze the dehydration of 3-hydroxyacyl-CoA substrates (Agnihotri et al., *Bioorg. Med. Chem.* 11:9-20 (2003); Conrad et al., *J. Bacteriol.* 118:103-111 (1974); Roberts et al., *Arch. Microbiol.* 117:99-108 (1978)). The enoyl-CoA hydratase of *Pseudomonas putida*, encoded by ech, catalyzes the conversion of 3-hydroxybutyryl-CoA to crotonyl-CoA (Roberts et al., supra). Additional enoyl-CoA hydratases are phaA and phaB, of *P. putida*, and paaA and paaB from *P. fluorescens* (Olivera et al., *Proc. Natl. Acad. Sci.* 95:6419-6424 (1998)). Lastly, a number of *Escherichia coli* genes have been shown to demonstrate enoyl-CoA hydratase functionality including maoC (Park et al., *J. Bacteriol.* 185:5391-5397 (2003)), puaF (Ismail et al., *Eur. J. Biochem.* 270:3047-3054 (2003); Park et al., *Appl. Biochem. Biotechnol.* 113:335-346 (2004); Park et al., *Biotechnol. Bioeng.* 86:681-686 (2004)) and paaG (Ismail et al, supra; Park et al., (2003) supra; Park et al., (2004) supra)). The protein sequences for exemplary gene products can be found using the following GenBank accession numbers shown below in Table 15.

TABLE 15

| Protein | GenBank ID | GI Number | Organism |
|---|---|---|---|
| ech | NP_745498.1 | 26990073 | Pseudomonas putida |
| phaA | NP_745427.1 | 26990002 | Pseudomonas putida |
| phaB | NP_745426.1 | 26990001 | Pseudomonas putida |
| paaA | ABF82233.1 | 106636093 | Pseudomonas fluorescens |
| paaB | ABF82234.1 | 106636094 | Pseudomonas fluorescens |
| maoC | NP_415905.1 | 16129348 | Escherichia coli |
| paaF | NP_415911.1 | 16129354 | Escherichia coli |
| paaG | NP_415912.1 | 16129355 | Escherichia coli |

Alternatively, the *E. coli* gene products of fadA and fadB encode a multienzyme complex involved in fatty acid oxidation that exhibits enoyl-CoA hydratase activity (Nakahigashi et al., *Nucleic Acids Res.* 18:4937 (1990); Yang, s. Y. *J. Bacteriol.* 173:7405-7406 (1991); Yang et al., *Biochemistry* 30:6788-6795 (1991)). Knocking out a negative regulator encoded byfadR can be utilized to activate the fadB gene product (Sato et al., *J. Biosci. Bioeng.* 103:38-44 (2007)). The fadI and fadJ genes encode similar functions and are naturally expressed under anaerobic conditions (Campbell et al., *Mol. Microbiol.* 47:793-805 (2003)). The protein sequences for exemplary gene products can be found using the following GenBank accession numbers shown below in Table 16.

TABLE 16

| Protein | GenBank ID | GI Number | Organism |
| --- | --- | --- | --- |
| fadA | YP_026272.1 | 49176430 | *Escherichia coli* |
| fadB | NP_418288.1 | 16131692 | *Escherichia coli* |
| fadI | NP_416844.1 | 16130275 | *Escherichia coli* |
| fadJ | NP_416843.1 | 16130274 | *Escherichia coli* |
| fadR | NP_415705.1 | 16129150 | *Escherichia coli* |

Glutaryl-CoA dehydrogenase (GCD, EC 1.3.99.7 and EC 4.1.1.70) is a bifunctional enzyme that catalyzes the oxidative decarboxylation of glutaryl-CoA to crotonyl-CoA (FIG. 3, step 3). Bifunctional GCD enzymes are homotetramers that utilize electron transfer flavoprotein as an electron acceptor (Hartel et al., *Arch. Microbiol.* 159:174-181 (1993)). Such enzymes were first characterized in cell extracts of *Pseudomonas* strains KB740 and K172 during growth on aromatic compounds (Hartel et al., supra), but the associated genes in these organisms is unknown. Genes encoding glutaryl-CoA dehydrogenase (gcdH) and its cognate transcriptional regulator (gcdR) were identified in *Azoarcus* sp. CIB (Blazquez et al., *Environ. Microbiol.* 10:474-482 (2008)). An *Azoarcus* strain deficient in gcdH activity was used to identify the a heterologous gene gcdH from *Pseudomonas putida* (Blazquez et al, supra). The cognate transcriptional regulator in *Pseudomonas putida* has not been identified but the locus PP_0157 has a high sequence homology (>69% identity) to the *Azoarcus* enzyme. Additional GCD enzymes are found in *Pseudomonas fluorescens* and *Paracoccus denitrificans* (Husain et al., *J. Bacteriol.* 163:709-715 (1985)). The human GCD has been extensively studied, overexpressed in *E. coli* (Dwyer et al., *Biochemistry* 39:11488-11499 (2000)), crystallized, and the catalytic mechanism involving a conserved glutamate residue in the active site has been described (Fu et al., *Biochemistry* 43:9674-9684 (2004)). A GCD in *Syntrophus aciditrophicus* operates in the $CO_2$-assimilating direction during growth on crotonate (Mouttaki et al., supra)). Two GCD genes in *S. aciditrophicus* were identified by protein sequence homology to the *Azoarcus* GcdH: syn_00480 (3 %) and syn_01146 (31%). No significant homology was found to the *Azoarcus* GcdR regulatory protein. The protein sequences for exemplary gene products can be found using the following GenBank accession numbers shown below in Table 17.

TABLE 17

| Protein | GenBank ID | GI Number | Organism |
| --- | --- | --- | --- |
| gcdH | ABM69268.1 | 123187384 | *Azoarcus* sp. CIB |
| gcdR | ABM69269.1 | 123187385 | *Azoarcus* sp. CIB |
| gcdH | AAN65791.1 | 24981507 | *Pseudomonas putida* KT2440 |
| PP_0157 (gcdR) | AAN65790.1 | 24981506 | *Pseudomonas putida* KT2440 |
| gcdH | YP_257269.1 | 70733629 | *Pseudomonas fluorescens* Pf-5 |

TABLE 17-continued

| Protein | GenBank ID | GI Number | Organism |
| --- | --- | --- | --- |
| gcvA (gcdR) | YP_257268.1 | 70733628 | *Pseudomonas fluorescens* Pf-5 |
| gcd | YP_918172.1 | 119387117 | *Paracoccus denitrificans* |
| gcdR | YP_918173.1 | 119387118 | *Paracoccus denitrificans* |
| gcd | AAH02579.1 | 12803505 | *Homo sapiens* |
| syn_00480 | ABC77899 | 85722956 | *Syntrophus aciditrophicus* |
| syn_01146 | ABC76260 | 85721317 | *Syntrophus aciditrophicus* |

Alternatively, the carboxylation of crotonyl-CoA to glutaconyl-CoA and subsequent reduction to glutaryl-CoA can be catalyzed by separate enzymes: glutaconyl-CoA decarboxylase and glutaconyl-CoA reductase. Glutaconyl-CoA decarboxylase enzymes, characterized in glutamate-fermenting anaerobic bacteria, are sodium-ion translocating decarboxylases that utilize biotin as a cofactor and are composed of four subunits (alpha, beta, gamma, and delta) (Boiangiu et al., *J. Mol. Microbiol. Biotechnol.* 10:105-119 (2005); Buckel et al., *Biochim. Biophys. Acta* 1505:15-27 (2001)). Such enzymes have been characterized in *Fusobacterium nucleatum* (Beatrix et al., *Arch. Microbiol.* 154:362-369 (1990)) and *Acidaminococcus fermentans* (Braune et al., *Mol. Microbiol.* 31:473-487 (1999)). Analogs to the *F. nucleatum* glutaconyl-CoA decarboxylase alpha, beta and delta subunits are found in *S. aciditrophicus*. A gene annotated as an enoyl-CoA dehydrogenase, syn_00480, another GCD, is located in a predicted operon between a biotin-carboxyl carrier (syn_00479) and a glutaconyl-CoA decarboxylase alpha subunit (syn_00481). The protein sequences for exemplary gene products can be found using the following GenBank accession numbers shown below in Table 18.

TABLE 18

| Protein | GenBank ID | GI Number | Organism |
| --- | --- | --- | --- |
| gcdA | CAA49210 | 49182 | *Acidaminococcus fermentans* |
| gcdC | AAC69172 | 3777506 | *Acidaminococcus fermentans* |
| gcdD | AAC69171 | 3777505 | *Acidaminococcus fermentans* |
| gcdB | AAC69173 | 3777507 | *Acidaminococcus fermentans* |
| FN0200 | AAL94406 | 19713641 | *Fusobacterium nucleatum* |
| FN0201 | AAL94407 | 19713642 | *Fusobacterium nucleatum* |
| FN0204 | AAL94410 | 19713645 | *Fusobacterium nucleatum* |
| syn_00479 | YP_462066 | 85859864 | *Syntrophus aciditrophicus* |
| syn_00481 | YP_462068 | 85859866 | *Syntrophus aciditrophicus* |
| syn_01431 | YP_460282 | 85858080 | *Syntrophus aciditrophicus* |
| syn_00480 | ABC77899 | 85722956 | *Syntrophus aciditrophicus* |

If glutaconyl-CoA is formed by an enzyme with crotonyl-CoA carboxylase activity, reduction of glutaconyl-CoA to glutaryl-CoA can be accomplished by an enzyme with glutaconyl-CoA reductase activity. Enoyl-CoA reductase enzymes for catalyzing the reduction of 6-carboxyhex-2-enoyl-CoA to pimeloyl-CoA, described below, are also applicable here. One enzyme for this step is syn_00480 of *S. aciditrophicus*, due to its genomic context adjacent to genes predicted to catalyze related functions.

Glutaryl-CoA and acetyl-CoA are condensed to form 3-oxopimeloyl-CoA by oxopimeloyl-CoA:glutaryl-CoA acyltransferase, a beta-ketothiolase (EC 2.3.1.16). An enzyme catalyzing this transformation is found in *Ralstonia eutropha* (formerly known as *Alcaligenes eutrophus*), encoded by genes bktB and bktC (Haywood et al., *FEMS Microbiol. Lett.* 52:91-96 (1988); Slater et al., *J. Bacteriol.* 180:1979-1987 (1998)). The sequence of the BktB protein is known; however, the sequence of the BktC protein has not been reported. The pim operon of *Rhodopseudomonas palustris* also encodes a beta-ketothiolase, encoded by pimB, predicted to catalyze this transformation in the degradative direction during benzoyl-CoA degradation (Harrison et al., supra). A beta-ketothiolase enzyme in *S. aciditrophicus* was identified by sequence homology to bktB (43% identity, evalue=1e-93). The protein sequences for exemplary gene products can be found using the following GenBank accession numbers shown below in Table 19.

TABLE 19

| Protein | GenBank ID | GI Number | Organism |
|---|---|---|---|
| bktB | YP_725948 | 11386745 | *Ralstonia eutropha* |
| pimB | CAE29156 | 39650633 | *Rhodopseudomonas palustris* |
| syn_02642 | YP_462685.1 | 85860483 | *Syntrophus aciditrophicus* |

Beta-ketothiolase enzymes catalyzing the formation of beta-ketovalerate from acetyl-CoA and propionyl-CoA can also catalyze the formation of 3-oxopimeloyl-CoA. *Zoogloea ramigera* possesses two ketothiolases that can form beta-ketovaleryl-CoA from propionyl-CoA and acetyl-CoA and *R. eutropha* has a beta-oxidation ketothiolase that is also capable of catalyzing this transformation (Gruys et al., U.S. Pat. No. 5,958,745). The sequences of these genes or their translated proteins have not been reported, but several genes in *R. eutropha*, *Z. ramigera*, or other organisms can be identified based on sequence homology to bktB from *R. eutropha*. The protein sequences for exemplary gene products can be found using the following GenBank accession numbers shown below in Table 20.

TABLE 20

| Protein | GenBank ID | GI Number | Organism |
|---|---|---|---|
| phaA | YP_725941.1 | 113867452 | *Ralstonia eutropha* |
| h16_A1713 | YP_726205.1 | 113867716 | *Ralstonia eutropha* |
| pcaF | YP_728366.1 | 116694155 | *Ralstonia eutropha* |
| h16_B1369 | YP_840888.1 | 116695312 | *Ralstonia eutropha* |
| h16_A0170 | YP_724690.1 | 113866201 | *Ralstonia eutropha* |
| h16_A0462 | YP_724980.1 | 113866491 | *Ralstonia eutropha* |
| h16_A1528 | YP_726028.1 | 113867539 | *Ralstonia eutropha* |
| h16_B0381 | YP_728545.1 | 116694334 | *Ralstonia eutropha* |
| h16_B0662 | YP_728824.1 | 116694613 | *Ralstonia eutropha* |
| h16_B0759 | YP_728921.1 | 116694710 | *Ralstonia eutropha* |
| h16_B0668 | YP_728830.1 | 116694619 | *Ralstonia eutropha* |
| h16_A1720 | YP_726212.1 | 113867723 | *Ralstonia eutropha* |
| h16_A1887 | YP_726356.1 | 113867867 | *Ralstonia eutropha* |
| phbA | P07097.4 | 135759 | *Zoogloea ramigera* |
| bktB | YP_002005382.1 | 194289475 | *Cupriavidus taiwanensis* |
| Rmet_1362 | YP_583514.1 | 94310304 | *Ralstonia metallidurans* |
| Bphy_0975 | YP_001857210.1 | 186475740 | *Burkholderia phymatum* |

Additional enzymes include beta-ketothiolases that are known to convert two molecules of acetyl-CoA into acetoacetyl-CoA (EC 2.1.3.9). Exemplary acetoacetyl-CoA thiolase enzymes include the gene products of atoB from *E. coli* (Martin et al., *Nat. Biotechnol.* 21:796-802 (2003)), thlA and thlB from *C. acetobutylicum* (Hanai et al., *Appl. Environ. Microbiol.* 73:7814-7818 (2007); Winzer et al., *J. Mol. Microbiol. Biotechnol.* 2:531-541 (2000)), and ERG10 from *S. cerevisiae* (Hiser et al., *J. Biol. Chem.* 269:31383-31389 (1994)). The protein sequences for exemplary gene products can be found using the following GenBank accession numbers shown below in Table 21.

TABLE 21

| Protein | GenBank ID | GI Number | Organism |
|---|---|---|---|
| atoB | NP_416728 | 16130161 | *Escherichia coli* |
| thlA | NP_349476.1 | 15896127 | *Clostridium acetobutylicum* |
| thlB | NP_149242.1 | 15004782 | *Clostridium acetobutylicum* |
| ERG10 | NP_015297 | 6325229 | *Saccharomyces cerevisiae* |

Beta-ketoadipyl-CoA thiolase (EC 2.3.1.174), also called 3-oxoadipyl-CoA thiolase, converts beta-ketoadipyl-CoA to succinyl-CoA and acetyl-CoA, and is a key enzyme of the beta-ketoadipate pathway for aromatic compound degradation. The enzyme is widespread in soil bacteria and fungi including *Pseudomonas putida* (Harwood et al., *Bacteriol.* 176-6479-6488 (1994)) and *Acinetobacter calcoaceticus* (Doten et al., *J. Bacteriol.* 169:3168-3174 (1987)). The *P. putida* enzyme is a homotetramer bearing 45% sequence homology to beta-ketothiolases involved in PHB synthesis in *Ralstonia eutropha*, fatty acid degradation by human mitochondria and butyrate production by *Clostridium acetobutylicum* (Harwood et al., supra). A beta-ketoadipyl-CoA thiolase in *Pseudomonas knackmussii* (formerly sp. B13) has also been characterized (Gobel et al., *J. Bacteriol.* 184:216-223 (2002); Kaschabek et al., supra). The protein sequences for exemplary gene products can be found using the following GenBank accession numbers shown below in Table 22.

TABLE 22

| Protein | GenBank ID | GI Number | Organism |
|---|---|---|---|
| pcaF | NP_743536.1 | 506695 | *Pseudomonas putida* |
| pcaF | AAC37148.1 | 141777 | *Acinetobacter calcoaceticus* |
| catF | Q8VPF1.1 | 75404581 | *Pseudomonas knackmussii* |

Reduction of 3-oxopimeloyl-CoA to 3-hydroxypimeloyl-CoA is catalyzed by 3-hydroxypimeloyl-CoA dehydrogenase (EC 1.1.1.259). This activity has been demonstrated in cell extracts of *Rhodopseudomonas palustris* and *Pseudomonas* sp (Koch et al., *Eur. J. Biochem.* 211:649-661 (1993); Koch et al., *Eur. J. Biochem.* 205:195-202 (1992)) but genes have not been reported. This transformation is also predicted to occur in *Syntrophus aciditrophicus* during growth on crotonate (Mouttaki et al., supra). Enzymes with 3-hydroxyacyl-CoA dehydrogenase and/or acetoacetyl-CoA reductase activities can also catalyze this reaction.

Dehydration of 3-hydroxypimeloyl-CoA to 6-carboxyhex-2-enoyl-CoA is predicted to occur in *S. aciditrophicus* during crotonate utilization to cyclohexane carboxylate (Mouttaki et al., supra). This reaction can be catalyzed by an enoyl-CoA hydratase (4.2.1.17) or a 3-hydroxybutyryl-CoA dehydratase (EC 4.2.1.55).

The reduction of 6-carboxyhex-2-enoyl-CoA to pimeloyl-CoA by pimeloyl-CoA dehydrogenase (EC 1.3.1.62) has been characterized in *Syntrophus aciditrophicus* cell extracts (Elshahed et al., supra). Enoyl-CoA reductase enzymes are suitable enzymes for catalyzing this transformation. One exemplary enoyl-CoA reductase is the gene product of bcd from *C. acetobutylicum* (Atsumi et al., supra; Boynton et al., supra), which naturally catalyzes the reduction of crotonyl-CoA to butyryl-CoA. Activity of this enzyme can be enhanced by expressing bcd in conjunction with expression of the *C. acetobutylicum* etfAB genes, which encode an electron transfer flavoprotein. An additional enzyme for the enoyl-CoA reductase step is the mitochondrial enoyl-CoA reductase from *E. gracilis* (Hoffmeister et al., *J. Biol. Chem.* 280:4329-4338 (2005)). A construct derived from this sequence following the removal of its mitochondrial targeting leader sequence was cloned in *E. coli* resulting in an active enzyme (Hoffmeister et al., supra). This approach is well known to those skilled in the art of expressing eukaryotic genes, particularly those with leader sequences that can target the gene product to a specific intracellular compartment, in prokaryotic organisms. A close homolog of this gene, TDE0597, from the prokaryote *Treponema denticola* represents a third enoyl-CoA reductase which has been cloned and expressed in *E. coli* (Tucci et al. *FEBS Lett.* 581:1561-1566 (2007)). Six genes in *S. aciditrophicus* were identified by sequence homology to the *C. acetobutylicum* bcd gene product. The *S. aciditrophicus* genes syn_02637 and syn_02636 bear high sequence homology to the etfAB genes of *C. acetobutylicum*, and are predicted to encode the alpha and beta subunits of an electron transfer flavoprotein. The protein sequences for exemplary gene products can be found using the following GenBank accession numbers shown below in Table 23.

TABLE 23

| Protein | GenBank ID | GI Number | Organism |
|---|---|---|---|
| bcd | NP_349317.1 | 15895968 | *Clostridium acetobutylicum* |
| etfA | NP_49315.1 | 15895966 | *Clostridium acetobutylicum* |
| etfB | NP_349316.1 | 15895967 | *Clostridium acetobutylicum* |
| TER | Q5EU90.1 | 62287512 | *Euglena gracilis* |
| TDE0597 | NP_971211.1 | 42526113 | *Treponema denticola* |
| syn_02587 | ABC76101 | 85721158 | *Syntrophus aciditrophicus* |
| syn_02586 | ABC76100 | 85721157 | *Syntrophus aciditrophicus* |
| syn_01146 | ABC76260 | 85721317 | *Syntrophus aciditrophicus* |
| syn_00480 | ABC77899 | 85722956 | *Syntrophus aciditrophicus* |
| syn_02128 | ABC76949 | 85722006 | *Syntrophus aciditrophicus* |
| syn_01699 | ABC78863 | 85723920 | *Syntrophus aciditrophicus* |
| syn_02637 | ABC78522.1 | 85723579 | *Syntrophus aciditrophicus* |
| syn_02636 | ABC78523.1 | 85723580 | *Syntrophus aciditrophicus* |

Additional enoyl-CoA reductase enzymes are found in organisms that degrade aromatic compounds. *Rhodopseudomonas palustris*, a model organism for benzoate degradation, has the enzymatic capability to degrade pimelate via beta-oxidation of pimeloyl-CoA. Adjacent genes in the pim operon, pimC and pimD, bear sequence homology to *C. acetobutylicum* bcd and are predicted to encode a flavin-containing pimeloyl-CoA dehydrogenase (Harrison et al., supra). The genome of nitrogen-fixing soybean symbiont *Bradyrhizobium japonicum* also contains a pim operon composed of genes with high sequence similarity to pimC and pimD of *R. palustris* (Harrison et al., supra). The protein sequences for exemplary gene products can be found using the following GenBank accession numbers shown below in Table 24.

TABLE 24

| Protein | GenBank ID | GI Number | Organism |
|---|---|---|---|
| pimC | CAE29155 | 39650632 | *Rhodopseudomonas palustris* |
| pimD | CAE29154 | 39650631 | *Rhodopseudomonas palustris* |
| pimC | BAC53083 | 27356102 | *Bradyrhizobium japonicum* |
| pimD | BAC53082 | 27356101 | *Bradyrhizobium japonicum* |

An additional enzyme is 2-methyl-branched chain enoyl-CoA reductase (EC 1.3.1.52), an enzyme catalyzing the reduction of sterically hindered trans-enoyl-CoA substrates. This enzyme participates in branched-chain fatty acid synthesis in the nematode *Ascarius scum* and is capable of reducing a variety of linear and branched chain substrates including 2-methylbutanoyl-CoA, 2-methylpentanoyl-CoA, octanoyl-CoA and pentanoyl-CoA (Duran et al., *J. Biol. Chem.* 268: 22391-22396 (1993)). Two isoforms of the enzyme, encoded by genes acad1 and acad, have been characterized. The protein sequences for exemplary gene products can be found using the following GenBank accession numbers shown below in Table 25.

TABLE 25

| Protein | GenBank ID | GI Number | Organism |
|---|---|---|---|
| acad1 | AAC48316.1 | 2407655 | *Ascarius suum* |
| acad | AAA16096.1 | 347404 | *Ascarius suum* |

Alternative routes for producing a cyclic compound from 3-hydroxypimeloyl-CoA that do not proceed through pimeloyl-CoA are shown in FIG. 3. This route is found in *Geobacter metallireducens* and *Thauera aromatica*, among others, in the direction of beta-oxidation. In the route, the biosynthesis of 3-hydroxypimelyl-CoA proceeds from acetoacetyl-CoA, as described above. 3-Hydroxypimeloyl-CoA is dehydrated to form a cyclic product, 6-oxocyclohex-1-ene-1-carboxyl-CoA (6-KCH-CoA). 6-KCH-CoA is then converted to cyclohexanone in three enzymatic steps: removal of the CoA moiety, decarboxylation and reduction. With a reversible PEP carboxykinase, this pathway is predicted to achieve a theoretical yield of cyclohexanone (0.75 mol/mol) and is able to achieve an ATP yield of 0.56 mol/mol if a transferase or ATP synthase is utilized in step 2.

6-KCH-CoA hydrolase (EC 3.7.1.-) converts 6-ketocyclohex-1-ene-1-carboxyl-CoA (6-KCH-CoA) to 3-hydroxypimeloyl-CoA. This enzyme belongs to the crotonase superfamily and is unusual in that it incorporates two water molecules in the ring-opening direction (Eberhard et al., *J. Am. Chem. Soc.* 126:7188-7189 (2004)). This enzyme has been studied in the context of anaerobic benzoyl-CoA degradation in the obligate anaerobes *Thauera aromatica* (Breese et al., *Eur. J. Biochem.* 256:148-154 (1998), Laempe et al., *Eur. J. Biochem.* 263:420-429 (1999)), *Geobacter metallireducens* (Kuntze et al., *Environ Microbiol.* 10:1547-1556 (2008)), *S. aciditrophicus* (Kuntze et al., supra), *Azoarcus evansii* (Harwood et al., *FEBS Microbiol. Rev.* 22:439-458 (1999)) and *Azoarcus* sp. Strain CIB (Lopez-Barragan et al., *Bacteriol.* 186:5762-5774 (2004)). The 6-KCH-CoA hydrolase genes gmet_2088 from *G. metallireducens* and syn_01654 from *S. aciditrophicus* were heterologously expressed and characterized in *E. coli* (Kuntze et al. supra). The *S. aciditrophicus* 6-KCH-CoA hydrolase (syn_01654) was assayed for activity in the ring-closing direction but this activity was not observed (Kuntze et al., supra). Additional genes encoding 6-KCH-CoA hydrolases were identified in *Desulfococcus multivorans* and an m-xylene degrading enrichment culture (Kuntze et al., supra). Additional hydrolases in *S. aciditrophicus* are syn_01653, syn_02400, syn_03076 and syn_01309. Syn_01653 is adjacent to syn_01654 and predicted to be in the same operon. The protein sequences for exemplary gene products can be found using the following GenBank accession numbers shown below in Table 26.

TABLE 26

| Protein | GenBank ID | GI Number | Organism |
|---|---|---|---|
| bzdY | AAQ08817.1 | 33326786 | *Azoarcus* sp. CIB |
| bzdY | CAD21638.1 | 18369665 | *Azoarcus evansii* |
| oah | CAA12245.1 | 3724166 | *Thauera aromatica* |
| bamA (gmet_2088) | YP_385042.1 | 78223295 | *Geobacter metallireducens* |

TABLE 26-continued

| Protein | GenBank ID | GI Number | Organism |
|---|---|---|---|
| bamA (syn_01654) | YP_463073.1 | 85860871 | Syntrophus aciditrophicus |
| N/A | ABY89672.2 | 262284543 | Desulfococcus multivorans |
| N/A | ABY89673.1 | 166798254 | [bacterium enrichment culture clone ZzG1mX] |
| syn_01653 | YP_463074.1 | 85860872 | Syntrophus aciditrophicus |
| syn_02400 | YP_462924,1 | 85860722 | Syntrophus aciditrophicus |
| syn_03076 | YP_463118.1 | 85860916 | Syntrophus aciditrophicus |
| syn_01309 | YP_461962.1 | 85859760 | Syntrophus aciditrophicus |

The de-acylation of 6-KCH-CoA is similar to the de-acylation of 2-ketocyclohexane-1-carboxyl-CoA (2-KCH-CoA) to 2-ketocyclohexane-1-carboxylate (2-KCH) by a CoA-transferase, synthetase or hydrolase. Exemplary enzymes include those discussed above. The decarboxylation of 6-KCH to 2-cyclohexenone (step 3) is similar to the decarboxylation of 2-KCH (FIG. 1, step 3 and FIG. 3, step 7). Exemplary enzymes for that transformation are also applicable here.

In the final step of the pathway, 2-cyclohexen-1-one is reduced to form cyclohexanone by cyclohexanone dehydrogenase (EC 1.3.99.14), an NAD(P)H-dependent enone reductase. This reaction occurs in cell extracts of the denitrifying bacteria *Alicycliphilus denitrilicans* sp. K601 (formerly known as *Pseudomonas* sp. K601) during anaerobic growth on cyclohexanol (Dangel et al., *Arch. Microbiol.* 152:271-279; Dangel et al., *Arch. Microbiol.* 150:358-362 (1988); Mechichi et al., *In. J. Syst. Evol. Mcrobiol.* 53:147-152 (2003)). Purified cyclohexanone dehydrogenase was characterized in cell extracts.

Enzymes with enone reductase activity that naturally react with cyclic compounds have been identified in prokaryotes, eukaryotes and plants (Shimoda et al., *Bulletin of the Chemical Society of Japan* 77:2269-2 (2004); Wanner et al., *Eur. J. Biochem.* 255:271-278 (1998)). Two enone reductases from the cytosolic fraction of *Saccharomyces cerevisiae* were purified and characterized, and found to accept 2-cyclohexen-1-one as a substrate (Wanner et al., supra). Cell extracts of cyanobacterium *Synechococcus* sp. PCC7942 reduced a variety of cyclic and acyclic substrates, including 2-methyl-2-cyclohexen-1-one and 2-ethyl-2-cyclohexen-1-one, to their corresponding alkyl ketones (Shimoda et al., supra). Genes have not been associated with these activities. A recombinant NADPH-dependent enone reductase from *Nicotiana tabacum*, encoded by NtRed1, was functionally expressed and characterized in *E. coli* (Matsushima et al., *Bioorganic Chemistry* 36:23-28 (2008)). This reductase was functional on exocyclic enoyl ketones but did not react with carvone, a sterically hindered endocyclic enoyl ketone (Matsushima et al., supra). This enzyme was not tested on 2-cyclohexen-1-one as a substrate. An enzyme in *S. cerevisiae* at the locus YML131W, bears 30% identity to NtRed1 (evalue=1e-26). Endocyclic enoate reductase activity has also been detected in *N. tabacum* (Hirata et al., *Phytochemistry* 28:3331-3333 (1989)). The amino acid sequence of NiRed1 shares significant homology with 2-alkenal reductase from *Arabidopsis thaliana*, zeta-crystallin homolog from *A. thaliana*, pulegone reductase from *Menthe piperita* and phenylpropenal double bond reductase from *Pinus taeda*. These enzymes are known to catalyze the reduction of alkenes of α,β-unsaturated ketones or aldehydes. The protein sequences for exemplary gene products can be found using the following GenBank accession numbers shown below in Table 27.

TABLE 27

| Protein | GenBank ID | GI Number | Organism |
|---|---|---|---|
| NtRed1 | BAA89423 | 6692816 | Nicotiana tabacum |
| AtDBR1 | NP_197199 | 15237888 | Arabidopsis thaliana |
| P2 | CAA89262 | 886430 | Arabidopsis thaliana |
| PulR | AAQ75423 | 34559418 | Menthe piperita |
| PtPPDBR | ABG91753 | 110816011 | Pinus taeda |
| YML131W | AAS56318.1 | 45269874 | Saccharomyces cerevisiae |

Another endocyclic enone reductase is (−)-isopiperitenone reductase (IspR), an enzyme participating in monoterpene biosynthesis in *Menthe piperita* (Ringer et al., *Arch. Biochem. Biophys* 418:80-92 (2003)). The protein sequence of this enzyme shows significant homology to putative short-chain reductases in human, pig, CHO-K1/hamster cells and *Arabidopsis thaliana* (Ringer et al., supra). The *M. piperita* IspR protein sequence was compared to the *S. cerevisiae* and *Synechococcus* sp. PCC 7942 genomes, but no high-confidence hits were identified. The closest was a putative benzil reductase in *S. cerevisiae* at the locus YIR036c bearing 26% identity to IspR. The protein sequences for exemplary gene products can be found using the following GenBank accession numbers shown below in Table 28.

TABLE 28

| Protein | GenBank ID | GI Number | Organism |
|---|---|---|---|
| ispR | AAQ75422.1 | 34559416 | Menthe piperita |
| AT3G61220 | NP_191681.1 | 15233062 | Arabidopsis thaliana |
| cbr | NP_001748.1 | 4502599 | Homo sapiens |
| CBR1 | NP_999238.1 | 47522960 | Sus scrofa |
| CHO-CR | BAB07797.1 | 9711233 | Cricetulus griseus |
| YIR036C | NP_012302.1 | 6322227 | Saccharomyces cerevisiae |

Enzymes with 2-enoate reductase activity (EC 1.3.1.31) can also catalyze this conversion. 2-Enoate reductase enzymes are known to catalyze the NADH-dependent reduction of a wide variety of α, β-unsaturated carboxylic acids and aldehydes (Rohdich et al., *Biol. Chem.* 276:5779-5787 (2001)). 2-Enoate reductases is encoded by enr in several species of *Clostridia* including *C. tyrobutyricum*, and *C. thermoaceticum* (now called *Moorella thermoaceticum*) (Geisel et al., *Arch. Microbiol* 135:51-57 (1983); Rohdich et al., supra). In the recently published genome sequence of *C. kluyveri*, 9 coding sequences for enoate reductases were reported, out of which one has been characterized (Seedorf et al., *Proc. Natl. Acad Sci. U.S.A.* 105:2128-2133 (2008)). The enr genes from both *C. tyrobutyricum* and *M. thermoaceticum* have been cloned and sequenced and show 59% identity to each other. The former gene is also found to have approximately 75% similarity to the characterized gene in *C. kluyveri* (Geise) et al., supra). It has been reported based on these sequence results that enr is very similar to the dienoyl CoA reductase in *E. coli* (fadH) (Rohdich et al., supra). The *C. thermoaceticum* enr gene has also been expressed in a catalytically active form in *E. coli* (Rohdich et al., supra). The protein sequences for exemplary gene products can be found using the following GenBank accession numbers shown below in Table 29.

TABLE 29

| Protein | GenBank ID | GI Number | Organism |
|---|---|---|---|
| enr | ACA54153.1 | 169405742 | *Clostridium botulinum* A3 str |
| enr | CAA71086.1 | 2765041 | *Clostridium tyrobutyricum* |
| enr | CAA76083.1 | 3402834 | *Clostridium kluyveri* |
| enr | YP_430895.1 | 83590886 | *Moorella thermoacetica* |
| fadH | NP_417552.1 | 16130976 | *Escherichia coli* |

An alternate route for synthesizing cyclohexanone from 6-ketocyclohex-1-ene-1-carboxyl-CoA (6-KCH-CoA) employs similar enzymes applied in a different order. In this route, 6-KCH-CoA is first reduced to 2-ketocyclohexane-1-carboxyl-CoA (2-KCH-CoA) by an enoyl-CoA reductase (EC 1.3.1.-) (FIG. 3, step 5). Exemplary enoyl-CoA reductase enzymes are described above for the reduction of 6-carboxy-hex-2-enoyl-CoA to pimeloyl-CoA.

In step 8 of FIG. 3, 6-KCH is reduced to 2-KCH by an enoate reductase (EC 1.3.1.-). Enzymes for enoate reductases are described above for the reduction of 2-cyclohexene-1-one to cyclohexanone. 2-KCH is subsequently decarboxylated to cyclohexanone via 2-KCH decarboxylase using the decarboxylase enzymes described above.

In some embodiments cyclohexanone is produced via a pathway for converting adipate semialdehyde to cyclohexanone. Adipate semialdehyde is not a naturally occurring metabolite in commonly used production organisms such as *Escherichia coli* and *Saccharoinyces cerevisiae*. However, a number of biosynthetic routes for adipate biosynthesis have recently been disclosed [U.S. patent application Ser. No. 12/413,355]. In this report, we assume that adipate semialdehyde is produced from molar equivalents of acetyl-CoA and succinyl-CoA, joined by a beta-ketothiolase to form oxoadipyl-CoA. Oxoadipyl-CoA is then converted to adipyl-CoA in three enzymatic steps: reduction of the ketone, dehydration, and reduction of the enoyl-CoA. Once formed, adipyl-CoA is converted to adipate semialdehyde by a CoA-dependent aldehyde dehydrogenase.

The pathway to cyclohexanone from adipate semialdehyde entails four enzymatic steps as shown in FIG. 4. In the first step, adipate semialdehyde is dehydrated and cyclized, forming cyclohexane-1,2-dione (12-CHDO). 12-CHDO is then reduced to the diol by cyclohexane-1,2-diol dehydrogenase. Finally, a diol dehydratase converts cyclohexane-1,2-diol to cyclohexanone.

This pathway is capable of achieving high product and energetic yields. The maximum theoretical cyclohexanone yield is 0.75 mol/mol from glucose. With a wild-type PPCK activity, the pathway achieves an ATP yield of 1.362 mole ATP per mole glucose utilized at the maximum cyclohexanone yield. With PEP carboxykinase able to function in the ATP-generating direction, the ATP yield is further increased to 2.11 mol/mol.

In organisms that degrade caprolactam such as *Pseudomonas aeruginosa* (Kulkarni et al., *Curr. Microbiol.* 37:191-194 (1998); Steffensen et al., *Appl. Environ Microbiol* 61:2859-2862 (1995)), adipate is readily converted to cyclohexa-1,2-dione by a dehydratase in the EC 3.7.1 family. This transformation was also identified in cell extracts of *Azoarcus* species, as part of an anaerobic cyclohexan-1,2-diol degradation pathway (Harder, *J. Arch. Microbiol.* 168:199-203 (1997)). A similar transformation is catalyzed in the myo-inositol degradation pathway, in which the cyclic dione 2,3-diketo-4-deoxy-epi-inositol is hydrolyzed to a linear product, 5-dehydro-2-deoxy-D-gluconate, by a diketodeoxyinositol hydrolase (EC 3.7.1.-). A partially purified protein catalyzing this reaction has been studied in *Klebsiella aerogenes* (Berman et al., *J. Biol. Chem.* 241:800-806 (1966)).

The conversion of cyclohexane-1,2-dione to a diol can be accomplished by cyclohexane-1,2-diol dehydrogenase (EC 1.1.1.174). This enzymatic activity has been demonstrated in *Acinetobacter* TD63 (Davey et al., *Eur. J. Biochem.* 74:115-127 (1977)). It has been indicated that cyclohexanol dehydrogenase (EC 1.1.1.245), an enzyme with a broad substrate range, can catalyze these conversions. Cyclohexanol dehydrogenase enzymes from *Rhodococcus* sp TK6 (Tae-Kang et al., *J. Microbiol. Biotechnol.* 12:39-45 (2002)), a denitrifying *Pseudomonas* sp. (Dangel et al., supra), *Nocardia* sp (Stirling et al., *Curr. Micrbiol.* 4:37-40 (1980)) and *Xanthobacter* sp. (Trower et al., *App. Environ. Microbiol.* 49"1282-1289 (1985)) have all been shown to convert cyclohexan-1,2-diol to cyclohexan-1,2-dione. The gene associated with a cyclohexanol dehydrogenase in *Acinetobacter* sp NCIMB9871 was identified in 2000 (Cheng et al., *J. Bacteriol.* 182:4744-4751). This enzyme, encoded by chnA, has not been tested for activity on cyclohexan-1,2-dione or cyclohexan-1,2-diol. A BLAST comparison of the *Acinetobacter* ChnA protein sequence identifies genes from other organisms including *Ralstonia metallireducens* (57% identity), and *Pseudomonas putida* (47% identity). A cyclohexanol dehydrogenase gene from *Comamonas testosteroni* has also been expressed and characterized in *E. coli* (Van Beilen et al., *Environ. Micrbiol* 5:174-182 (2003)); a similar gene was also identified in *Xanthobacter flavus* (Van Beilen et al., supra). The protein sequences for exemplary gene products can be found using the following GenBank accession numbers shown below in Table 30.

TABLE 30

| Protein | GenBank ID | GI Number | Organism |
|---|---|---|---|
| chnA | BAC80215.1 | 33284995 | *Acinetobacter* sp NCIMB9871 |
| chnA | CAD10799.1 | 16943680 | *Comamonas testosteroni* |
| chnA | CAD10802.1 | 18495819 | *Xanthobacter flavus* |
| Rmet_1335 | YP_583487.1 | 94310277 | *Ralstonia metallireducens* |
| PP_1946 | NP_744098.1 | 26988673 | *Pseudomonas putida* |

Another enzyme which can accomplish this conversion is diacetyl reductase (EC 1.1.1.5). Naturally catalyzing the conversion of diacetyl (2,3-butanedione) to acetoin and subsequent reduction to 2,3-butanediol, two NADPH-dependent diacetyl reductase enzymes from *S. cerevisiae* have been shown to also accept cyclohexan-1,2-dione as a substrate (Heidlas et al., *Eur. Biochem.* 188:165-174 (1990)). The (S)-specific NADPH-dependent diacetyl reductase from this study was later identified as D-arabinose dehydrogenase, the gene product of ARA1 (Katz et al., *Enzyme Microb. Technol.* 33:163-172 (2003)). The NADH-dependent gene product of BDH1 of *S. cerevisiae* also has diacetyl reductase functionality (Gonzalez et al., *J. Biol. Chem.* 275:33876-35885 (2000)). Several other enzymes with diketone reductase functionality have been identified in yeast, encoded by genes GCY1, YPR1, GRE3, YIR036c (Johanson et al. *FEMS Yeast Res.* 5:513-525 (2005)). The protein sequences for exemplary gene products can be found using the following GenBank accession numbers shown below in Table 31.

TABLE 31

| Protein | GenBank ID | GI Number | Organism |
|---|---|---|---|
| ARA1 | NP_009707.1 | 6319625 | *Saccharomyces cerevisiae* |
| BDH1 | NP_009341.1 | 6319258 | *Saccharomyces cerevisiae* |

TABLE 31-continued

| Protein | GenBank ID | GI Number | Organism |
|---|---|---|---|
| GCY1 | NP_014763.1 | 6324694 | Saccharomyces cerevisiae |
| YPR1 | NP_010656.1 | 6320576 | Saccharomyces cerevisiae |
| GRE3 | NP_011972.1 | 6321896 | Saccharomyces cerevisiae |
| YIR036c | AAS56566.1 | 45270370 | Saccharomyces cerevisiae |

Conversion of the cyclohexan-1,2-diol to cyclohexanone has not been demonstrated enzymatically. A similar transformation is catalyzed by the diol dehydratase myo-inosose-2-dehydratase (EC 42.1.44). Myo-inosose is a six-membered ring containing adjacent alcohol groups, similar to cyclohexan-1,2-diol. A purified enzyme encoding myo-inosose-2-dehydratase functionality has been studied in *Klebsiella aerogenes* in the context of myo-inositol degradation (Berman et al., supra), but has not been associated with a gene to date.

Diol dehydratase or propanediol dehydratase enzymes (EC 4.2.1.28) capable of converting the secondary diol 2,3-butanediol to methyl ethyl ketone would be appropriate for this transformation. Adenosylcobalamin-dependent diol dehydratases contain alpha, beta and gamma subunits, which are all required for enzyme function. Exemplary genes are found in *Klebsiella pneumoniae* (Tobimatsu et al., *Biosci Biotechnol. Biochem.* 62:1774-1777 (1998); Toraya et al., *Biochem. Biophys. Res. Commun.* 69:475-480 (1976)), *Salmonella typhimurium* (Bobik et al., *Bacteriol.* 179:6633-6639 (1997)), *Klebsiella avytoca* (Tobimatsu et al., *J. Biol. Chem.* 270:7142-7148 (1995)) and *Lactobacillus collinoides* (Sauvageot et al., *FEMS Microbiol. Lett.* 209:69-74 (2002)). Methods for isolating diol dehydratase genes in other organisms are well known in the art (e.g. U.S. Pat. No. 5,686,276). The protein sequences for exemplary gene products can be found using the following GenBank accession numbers shown below in Table 32.

TABLE 32

| Protein | GenBank ID | GI Number | Organism |
|---|---|---|---|
| pddC | AAC98386.1 | 4063704 | Klebsiella pneumoniae |
| pddB | AAC98385.1 | 4063703 | Klebsiella pneumoniae |
| pddA | AAC98384.1 | 4063702 | Klebsiella pneumoniae |
| pduC | AAB84102.1 | 2587029 | Salmonella typhimurium |
| pduD | AAB84103.1 | 2587030 | Salmonella typhimurium |
| pduE | AAB84104.1 | 2587031 | Salmonella typhimurium |
| pddA | BAA08099.1 | 868006 | Klebsiella oxytoca |
| pddB | BAA08100.1 | 868007 | Klebsiella oxytoca |
| pddC | BAA08101.1 | 868008 | Klebsiella oxytoca |
| pduC | CAC82541.1 | 18857678 | Lactobacillus collinoides |
| pduD | CAC82542.1 | 18857679 | Lactobacillus collinoides |
| pduE | CAD01091.1 | 18857680 | Lactobacillus collinoides |

Enzymes in the glycerol dehydratase family (EC 4.2.1.30) can also be used to convert cyclohexan-1,2-diol to cyclohexanone. Exemplary genes can be found in *Klebsiella pneumoniae* (WO 2008/137403), *Clostridium pasteuranum* (Macis et al., *FEMS Microbiol. Lett.* 164:21-28 (1998)) and *Citrobacter freundii* (Seyfried et al., *J. Bacteriol* 178:5793-5796 (1996)). The protein sequences for exemplary gene products can be found using the following GenBank accession numbers shown below in Table 33.

TABLE 33

| Protein | GenBank ID | GI Number | Organism |
|---|---|---|---|
| dhaB | AAC27922.1 | 3360389 | Clostridium pasteuranum |
| dhaC | AAC27923.1 | 3360390 | Clostridium pasteuranum |

TABLE 33-continued

| Protein | GenBank ID | GI Number | Organism |
|---|---|---|---|
| dhaE | AAC27924.1 | 3360391 | Clostridium pasteuranum |
| dhaB | P45514.1 | 1169287 | Citrobacter freundii |
| dhaC | AAB48851.1 | 1229154 | Citrobacter freundii |
| dhaE | AAB48852.1 | 1229155 | Citrobacter freundii |

When a B12-dependent diol dehydratase is utilized, heterologous expression of the corresponding reactivating factor can be used. These factors are two-subunit proteins. Exemplary genes are found in *Klebsiella* oxytoca (Mori et al., *J. Biol. Chem.* 272:32034-32041 (1997)), *Salmonella typhimurium* (Bobik et al., supra; Chen et al., *J. Bacterial.* 176:5474-5482 (1994)). *Lactobacillus collinoides* (Sauvageot et al., supra), *Klebsiella pneumonia* (WO 2008/137403). The protein sequences for exemplary gene products can be found using the following GenBank accession numbers shown below in Table 34.

TABLE 34

| Protein | GenBank ID | GI Number | Organism |
|---|---|---|---|
| ddrA | AAC15871 | 3115376 | Klebsiella oxytoca |
| ddrB | AAC15872 | 3115377 | Klebsiella oxytoca |
| pduG | AAB84105 | 16420573 | Salmonella typhimurium |
| pduH | AAD39008 | 16420574 | Salmonella typhimurium |
| pduG | YP_002236779 | 206579698 | Klebsiella pneumonia |
| pduH | YP_002236778 | 206579863 | Klebsiella pneumonia |
| pduG | CAD01092 | 29335724 | Lactobacillus collinoides |
| pduH | AJ297723 | 29335725 | Lactobacillus collinoides |

Exemplary B12-independent diol dehyratase enzymes include glycerol dehydrogenase and dihydroxyacid dehydratase (EC 4.2.1.9). Cyclohexan-1,2-diol is not a known substrate of either enzyme. B12-independent diol dehydratase enzymes utilize S-adenosylmethionine (SAM) as a cofactor and function under strictly anaerobic conditions. The glycerol dehydrogenase and corresponding activating factor of *Clostridium butyricum*, encoded by dhaB1 and dhaB2, have been well-characterized (O'Brien et al., *Biochemistry* 43:4635-4645 (2004); Raynaud et al., *Proc. Natl. Acad Sci U.S.A* 100:5010-5015 (2003)). This enzyme was recently employed in a 1,3-propanediol overproducing strain of *E. coli* and was able to achieve very high titers of product (Tang et al., *Appl. Environ. Microbiol.* 75:1628-1634 (2009)). An additional B12-independent diol dehydratase enzyme and activating factor from *Roseburia inulinivorans* was shown to catalyze the conversion of 2,3-butanediol to 2-butanone (US 2009/09155870). Dihydroxy-acid dehydratase (DHAD, EC 4.2.1.9) is a B12-independent enzyme participating in branched-chain amino acid biosynthesis. In its native role, it converts 2,3-dihydroxy-3-methylvalerate to 2-keto-3-methyl-valerate, a precursor of isoleucine. In valine biosynthesis the enzyme catalyzes the dehydration of 2,3-dihydroxy-isovalerate to 2-oxoisovalerate. The DHAD from *Sulfolobus solfataricus* has a broad substrate range and activity of a recombinant enzyme expressed in *E. coli* was demonstrated on a variety of aldonic acids (KIM et al., *J. Biochem.* 139:591-596 (2006)). The *S. solfataricus* enzyme is tolerant of oxygen unlike many diol dehydratase enzymes. The *E. coli* enzyme, encoded by ilvD, is sensitive to oxygen, which inactivates its iron-sulfur cluster (Flint et al., *J. Biol. Chem.* 268:14732-14742 (1993)). Similar enzymes have been characterized in *Neurospora crassa* (Altmiller et al., *Arch. Biochem. Biophys.* 138:160-170 (1970)) and *Salmonella typhimurium* (Armstrong et al., *Biochim. Biophys. Acta* 498:282-293 (1977)).

The protein sequences for exemplary gene products can be found using the following GenBank accession numbers shown below in Table 35.

TABLE 35

| Protein | GenBank ID | GI Number | Organism |
| --- | --- | --- | --- |
| dhaB1 | AAM54728.1 | 27461255 | Clostridium butyricum |
| dhaB2 | AAM54729.1 | 27461256 | Clostridium butyricum |
| rdhtA | ABC25539.1 | 83596382 | Roseburia inulinivorans |
| rdhtB | ABC25540.1 | 83596383 | Roseburia inulinivorans |
| ilvD | NP_344419.1 | 15899814 | Sulfolobus solfataricus |
| ilvD | AAT48208.1 | 48994964 | Escherichia coli |
| ilvD | NP_462795.1 | 16767180 | Salmonella typhimurium |
| ilvD | XP_958280.1 | 85090149 | Neurospora crassa |

The diol dehydratase myo-inosose-2-dehydratase (EC 4.2.1.44) is another exemplary candidate. Myo-inosose is a six-membered ring containing adjacent alcohol groups. A purified enzyme encoding myo-inosose-2-dehydratase functionality has been studied in Klebsiella aerogenes in the context of myo-inositol degradation (Berman et al., J Biol. Chem. 241:800-806 (1966)), but has not been associated with a gene to date. The myo-inosose-2-dehydratase of Sinorhizobium fredii was cloned and functionally expressed in E. coli (Yoshida et al., Biosci. Biotechnol. Biochem. 70:2957-2964 (2006)). A similar enzyme from B. subtilis, encoded by iolE, has also been studied (Yoshida et al., Microbiology 150:571-580 (2004)). The protein sequences for exemplary gene products can be found using the following GenBank accession numbers shown below in Table 36.

TABLE 36

| Protein | GenBank ID | GI Number | Organism |
| --- | --- | --- | --- |
| iolE | P42416.1 | 1176989 | Bacillus subtilis |
| iolE | AAX24114.1 | 60549621 | Sinorhizobium fredii |

In some embodiments, the present invention provides a route for producing cyclohexanone from 4-acetylbutyrate (a so known as 5-oxohexanoate and 5-oxocaproic acid). In this pathway, 4-acetylbutyrate is cyclized to form 1,3-cyclohexanediol. Reduction of one of the keto groups and subsequent dehydration yields 2-cyclohexenone. 2-Cyclohexenone is then reduced to cyclohexanone. The enzyme activities of this pathway are naturally present in the denitrifying bacteria Alicycliphilus denitrificans sp. K601 (formerly known as Pseudomonas sp. K601) that metabolize cyclohexanol to support growth under anaerobic conditions (Dangel et al., (1989) supra; Dangel et al., (1988) supra; Mechichi et al., supra). Pathway intermediates 1,3-cyclohexanedione and 4-acetylbutyrate can also support growth of cells containing this pathway (Dangel et al., (1988) supra)).

Although 4-acetylbutyrate has been detected in cell extracts of Escherichia coli, the biosynthetic pathway to cyclohexanone includes two enzymatic steps for synthesizing 4-acetylbutyrate from 3-oxopimeloyl-CoA. 3-oxopimeloyl-CoA is an intermediate in the pathway for producing pimeloyl-CoA as described above. Enzymes for producing 3-oxopimeloyl-CoA from acetoacetyl-CoA are described in that section. Enzymes for transforming 3-oxopimeloyl-CoA to cyclohexanone (FIG. 5) are described herein.

The first step of this pathway entails removal of the CoA moiety of 3-oxopimeloyl-CoA, which can be accomplished by a CoA-transferase, synthetase or hydrolase. Several known enzymes that act on 3-oxoacids can likely act on 3-oxopimeloyl-CoA as an alternate substrate. The various CoA-synthetase, CoA-hydrolase (acting on thioester) and CoA-transferase enzymes are detailed above.

The second step of the pathway entails decarboxylation of 3-oxopimelate to 4-acetyl by a 3-oxoacid decarboxylase such as acetoacetate decarboxylase (EC 4.1.1.4). Exemplary genes for 3-oxoacid decarboxylases are enumerated above. This decarboxylation reaction can also occur spontaneously, rather than enzyme-catalyzed. In E. coli, several 3-oxoacids produced during amino acid biosynthesis have been shown to undergo spontaneous decarboxylation (Boylan et al., Biochem Biophysc. Res. Commun. 85:190-197 (1978)).

Activity of 1,3-cyclohexanedione hydrolase (4-acetylbutyrate dehydratase) has been demonstrated in the hydrolytic ring-cleavage direction in Alicycliphilus denitrificans (Dangel (1989) supra). The enzyme catalyzing this step has been characterized in cell extracts.

3-Hydroxycyclohexanone dehydrogenase (EC 1.1.99.26) reduces one of the ketones of cyclohexane-1,3-dione to 3-hydroxycyclohexanone. This enzyme has been characterized in cell extracts of Alicycliphilus denitrificans (Dangel et al., (1989) supra). Cyclohexanol dehydrogenase enzymes (EC 1.1.1.245) from Rhodococcus sp TK6 (Tae-Kang et al. supra), Nocardia sp (Stirling et al., supra), Xanthobacter sp. (Trower et al., supra) have been shown to oxidize cyclohexan-1,3-diol to cyclohexan-1,3-dione. Diacetyl reductase and additional cyclohexanol dehydrogenase genes discussed above are also applicable here.

Five recently identified beta-diketone reductases in Saccharomyces cerevisiae are able to reduce the bicyclic diketone bicyclo[2.2.2]octane-2,6-dione (BCO2,6D) to the corresponding ketoalcohol (Katz et al., Biotechnol. Bioeng. 84:573-582 (2003)). This transformation is similar to the reduction of cyclohexane-1,3-dione (step 4, FIG. 5). The enzymes are encoded by at the loci YMR226c, YDR368w, YOR120w, YGL157w and YGL039w. The protein sequences for exemplary gene products can be found using the following GenBank accession numbers shown below in Table 37.

TABLE 37

| Protein | GenBank ID | GI Number | Organism |
| --- | --- | --- | --- |
| YMR226c | NP_013953.1 | 6323882 | Saccharomyces cerevisiae |
| YDR368w | NP_010656.1 | 6320576 | Saccharomyces cerevisiae |
| YOR120w | NP_014763.1 | 6324694 | Saccharomyces cerevisiae |
| YGL157w | NP_011358.1 | 6321281 | Saccharomyces cerevisiae |
| YGL039w | NP_011476.1 | 6321399 | Saccharomyces cerevisiae |

In the fifth step of the pathway, 3-hydroxycyclohexanone is dehydrated to form 2-cyclohexenone. This transformation is catalyzed by 2-cyclohexenone hydratase, characterized in cell extracts of Alicycliphilus denitrificans K601 (Dangel et al., (1989) supra). Another enzyme capable of dehydrating a cyclic beta-hydroxy ketone is 3-dehydroquinate dehydratase (EC 4.2.1.10), also known as dehydroquinase. This enzyme reversibly dehydrates 3-dehydroquinate to form 3-dehydroshikimate (FIG. 6) and has been extensively studied as an antibiotic target. Activity on 3-hydroxycyclohexanone as a substrate has not been demonstrated. Two distinct types of dehydroquinase, type I and type II, catalyze identical reactions but differ in amino acid composition, structure and catalytic mechanism (Gourley et al., Nat. Struct. Biol. 6:521-525 (1999); Kleanthous et al., Biochem. J. 282 (Pt 3): 687-695 (1992)). High resolution structural data is available for the type I enzyme from Salmonella typhi (Gourley et al., supra) and for the type II enzymes from Mycobacterium tuberculosis (Gobel et al., J. Bacteriol. 184:216-223 (2002)) and Streptomyces coelicolor (Roszak et al., Structure 10:493-503

(2002)). Dehydroquinases have also been cloned, purified and characterized in *Heliobacter pylori* (Bottomley et al., *Biochem. J.* 319 (Pt 2):559-565 (1996)), *Salmonella typhi* and *Escherichia coli* (Chaudhuri et al., *Biochem. J.* 275 (pt 1):1-6 (1991)). The protein sequences for exemplary gene products can be found using the following GenBank accession numbers shown below in Table 38.

TABLE 38

| Protein | GenBank ID | GI Number | Organism |
|---|---|---|---|
| aroD | NP_416208.1 | 16129649 | *Escherichia coli* K12 sp. MG1655 |
| aroD | CAA38418.1 | 47642 | *Salmonella enterica* (*Salmonella typhi*) |
| aroQ | NP_626225.1 | 21220446 | *Streptomyces coelicolor* |
| aroD | NP_223105.1 | 15611454 | *Heliobacter pylori* |
| aroQ | P0A4Z6.2 | 61219243 | *Mycobacterium tuberculosis* |

The enzyme 2-hydroxyisoflavanone dehydrogenase dehydrates the cyclic beta-hydroxyl group of 2-hydroxyisoflavanone to form isoflavanone (FIG. 6B). Enzymes with this activity have been characterized in soybean (*Glycine max*) and *Glycyrrhiza echinata* (Akashi et al., *Plant Physiol.* 137: 882-891 (2005)). The soybean enzyme HIDH was found to accept alternate substrates, whereas the *G. echinata* enzyme, HIDM, exhibited strict substrate specificity (Akashi et al., supra). The protein sequences for exemplary gene products can be found using the following GenBank accession numbers shown below in Table 39.

TABLE 39

| Protein | GenBank ID | GI Number | Organism |
|---|---|---|---|
| HIDH | BAD80840.1 | 56692180 | *Glycine max* |
| HIDM | BAD80839.1 | 56692178 | *Glycyrrhiza echinata* |

The final pathway step, reduction of 2-cyclohexenone to cyclohexanone, is catalyzed by cyclohexanone dehydrogenase (EC 1.3.99.14). This reaction is identical to the final step of the pathway described above In some embodiments, the present invention provides an alternate pathway to pimeloyl-CoA starting from 2,6-diaminopentanoate. 2,6-diaminopimelate (26-DAP) is an intermediate in lysine biosynthesis and is also a constituent of bacterial cell wall peptidoglycan. Pathways I-IV of lysine biosynthesis generate 2,6-diaminopimelate from L-aspartate, wherein aspartate is converted to aspartate-semialdehyde, which is then hydrolyzed with pyruvate to form 2,3-dihydropicolinate. The conversion of 2,3-dihydropicolinate to 2,6-diaminopimelate can be accomplished by different enzymes, and involve different metabolic intermediates. In *E. coli*, the lysine biosynthesis pathway I accomplishes this conversion in four enzymatic steps.

Five enzymatic transformations convert 2,6-diaminopimelate pimeloyl-CoA: deamination of the secondary amines at the 2- and 6-positions, reduction of the resulting alkenes, and formation of a thioester bond with Coenzyme A (FIG. 7). Thioester bond formation can be performed by a CoA transferase or ligase. In conjunction with the pimeloyl-CoA to cyclohexanone pathway in Section 2, the pathway is able to achieve a maximum theoretical yield of 0.75 moles of cyclohexanone per mole of glucose utilized. Even with a reversible PEP carboxykinase, the pathway is energetically limited with an ATP yield of 0.125 mol/mol. Yields were calculated under the assumption that enzymes with CoA transferase functionality are utilized (FIG. 7, step 5, FIG. 1, step 2). Aeration is not predicted to improve energetic yield.

Enzymes encoding the deamination of 2,6-dimaniopimelate and 2-aminoheptanedioate (FIG. 7, steps 1 and 3) can be provide by an aspartase (EC 4.3.1.1) which catalyzes a similar transformation, deamination of aspartate to fumarate (Viola, R. E., *Adv. Enzymol. Relat. Areas. Mol. Biol.* 74:295-341 (2000)). The crystal structure of the *E. coli* aspartase, encoded by aspA, provides insights into the catalytic mechanism and substrate specificity (Shi et al., *Biochemistry* 36:9136-9144 (1997)). The *E. coli* enzyme has been shown to react with alternate substrates aspartatephenylmethylester, asparagine, benzyl-aspartate and malate (Ma et al., *Ann. N.Y. Acad. Sci.* 672:60-65 (1992)). In a separate study, directed evolution was been employed on this enzyme to alter substrate specificity (Asano et al., *Biomol. Eng.* 22:95-101 (2005)). Enzymes with aspartase functionality have also been characterized in *Haemophilus influenzae* (Sjostrom et al., *Biochim. Biophys. Acta* 1324:182-190 (1997)), *Pseudomonas fluorescens* (Takagi et al., *J. Biochem.* 96:545-552 (1984)), *Bacillus subtilis* (Sjostrom et al., supra) and *Serratia marcescens* (Takagi et al., *J. Bacteriol.* 161:1-6 (1985)). The protein sequences for exemplary gene products can be found using the following GenBank accession numbers shown below in Table 40.

TABLE 40

| Protein | GenBank ID | GI Number | Organism |
|---|---|---|---|
| aspA | NP_418562 | 90111690 | *Escherichia coli* K12 subsp. MG1655 |
| aspA | P44324.1 | 1168534 | *Haemophilus influenzae* |
| aspA | P07346.1 | 114273 | *Pseudomonas fluorescens* |
| ansB | P26899.1 | 251757243 | *Bacillus subtilis* |
| aspA | P33109.1 | 416661 | *Serratia marcescens* |

Reduction of the pathway intermediates, 6-aminohept-2-enedioate and 6-carboxyhex-2-enoate, can be performed by a 2-enoate reductase (EC 1.3.1.31) as described above.

The acylation of pimelate to pimeloyl-CoA is catalyzed by pimeloyl-CoA synthetase, also called 6-carboxyhexanoate-CoA ligase (EC 6.2.1.14). This enzyme concomitantly forms AMP and pyrophosphate and consumes 2 ATP equivalents if pyrophosphate is hydrolyzed. The enzymes from *Bacillus subtilis* (Bower et al., supra), *Bacillus sphaericus* (Ploux et al., *Biochem. J.* 287 (pt 3):685-690 (1992)) and *Pseudomonas mendocina* (Binieda et al., *Biochem. J.* 340 (pt 3):793-801 (1999)) have been cloned, sequenced and characterized. The protein sequences for exemplary gene products can be found using the following GenBank accession numbers shown below in Table 41.

TABLE 41

| Protein | GenBank ID | GI Number | Organism |
|---|---|---|---|
| bioW | NP_390902.2 | 50812281 | *Bacillus subtilis* |
| bioW | CAA10043.1 | 3850837 | *Pseudomonas mendocina* |
| bioW | P22822.1 | 115012 | *Bacillus sphaericus* |

An enzyme capable of transferring the CoA moiety from acetyl-CoA or succinyl-CoA to pimelate is the *E. coli* acyl-CoA:acetate-CoA transferase, also known as acetate-CoA transferase (EC 2.8.3.8). This enzyme has been shown to transfer the CoA moiety to acetate from a variety of branched and linear acyl-CoA substrates, including isobutyrate (Matthies et al. *Appl. Environ. Microbiol.* 58:1435-1439 (1992)), valerate (Vanderwinkel et al., *Biochem. Biophys. Res. Com-* mun. 33:902-908 (1968)) and butanoate (Vanderwinkel et al., supra). This enzyme is encoded by atoA (alpha subunit) and atoD (beta subunit) in *E. coli* sp. K12 (Korolev et al., *Acta Crystallogr. D Biol Crystallogr.* 58:2116-2121 (2002); Vanderwinkel et al., supra) and actA and cg0592 in *Corynebacterium glutamicum* ATCC 13032 (Duncan et al., *Appl. Environ. Microbiol.* 68:5186-5190 (2002)). Similar enzymes exist in *Clostridium acetobutylicum* (Cary et al., *Appl. Environ Microbiol* 56:1576-1583 (1990)) and *Clostridium saccharoperbutylacetonicum* (Kosaka et al., *Biosci. Biotechnol Biochem.* 71:58-68 (2007)). The protein sequences for exemplary gene products can be found using the following GenBank accession numbers shown below in Table 42.

TABLE 42

| Protein | GenBank ID | GI Number | Organism |
| --- | --- | --- | --- |
| atoA | P76459.1 | 2492994 | *Escherichia coli* K12 |
| atoD | P76458.1 | 2492990 | *Escherichia coli* K12 |
| actA | YP_226809.1 | 62391407 | *Corynebacterium glutamicum* ATCC 13032 |
| cg0592 | YP_224801.1 | 62389399 | *Corynebacterium glutamicum* ATCC 13032 |
| ctfA | NP_149326.1 | 15004866 | *Clostridium acetobutylicum* |
| ctfB | NP_149327.1 | 15004867 | *Clostridium acetobutylicum* |
| ctfA | AAP42564.1 | 31075384 | *Clostridium saccharoperbutylacetonicum* |
| ctfB | AAP42565.1 | 31075385 | *Clostridium saccharoperbutylacetonicum* |

The gene products of cat1, cat2, and cat3 of *Clostridium kluyveri* catalyze analogous transformations, forming succinyl-CoA, 4-hydroxybutyryl-CoA, and butyryl-CoA from their corresponding acids (Seedorf et al., supra; Gourley et al., supra). Succinyl-CoA transferase activity is also present in *Trichomonas vaginalis* (van Grinsven et al., *J. Biol. Chem.* 283:1311-1418 (2008)) and *Trypanosoma brucei* (Riviere et al., *J. Biol. Chem.* 279:45337-45346 (2004)). The protein sequences for exemplary gene products can be found using the following GenBank accession numbers shown below in Table 43.

TABLE 43

| Protein | GenBank ID | GI Number | Organism |
| --- | --- | --- | --- |
| cat1 | P38946.1 | 729048 | *Clostridium kluyveri* |
| cat2 | P38942.2 | 172046066 | *Clostridium kluyveri* |
| cat3 | EDK35586.1 | 146349050 | *Clostridium kluyveri* |
| TVAG_395550 | XP_001330176 | 123975034 | *Trichomonas vaginalis* G3 |
| Tb11.02.0290 | XP_828352 | 71754875 | *Trypanosoma brucei* |

An alternate route for producing pimeloyl-CoA from 2,6-diaminopentanoate involves forming a thioester bond from one of the enoic acid pathway intermediates, 6-aminohept-2-enedioic acid or 6-carboxyhex-2-enoate. An enoyl-CoA transferase such as glutaconate CoA-transferase (EC 2.8.3.12) would be a good enzyme for this transformation. This enzyme from *Acidaminococcus fermentans*, which has been cloned and functionally expressed in *E. coli* (Mack et al., *Eur. J. Biochem.* 226:41-51 (1994)), reacts with multiple enoyl-CoA substrates including 3-butenoyl-CoA, acrylyl-CoA, and 2-hydroxyglutaryl-CoA (Buckel et al., *Eur. J. Biochem.* 118:315-321 (1981)). Glutaconate CoA-transferase activity has also been detected in *Clostridium sporosphaeroides* and *Clostridium symbiosum*. Additional glutaconate CoA-transferase enzymes can be inferred by homology to the *Acidaminococcus fermentans* protein sequence. The protein sequences for exemplary gene products can be found using the following GenBank accession numbers shown below in Table 44.

TABLE 44

| Protein | GenBank ID | GI Number | Organism |
| --- | --- | --- | --- |
| gctA | CAA57199.1 | 559392 | *Acidaminococcus fermentans* |
| gctB | CAA57200.1 | 559393 | *Acidaminococcus fermentans* |
| gctA | ACJ24333.1 | 212292816 | *Clostridium symbiosum* |
| gctB | ACJ24326.1 | 212292808 | *Clostridium symbiosum* |
| gctA | NP_603109.1 | 19703547 | *Fusobacterium nucleatum* |
| gctB | NP_603110.1 | 19703548 | *Fusobacterium nucleatum* |

When an enoyl-CoA intermediate is formed from 6-aminohept-2-enedioate or 6-carboxyhex-2-enoate, reduction of the alkene can be performed by an enoyl-CoA reductase. Exemplary enoyl-CoA reductase genes are described above.

The non-naturally occurring microbial organisms of the invention can be produced by introducing expressible nucleic acids encoding one or more of the enzymes or proteins participating in one or more cyclohexanone biosynthetic pathways. Depending on the host microbial organism chosen for biosynthesis, nucleic acids for some or all of a particular cyclohexanone biosynthetic pathway can be expressed. For example, if a chosen host is deficient in one or more enzymes or proteins for a desired biosynthetic pathway, then expressible nucleic acids for the deficient enzyme(s) or protein(s) are introduced into the host for subsequent exogenous expression. Alternatively, if the chosen host exhibits endogenous expression of some pathway genes, but is deficient in others, then an encoding nucleic acid is needed for the deficient enzyme(s) or protein(s) to achieve cyclohexanone biosynthesis. Thus, anon-naturally occurring microbial organism of the invention can be produced by introducing exogenous enzyme or protein activities to obtain a desired biosynthetic pathway or a desired biosynthetic pathway can be obtained by introducing one or more exogenous enzyme or protein activities that, together with one or more endogenous enzymes or proteins, produces a desired product such as cyclohexanone.

Depending on the cyclohexanone biosynthetic pathway constituents of a selected host microbial organism, the non-naturally occurring microbial organisms of the invention will include at least one exogenously expressed cyclohexanone pathway-encoding nucleic acid and up to all encoding nucleic acids for one or more cyclohexanone biosynthetic pathways. For example, cyclohexanone biosynthesis can be established in a host deficient in a pathway enzyme or protein through exogenous expression of the corresponding encoding nucleic acid. In a host deficient in all enzymes or proteins of a cyclohexanone pathway, exogenous expression of all enzyme or proteins in the pathway can be included, although it is understood that all enzymes or proteins of a pathway can be expressed even if the host contains at least one of the pathway enzymes or proteins. For example, exogenous expression of all enzymes or proteins in a pathway for production of cyclohexanone can be included, such as a PEP carboxykinase, a 2-ketocyclohexane-1-carboxyl-CoA hydrolase (acting on C—C bond), a 2-ketocyclohexane-1-carboxylate decarboxylase and an enzyme selected from a 2-ketocyclohexane-1-carboxyl-CoA hydrolase (acting on thioester), a 2-ketocyclohexane-1-carboxyl-CoA transferase, and a 2-ketocyclohexane-1-carboxyl-CoA synthetase. Such a pathway can also include a complete set of exogenous enzymes for the production of pimeloyl-CoA, which includes a 3-hydroxybutyryl-CoA dehydratase, a glutaryl-CoA dehydrogenase, a oxopimeloyl-CoA:glutaryl-CoA acyltransferase, a 3-hydroxypimeloyl-CoA dehydrogenase, a 3-hydroxypimeloyl-CoA dehydratase, and a pimeloyl-CoA dehydrogenase.

Other examples of complete enzyme sets for the production of cyclohexanone include for example (a) PEP carboxykinase, 6-ketocyclohex-1-ene-1-carboxyl-CoA hydrolase (acting on C—C bond), 6-ketocyclohex-1-ene-1-carboxylate decarboxylase, cyclohexanone dehydrogenase, and an enzyme selected from 6-ketocyclohex-1-ene-1-carboxyl-CoA synthetase, 6-ketocyclohex-1-ene-1-carboxyl-CoA hydrolase (acting on thioester), and 6-ketocyclohex-1-ene-1-carboxyl-CoA transferase; (b) PEP carboxykinase, 6-ketocyclohex-1-ene-1-carboxyl-CoA hydrolase (acting on C—C bond), 6-ketocyclohex-1-ene-1-carboxylate reductase, 2-ketocyclohexane-1-carboxylate decarboxylase, and an enzyme selected from 6-ketocyclohex-1-ene-1-carboxyl-CoA synthetase, 6-ketocyclohex-1-ene-1-carboxyl-CoA hydrolase (acting on thioester), and 6-ketocyclohex-1-ene-1-carboxyl-CoA transferase; and (c) PEP carboxykinase, 6-ketocyclohex-1-ene-1-carboxyl-CoA hydrolase (acting on C—C bond), 6-ketocyclohex-1-ene-1-carboxyl-CoA reductase, 2-ketocyclohexane-1-carboxylate decarboxylase, and an enzyme selected from the group consisting of 2-ketocyclohexane-1-carboxyl-CoA synthetase, 2-ketocyclohexane-1-carboxyl-CoA transferase, and 2-ketocyclohexane-1-carboxyl-CoA hydrolase (acting on thioester). Any of pathways (a)-(c) can also have a complete set of nucleic acids encoding a 3-hydroxypimeloyl-CoA pathway which includes an acetoacetyl-CoA reductase, a 3-hydroxybutyryl-CoA dehydratase, a glutaryl-CoA dehydrogenase, a oxopimeloyl-CoA:glutaryl-CoA acyltransferase, and a 3-hydroxypimeloyl-CoA dehydrogenase.

In still further exemplary embodiments a set of nucleic acids encoding a complete cyclohexanone pathway can include a PEP carboxykinase, an adipate semialdehyde dehydratase, a cyclohexane-1,2-diol dehydrogenase, and a cyclohexane-1,2-diol dehydratase. In yet still further embodiments a complete cyclohexanone pathway can include nucleic acids encoding a PEP carboxykinase, a 3-oxopimelate decarboxylase, a 4-acetylbutyrate dehydratase, a 3-hydroxycyclohexanone dehydrogenase, a 2-cyclohexenone hydratase, a cyclohexanone dehydrogenase and an enzyme selected from a 3-oxopimeloyl-CoA synthetase, a 3-oxopimeloyl-CoA hydrolase (acting on thioester), and a 3-oxopimeloyl-coA transferase. In some embodiments, this latter pathway can also include a 3-oxopimeloyl-CoA pathway which includes a 3-hydroxyacyl-CoA dehydrogenase, a 3-hydroxybutyryl-CoA dehydratase, a glutaryl-CoA dehydrogenase, and a oxopimeloyl-CoA:glutaryl-CoA acyltransferase.

Given the teachings and guidance provided herein, those skilled in the art will understand that the number of encoding nucleic acids to introduce in an expressible form will, at least, parallel the cyclohexanone pathway deficiencies of the selected host microbial organism. Therefore, a non-naturally occurring microbial organism of the invention can have one, two, three, four, five, six, seven, eight, nine, ten, eleven, twelve, thirteen, fourteen, fifteen or up to all nucleic acids encoding the enzymes or proteins constituting a cyclohexanone biosynthetic pathway disclosed herein. In some embodiments, the non-naturally occurring microbial organisms also can include other genetic modifications that facilitate or optimize cyclohexanone biosynthesis or that confer other useful functions onto the host microbial organism. One such other functionality can include, for example, augmentation of the synthesis of one or more of the cyclohexanone pathway precursors such as 2-ketocyclohexane-1-carboxylate, 2-ketocyclohexane-1-carboxyl-CoA, pimeloyl-CoA, 6-carboxyhex-2-enoyl-CoA, 3-hydroxypimeloyl-CoA, glutaryl-CoA, crotonyl-CoA, 3-hydroxybutyryl-CoA, acetoacetyl-CoA, 6-ketocyclohex-1-ene-1-carboxyl-CoA, 6-ketocyclohex-1-ene-1-carboxylate, 2-cyclohexenone, cyclohexane-1,2-diol, 2-hydroxycyclohexanone, cyclohexane-1,2-dione, adipate semialdehyde, 3-hydroxycyclohexanone, 1,3-cyclohexanedione, 4-acetylbutyrate, or 3-oxopimelate.

Generally, a host microbial organism is selected such that it produces the precursor of a cyclohexanone pathway, either as a naturally produced molecule or as an engineered product that either provides de novo production of a desired precursor or increased production of a precursor naturally produced by the host microbial organism. For example, acetoacetyl-CoA is produced naturally in a host organism such as E. coli. A host organism can be engineered to increase production of a precursor, as disclosed herein. In addition, a microbial organism that has been engineered to produce a desired precursor can be used as a host organism and further engineered to express enzymes or proteins of a cyclohexanone pathway.

In some embodiments, a non-naturally occurring microbial organism of the invention is generated from a host that contains the enzymatic capability to synthesize cyclohexanone. In this specific embodiment it can be useful to increase the synthesis or accumulation of a cyclohexanone pathway product to, for example, drive cyclohexanone pathway reactions toward cyclohexanone production. Increased synthesis or accumulation can be accomplished by, for example, overexpression of nucleic acids encoding one or more of the above-described cyclohexanone pathway enzymes or proteins. Over expression the enzyme or enzymes and/or protein or proteins of the cyclohexanone pathway can occur, for example, through exogenous expression of the endogenous gene or genes, or through exogenous expression of the heterologous gene or genes. Therefore, naturally occurring organisms can be readily generated to be non-naturally occurring microbial organisms of the invention, for example, producing cyclohexanone, through overexpression of one, two, three, four, five, six, seven, eight, nine, ten, eleven, twelve, thirteen, fourteen, fifteen, that is, up to all nucleic acids encoding cyclohexanone biosynthetic pathway enzymes or proteins. In addition, a non-naturally occurring organism can be generated by mutagenesis of an endogenous gene that results in an increase in activity of an enzyme in the cyclohexanone biosynthetic pathway.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring microbial organism.

It is understood that, in methods of the invention, any of the one or more exogenous nucleic acids can be introduced into a microbial organism to produce a non-naturally occurring microbial organism of the invention. The nucleic acids can be introduced so as to confer, for example, a cyclohexanone biosynthetic pathway onto the microbial organism. Alternatively, encoding nucleic acids can be introduced to produce an intermediate microbial organism having the biosynthetic capability to catalyze some of the required reactions to confer cyclohexanone biosynthetic capability. For example, a non-naturally occurring microbial organism having a cyclohexanone biosynthetic pathway can comprise at least two exogenous nucleic acids encoding desired enzymes or proteins, such as the combination of a 2-ketocyclohexane-1-carboxylate decarboxylase and a 2-ketocyclohexanecarboxyl-CoA hydrolase (acting on C—C bond; reaction run in reverse), or a 2-ketocyclohexane-1-carboxylate decarboxylase and a CoA synthetase, hydrolase or transferase, or a 2-ketocyclohexanecarboxyl-CoA hydrolase (acting on C—C bond; reaction run in reverse) and a CoA synthetase, hydrolase, or transferase, and the like. These are merely exemplary, and one skilled in the art will appreciate that any combination of two enzymes from any of the disclosed pathways can be provided by introduction of exogenous nucleic acids. Thus, it is understood that any combination of two or more enzymes or proteins of a biosynthetic pathway can be included in a non-naturally occurring microbial organism of the invention. Similarly, it is understood that any combination of three or more enzymes or proteins of a biosynthetic pathway can be included in a non-naturally occurring microbial organism of the invention, for example, a 2-ketocyclohexane-1-carboxylate decarboxylase, a 2-ketocyclohexanecarboxyl-CoA hydrolase (acting on C—C bond; reaction run in reverse), and a CoA synthetase, or a 2-ketocyclohexane-1-carboxylate decarboxylase, a 2-ketocyclohexanecarboxyl-CoA hydrolase (acting on C—C bond; reaction run in reverse), and a CoA hydrolase or a 2-ketocyclohexane-1-carboxylate decarboxylase, a 2-ketocyclohexanecarboxyl-CoA hydrolase (acting on C—C bond; reaction run in reverse), and a CoA transferase, and so forth, as desired, so long as the combination of enzymes and/or proteins of the desired biosynthetic pathway results in production of the corresponding desired product. Similarly, any combination of four, five, six, seven, eight, nine, ten, eleven, twelve, thirteen, fourteen, fifteen or more enzymes or proteins of a biosynthetic pathway as disclosed herein can be included in a non-naturally occurring microbial organism of the invention, as desired, so long as the combination of enzymes and/or proteins of the desired biosynthetic pathway results in production of the corresponding desired product.

In addition to the biosynthesis of cyclohexanone as described herein, the non-naturally occurring microbial organisms and methods of the invention also can be utilized in various combinations with each other and with other microbial organisms and methods well known in the art to achieve product biosynthesis by other routes. For example, one alternative to produce cyclohexanone other than use of the cyclohexanone producers is through addition of another microbial organism capable of converting a cyclohexanone pathway intermediate to cyclohexanone. One such procedure includes, for example, the fermentation of a microbial organism that produces a cyclohexanone pathway intermediate. The cyclohexanone pathway intermediate can then be used as a substrate for a second microbial organism that converts the cyclohexanone pathway intermediate to cyclohexanone. The cyclohexanone pathway intermediate can be added directly to another culture of the second organism or the original culture of the cyclohexanone pathway intermediate producers can be depleted of these microbial organisms by, for example, cell separation, and then subsequent addition of the second organism to the fermentation broth can be utilized to produce the final product without intermediate purification steps.

In other embodiments, the non-naturally occurring microbial organisms and methods of the invention can be assembled in a wide variety of subpathways to achieve biosynthesis of, for example, cyclohexanone. In these embodiments, biosynthetic pathways for a desired product of the invention can be segregated into different microbial organisms, and the different microbial organisms can be co-cultured to produce the final product. In such a biosynthetic scheme, the product of one microbial organism is the substrate for a second microbial organism until the final product is synthesized. For example, the biosynthesis of cyclohexanone can be accomplished by constructing a microbial organism that contains biosynthetic pathways for conversion of one pathway intermediate to another pathway intermediate or the product. Alternatively, cyclohexanone also can be biosynthetically produced from microbial organisms through co-culture or co-fermentation using two organisms in the same vessel, where the first microbial organism produces a cyclohexanone intermediate, such as pimeloyl-CoA, and the second microbial organism converts the intermediate to cyclohexanone.

Given the teachings and guidance provided herein, those skilled in the art will understand that a wide variety of combinations and permutations exist for the non-naturally occurring microbial organisms and methods of the invention together with other microbial organisms, with the co-culture of other non-naturally occurring microbial organisms having subpathways and with combinations of other chemical and/or biochemical procedures well known in the art to produce cyclohexanone.

Sources of encoding nucleic acids for a cyclohexanone pathway enzyme or protein can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli, Saccharomyces cerevisae, Clostridium acetobutylicum, Zoogloea ramigera, Pseudomonas putida, Syntrophus aciditrophicus, Haemophilus influenza, Azoarcus* sp. CIB, *Thauera aromatica, Glycine max,* and *Ascarius suum,* as well as other exemplary species disclosed herein or available as source organisms for corresponding genes. However, with the complete genome sequence available for now more than 550 species (with more than half of these available on public databases such as the NCBI), including 395 microorganism genomes and a variety of yeast, fungi, plant, and mammalian genomes, the identification of genes encoding the requisite cyclohexanone biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations enabling biosynthesis of cyclohexanone described herein with reference to a particular organism such as *E. coli* can be readily applied to other microorganisms, including prokaryotic and eukaryotic organisms alike. Given the teachings and guidance provided herein, those skilled in the art will know that a metabolic alteration exemplified in one organism can be applied equally to other organisms.

In some instances, such as when an alternative cyclohexanone biosynthetic pathway exists in an unrelated species, cyclohexanone biosynthesis can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art will understand that the actual gene usage between different organisms can differ. However, given the teachings and guidance provided herein, those skilled in the art also will understand that the teachings and methods of the invention can be applied to all microbial organisms using the cognate metabolic alterations to those exemplified herein to construct a microbial organism in a species of interest that will synthesize cyclohexanone.

Host microbial organisms can be selected from, and the non-naturally occurring microbial organisms generated in, for example, bacteria, yeast, fungus or any of a variety of other microorganisms applicable to fermentation processes. Exemplary bacteria include species selected from *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens*, and *Pseudomonas putida*. Exemplary yeasts or fungi include species selected from *Saccharomyces cerevisiae, Schizosaccharomyces pombe, Kluyveromyces laths, Kluyveromyces marxianus, Aspergillus terreus, Aspergillus niger* and *Pichia pastoris, E. coli* is a particularly useful host organism since it is a well characterized microbial organism suitable for genetic engineering. Other particularly useful host organisms include yeast such as *Saccharomyces cerevisiae*.

Methods for constructing and testing the expression levels of a non-naturally occurring cyclohexanone-producing host can be performed, for example, by recombinant and detection methods well known in the art. Such methods can be found described in, for example, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999).

Exogenous nucleic acid sequences involved in a pathway for production of cyclohexanone can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., *J. Biol. Chem.* 280: 4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

An expression vector or vectors can be constructed to include one or more cyclohexanone biosynthetic pathway encoding nucleic acids as exemplified herein operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

In some embodiments, the present invention provides a method for producing cyclohexanone, that includes culturing a non-naturally occurring microbial organism having a cyclohexanone pathway. The pathway includes at least one exogenous nucleic acid encoding a cyclohexanone pathway enzyme expressed in a sufficient amount to produce cyclohexanone, under conditions and for a sufficient period of time to produce cyclohexanone. The cyclohexanone pathway comprising a PEP carboxykinase, a 2-ketocyclohexane-1-carboxyl-CoA hydrolase (acting on C—C bond), a 2-ketocyclohexane-1-carboxylate decarboxylase and an enzyme selected from the group consisting of a 2-ketocyclohexane-1-carboxyl-CoA hydrolase (acting on thioester), a 2-ketocyclohexane-1-carboxyl-CoA transferase, and a 2-ketocyclohexane-1-carboxyl-CoA synthetase.

The present invention also provides a method for producing cyclohexanone that includes culturing a non-naturally occurring microbial organism having a cyclohexanone pathway that includes at least one exogenous nucleic acid encoding a cyclohexanone pathway enzyme expressed in a sufficient amount to produce cyclohexanone, under conditions and for a sufficient period of time to produce cyclohexanone, wherein the cyclohexanone pathway includes a set of cyclohexanone pathway enzymes. The set of cyclohexanone pathway enzymes selected from (a) PEP carboxykinase, 6-ketocyclohex-1-ene-1-carboxyl-CoA hydrolase (acting on (C—C bond), 6-ketocyclohex-1-ene-1-carboxylate decarboxylase, cyclohexanone dehydrogenase, and an enzyme selected from the group consisting of 6-ketocyclohex-1-ene-1-carboxyl-CoA synthetase, 6-ketocyclohex-1-ene-1-carboxyl-CoA hydrolase (acting on thioester), and 6-ketocyclohex-1-ene-1-carboxyl-CoA transferase; (b) PEP carboxykinase, 6-ketocyclohex-1-ene-1-carboxyl-CoA hydrolase (acting on C—C bond), 6-ketocyclohex-1-ene-1-carboxylate reductase, 2-ketocyclohexane-1-carboxylate decarboxylase, and an enzyme selected from the group consisting of 6-ketocyclohex-1-ene-1-carboxyl-CoA synthetase, 6-ketocyclohex-1-ene-1-carboxyl-CoA hydrolase (acting on thioester), and 6-ketocyclohex-1-ene-1-carboxyl-CoA transferase; and (c) PEP carboxykinase, 6-ketocyclohex-1-ene-1-carboxyl-CoA hydrolase (acting on C—C), 6-ketocyclohex-1-ene-1-carboxyl-CoA reductase, 2-ketocyclohexane-1-carboxylate decarboxylase, and an enzyme selected from the group consisting of 2-ketocyclohexane-1-carboxyl-CoA synthetase, 2-ketocyclohexane-1-carboxyl-CoA transferase, 2-ketocyclohexane-1-carboxyl-CoA hydrolase (acting on thioester).

The present invention also provides a method for producing cyclohexanone that includes culturing a non-naturally occurring microbial organism having a cyclohexanone pathway which includes at least one exogenous nucleic acid encoding a cyclohexanone pathway enzyme expressed in a sufficient amount to produce cyclohexanone, under conditions and for a sufficient period of time to produce cyclohexanone. Such a cyclohexanone pathway includes a PEP carboxykinase, an adipate semialdehyde dehydratase, a cyclohexane-1,2-diol dehydrogenase, and a cyclohexane-1,2-diol dehydratase.

In yet a further embodiment, the present invention provides a method for producing cyclohexanone that includes culturing a non-naturally occurring microbial organism having a cyclohexanone pathway having at least one exogenous nucleic acid encoding a cyclohexanone pathway enzyme expressed in a sufficient amount to produce cyclohexanone, under conditions and for a sufficient period of time to produce cyclohexanone. In such embodiments, the cyclohexanone pathway includes a PEP carboxykinase, a 3-oxopimelate decarboxylase, a 4-acetylbutyrate dehydratase, a 3-hydroxycyclohexanone dehydrogenase, a 2-cyclohexenone hydratase, a cyclohexanone dehydrogenase and an enzyme selected from the group consisting of a 3-oxopimeloyl-CoA synthetase, a 3-oxopimeloyl-CoA hydrolase (acting on thioester), and a 3-oxopimeloyl-coA transferase.

Suitable purification and/or assays to test for the production of cyclohexanone can be performed using well known methods. Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., *Biotechnol. Bioeng.* 90:775-779 (2005)), or other suitable assay and detection methods well known in the art. The individual enzyme or protein activities from the exogenous DNA sequences can also be assayed using methods well known in the art. For example, the specific activity of cyclohexanone dehydrogenase can be assayed in the reductive direction using a colorimetric assay adapted from the literature (Dune et al., *FEMS Microbiol. Rev.* 17:251-262 (1995); Palosaari et al., *Bacteriol.* 170:2971-2976 (1988); Welch et al., *Arch. Biochem. Biophys.* 273:309-318 (1989)). In this assay, the substrates 2-cyclohexenone and NADH are added to cell extracts in a buffered solution, and the oxidation of NADH is followed by reading absorbance at 340 nM at regular intervals. The resulting slope of the reduction in absorbance at 340 nM per minute, along with the molar extinction coefficient of NADH at 340 nM (6000) and the protein concentration of the extract, can be used to determine the specific activity of cyclohexanone dehydrogenase.

The cyclohexanone can be separated from other components in the culture using a variety of methods well known in the art. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

Any of the non-naturally occurring microbial organisms described herein can be cultured to produce and/or secrete the biosynthetic products of the invention. For example, the cyclohexanone producers can be cultured for the biosynthetic production of cyclohexanone.

For the production of cyclohexanone, the recombinant strains are cultured in a medium with carbon source and other essential nutrients. It is highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic conditions can be applied by perforating the septum with a small hole for limited aeration. Exemplary anaerobic conditions have been described previously and are well-known in the art. Exemplary aerobic and anaerobic conditions are described, for example, in United State patent application Ser. No. 11/891,602, filed Aug. 10, 2007. Fermentations can be performed in a batch, fed-batch or continuous manner, as disclosed herein.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

The growth medium can include, for example, any carbohydrate source which can supply a source of carbon to the non-naturally occurring microorganism. Such sources include, for example, sugars such as glucose, xylose, arabinose, galactose, mannose, fructose and starch. Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms of the invention for the production of cyclohexanone.

In addition to renewable feedstocks such as those exemplified above, the cyclohexanone microbial organisms of the invention also can be modified for growth on syngas as its source of carbon. In this specific embodiment, one or more proteins or enzymes are expressed in the cyclohexanone producing organisms to provide a metabolic pathway for utilization of syngas or other gaseous carbon source.

Synthesis gas, also known as syngas or producer gas, is the major product of gasification of coal and of carbonaceous materials such as biomass materials, including agricultural crops and residues. Syngas is a mixture primarily of $H_2$ and CO and can be obtained from the gasification of any organic feedstock, including but not limited to coal, coal oil, natural gas, biomass, and waste organic matter. Gasification is generally carried out under a high fuel to oxygen ratio. Although largely $H_2$ and CO, syngas can also include $CO_2$ and other gases in smaller quantities. Thus, synthesis gas provides a cost effective source of gaseous carbon such as CO and, additionally, $CO_2$.

The Wood-Ljungdahl pathway catalyzes the conversion of CO and $H_2$ to acetyl-CoA and other products such as acetate. Organisms capable of utilizing CO and syngas also generally have the capability of utilizing $CO_2$ and $CO_2/H_2$ mixtures through the same basic set of enzymes and transformations encompassed by the Wood-Ljungdahl pathway. $H_2$-dependent conversion of $CO_2$ to acetate by microorganisms was recognized long before it was revealed that CO also could be used by the same organisms and that the same pathways were involved. Many acetogens have been shown to grow in the presence of $CO_2$ and produce compounds such as acetate as long as hydrogen is present to supply the necessary reducing equivalents (see for example, Drake, *Acetogenesis*, pp. 3-60 Chapman and Hall, New York, (1994)). This can be summarized by the following equation:

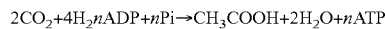

$$2CO_2 + 4H_2 nADP + nPi \rightarrow CH_3COOH + 2H_2O + nATP$$

Hence, non-naturally occurring microorganisms possessing the Wood-Ljungdahl pathway can utilize $CO_2$ and $H_2$ mixtures as well for the production of acetyl-CoA and other desired products.

The Wood-Ljungdahl pathway is well known in the art and consists of 12 reactions which can be separated into two branches: (1) methyl branch and (2) carbonyl branch. The methyl branch converts syngas to methyl-tetrahydrofolate (methyl-THF) whereas the carbonyl branch converts methyl-THF to acetyl-CoA. The reactions in the methyl branch are catalyzed in order by the following enzymes or proteins: ferredoxin oxidoreductase, formate dehydrogenase, formyltetrahydrofolate synthetase, methenyltetrahydrofolate cyclodehydratase, methylenetetrahydrofolate dehydrogenase and methylenetetrahydrofolate reductase. The reactions in the carbonyl branch are catalyzed in order by the following enzymes or proteins: methyltetrahydrofolate:corrinoid protein methyltransferase (for example, AcsE), corrinoid iron-sulfur protein, nickel-protein assembly protein (for example, AcsF), ferredoxin, acetyl-CoA synthase, carbon monoxide dehydrogenase and nickel-protein assembly protein (for example, CooC). Following the teachings and guidance provided herein for introducing a sufficient number of encoding nucleic acids to generate a cyclohexanone pathway, those skilled in the art will understand that the same engineering design also can be performed with respect to introducing at least the nucleic acids encoding the Wood-Ljungdahl enzymes or proteins absent in the host organism. Therefore, introduction of one or more encoding nucleic acids into the microbial organisms of the invention such that the modified organism contains the complete Wood-Ljungdahl pathway will confer syngas utilization ability.

Additionally, the reductive (reverse) tricarboxylic acid cycle coupled with carbon monoxide dehydrogenase and/or hydrogenase activities can also be used for the conversion of CO, $CO_2$ and/or $H_2$ to acetyl-CoA and other products such as acetate. Organisms capable of fixing carbon via the reductive TCA pathway can utilize one or more of the following enzymes: ATP citrate-lyase, citrate lyase, aconitase, isocitrate dehydrogenase, alpha-ketoglutarate:ferredoxin oxidoreductase, succinyl-CoA synthetase, succinyl-CoA transferase, fumarate reductase, fumarase, malate dehydrogenase, NAD(P)H:ferredoxin oxidoreductase, carbon monoxide dehydrogenase, and hydrogenase. Specifically, the reducing equivalents extracted from CO and/or $H_2$ by carbon monoxide dehydrogenase and hydrogenase are utilized to fix $CO_2$ via the reductive TCA cycle into acetyl-CoA or acetate. Acetate can be converted to acetyl-CoA by enzymes such as acetyl-CoA transferase, acetate kinase/phosphotransacetylase, and acetyl-CoA synthetase. Acetyl-CoA can be converted to cyclohexanone precursors, glyceraldehyde-3-phosphate, phosphoenolpyruvate, and pyruvate, by pyruvate:ferredoxin oxidoreductase and the enzymes of gluconeogenesis. Following the teachings and guidance provided herein for introducing a sufficient number of encoding nucleic acids to generate a cyclohexanone pathway, those skilled in the art will understand that the same engineering design also can be performed with respect to introducing at least the nucleic acids encoding the reductive TCA pathway enzymes or proteins absent in the host organism. Therefore, introduction of one or more encoding nucleic acids into the microbial organisms of the invention such that the modified organism contains the complete reductive TCA pathway will confer syngas utilization ability.

Accordingly, given the teachings and guidance provided herein, those skilled in the art will understand that a non-naturally occurring microbial organism can be produced that secretes the biosynthesized compounds of the invention when grown on a carbon source such as a carbohydrate. Such compounds include, for example, cyclohexanone and any of the intermediate metabolites in the cyclohexanone pathway. All that is required is to engineer in one or more of the required enzyme or protein activities to achieve biosynthesis of the desired compound or intermediate including, for example, inclusion of some or all of the cyclohexanone biosynthetic pathways. Accordingly, the invention provides a non-naturally occurring microbial organism that produces and/or secretes cyclohexanone when grown on a carbohydrate or other carbon source and produces and/or secretes any of the intermediate metabolites shown in the cyclohexanone pathway when grown on a carbohydrate or other carbon source. The cyclohexanone producing microbial organisms of the invention can initiate synthesis from any of the aforementioned intermediates.

The non-naturally occurring microbial organisms of the invention are constructed using methods well known in the art as exemplified herein to exogenously express at least one nucleic acid encoding a cyclohexanone pathway enzyme or protein in sufficient amounts to produce cyclohexanone. It is understood that the microbial organisms of the invention are cultured under conditions sufficient to produce cyclohexanone. Following the teachings and guidance provided herein, the non-naturally occurring microbial organisms of the invention can achieve biosynthesis of cyclohexanone resulting in intracellular concentrations between about 0.1-200 mM or more. Generally, the intracellular concentration of cyclohexanone is between about 3-200 mM, particularly between about 10-175 mM and more particularly between about 50-150 mM, including about 50 mM, 75 mM, 100 mM, 125 mM, or more. Intracellular concentrations between and above each of these exemplary ranges also can be achieved from the non-naturally occurring microbial organisms of the invention.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. patent application Ser. No. 11/891,602, filed Aug. 10, 2007. Any of these conditions can be employed with the non-naturally occurring microbial organisms as well as other anaerobic conditions well known in the art. Under such anaerobic conditions, the cyclohexanone producers can synthesize cyclohexanone at intracellular concentrations of 5-10 mM or more as well as all other concentrations exemplified herein. It is understood that, even though the above description refers to intracellular concentrations, cyclohexanone producing microbial organisms can produce cyclohexanone intracellularly and/or secrete the product into the culture medium.

The culture conditions can include, for example, liquid culture procedures as well as fermentation and other large scale culture procedures. As described herein, particularly useful yields of the biosynthetic products of the invention can be obtained under anaerobic or substantially anaerobic culture conditions.

As described herein, one exemplary growth condition for achieving biosynthesis of cyclohexanone includes anaerobic culture or fermentation conditions. In certain embodiments, the non-naturally occurring microbial organisms of the invention can be sustained, cultured or fermented under anaerobic or substantially anaerobic conditions. Briefly, anaerobic conditions refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The culture conditions described herein can be scaled up and grown continuously for manufacturing of cyclohexanone. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of cyclohexanone. Generally, and as with non-continuous culture procedures, the continuous and/or near-continuous production of cyclohexanone can include culturing a non-naturally occurring cyclohexanone producing organism of the invention in sufficient nutrients and medium to sustain and/or nearly sustain growth in an exponential phase. Continuous culture under such conditions can include, for example, 1 day, 2, 3, 4, 5, 6 or 7 days or more. Additionally, continuous culture can include 1 week, 2, 3, 4 or 5 or more weeks and up to several months. Alternatively, organisms of the invention can be cultured for hours, if suitable for a particular application. It is to be understood that the continuous and/or near-continuous culture conditions also can include all time intervals in between these exemplary periods. It is further understood that the time of culturing the microbial organism of the invention is for a sufficient period of time to produce a sufficient amount of product for a desired purpose.

Fermentation procedures are well known in the art. Briefly, fermentation for the biosynthetic production of cyclohexanone can be utilized in, for example, fed-batch fermentation and batch separation; fed-batch fermentation and continuous separation, or continuous fermentation and continuous separation. Examples of batch and continuous fermentation procedures are well known in the art.

In addition to the culturing and fermentation conditions disclosed herein, growth condition for achieving biosynthesis of cyclohexanone can include the addition of an osmoprotectant to the culturing conditions. In certain embodiments, the non-naturally occurring microbial organisms of the invention can be sustained, cultured or fermented as described herein in the presence of an osmoprotectant. Briefly, an osmoprotectant refers to a compound that acts as an osmolyte and helps a microbial organism as described herein survive osmotic stress. Osmoprotectants include, but are not limited to, betaines, amino acids, and the sugar trehalose. Non-limiting examples of such are glycine betaine, praline betaine, dimethylthetin, dimethylslfonioproprionate, 3-dimethylsulfonio-2-methylproprionate, pipecolic acid, dimethylsulfonioacetate, choline, L-carnitine and ectoine. In one aspect, the osmoprotectant is glycine betaine. It is understood to one of ordinary skill in the art that the amount and type of osmoprotectant suitable for protecting a microbial organism described herein from osmotic stress will depend on the microbial organism used. The amount of osmoprotectant in the culturing conditions can be, for example, no more than about 0.1 mM, no more than about 0.5 mM, no more than about 1.0 mM, no more than about 1.5 mM, no more than about 2.0 mM, no more than about 2.5 mM, no more than about 3.0 mM, no more than about 5.0 mM, no more than about 7.0 mM, no more than about 10 mM, no more than about 50 mM, no more than about 100 mM or no more than about 500 mM.

In addition to the above fermentation procedures using the cyclohexanone producers of the invention for continuous production of substantial quantities of cyclohexanone, the cyclohexanone producers also can be, for example, simultaneously subjected to chemical synthesis procedures to convert the product to other compounds or the product can be separated from the fermentation culture and sequentially subjected to chemical conversion to convert the product to other compounds, if desired.

Directed evolution is a powerful approach that involves the introduction of mutations targeted to a specific gene in order to improve and/or alter the properties of an enzyme. Improved and/or altered enzymes can be identified through the development and implementation of sensitive high-throughput screening assays that allow the automated screening of many enzyme variants (e.g., $>10^4$). Iterative rounds of mutagenesis and screening typically are performed to afford an enzyme with optimized properties. Computational algorithms that can help to identify areas of the gene for mutagenesis also have been developed and can significantly reduce the number of enzyme variants that need to be generated and screened.

Numerous directed evolution technologies have been developed (for reviews, see Hibbert et al., *Biomol. Eng* 22:11-19 (2005); Huisman et al., Biocatalysis in the pharmaceutical and biotechnology industries, pp. 717-742 (2007) CRC Press, R. N. Patel, Ed.); Otten et al., *Biomol. Eng* 22:1-9 (2005); and Sen et al., *Appl Biochem. Biotechnol* 143:212-223 (2007).) to be effective at creating diverse variant libraries and these methods have been successfully applied to the improvement of a wide range of properties across many enzyme classes.

Enzyme characteristics that have been improved and/or altered by directed evolution technologies include, for example, selectivity/specificity—for conversion of non-natural substrates; temperature stability—for robust high temperature processing; pH stability—for bioprocessing under lower or higher pH conditions; substrate or product tolerance—so that high product titers can be achieved; binding ($K_m$)—broadens substrate binding to include non-natural substrates; inhibition ($K_i$)—to remove inhibition by products, substrates, or key intermediates; activity (kcat)—increases enzymatic reaction rates to achieve desired flux; expression levels—increases protein yields and overall pathway flux; oxygen stability—for operation of air sensitive enzymes under aerobic conditions; and anaerobic activity—for operation of an aerobic enzyme in the absence of oxygen.

The following exemplary methods have been developed for the mutagenesis and diversification of genes to target desired properties of specific enzymes. Any of these can be used to alter/optimize activity of a decarboxylase enzyme.

EpPCR (Pritchard et al., *J. Theor. Biol.* 234:497-509 (2005).) introduces random point mutations by reducing the fidelity of DNA polymerase in PCR reactions by the addition of $Mn^{2+}$ ions, by biasing dNTP concentrations, or by other conditional variations. The five step cloning process to confine the mutagenesis to the target gene of interest involves: 1) error-prone PCR amplification of the gene of interest; 2) restriction enzyme digestion; 3) gel purification of the desired DNA fragment; 4) ligation into a vector; 5) transformation of the gene variants into a suitable host and screening of the library for improved performance. This method can generate multiple mutations in a single gene simultaneously, which can be useful. A high number of mutants can be generated by EpPCR, so a high-throughput screening assay or a selection method (especially using robotics) is useful to identify those with desirable characteristics.

Error-prone Rolling Circle Amplification (epRCA) (Fujii et al., *Nucl. Acids Res* 32:e145 (2004); and Fujii et al., *Nat. Protoc.* 1:2493-2497 (2006).) has many of the same elements as epPCR except a whole circular plasmid is used as the template and random 6-mers with exonuclease resistant thiophosphate linkages on the last 2 nucleotides are used to amplify the plasmid followed by transformation into cells in which the plasmid is re-circularized at tandem repeats. Adjusting the $Mn^{2+}$ concentration can vary the mutation rate somewhat. This technique uses a simple error-prone, single-step method to create a full copy of the plasmid with 3-4 mutations/kbp. No restriction enzyme digestion or specific primers are required. Additionally, this method is typically available as a kit.

DNA or Family Shuffling (Stemmer, W. P., *Proc Natl Acad Sci US.A.* 91:10747-10751 (1994); and Stemmer, W. P., *Nature* 370:389-391 (1994).) typically involves digestion of 2 or more variant genes with nucleases such as Dnase I or EndoV to generate a pool of random fragments that are reassembled by cycles of annealing and extension in the presence of DNA polymerase to create a library of chimeric genes. Fragments prime each other and recombination occurs when one copy primes another copy (template switch). This method can be used with >1 kbp DNA sequences. In addition to mutational recombinants created by fragment reassembly, this method introduces point mutations in the extension steps at a rate similar to error-prone PCR. The method can be used to remove deleterious random neutral mutations that might confer antigenicity.

Staggered Extension (StEP) (Zhao et al., *Nat. Biotechnol* 16:258-261 (1998).) entails template priming followed by repeated cycles of 2 step PCR with denaturation and very short duration of annealing/extension (as short as 5 sec). Growing fragments anneal to different templates and extend further, which is repeated until full-length sequences are made. Template switching means most resulting fragments have multiple parents. Combinations of low-fidelity polymerases (Taq and Mutazyme) reduce error-prone biases because of opposite mutational spectra.

In Random Priming Recombination (RPR) random sequence primers are used to generate many short DNA fragments complementary to different segments of the template. (Shao et al., *Nucleic Acids Res* 26:681-683 (1998).) Base misincorporation and mispriming via epPCR give point mutations. Short DNA fragments prime one another based on homology and are recombined and reassembled into full-length by repeated thermocycling. Removal of templates prior to this step assures low parental recombinants. This method, like most others, can be performed over multiple iterations to evolve distinct properties. This technology avoids sequence bias, is independent of gene length, and requires very little parent DNA for the application.

In Heteroduplex Recombination linearized plasmid DNA is used to form heteroduplexes that are repaired by mismatch repair. (Volkov et al., *Nucleic Acids Res* 27:e18 (1999); and Volkov et al., *Methods Enzymol.* 328:456-463 (2000).) The mismatch repair step is at least somewhat mutagenic. Heteroduplexes transform more efficiently than linear homoduplexes. This method is suitable for large genes and whole operons.

Random Chimeragenesis on Transient Templates (RA-CHITT) (Coco et al., *Nat. Biotechnol* 19:354-359 (2001).) employs Dnase I fragmentation and size fractionation of ssDNA. Homologous fragments are hybridized in the absence of polymerase to a complementary ssDNA scaffold. Any overlapping unhybridized fragment ends are trimmed down by an exonuclease. Gaps between fragments are filled in, and then ligated to give a pool of full-length diverse strands hybridized to the scaffold (that contains U to preclude amplification). The scaffold then is destroyed and is replaced by a new strand complementary to the diverse strand by PCR amplification. The method involves one strand (scaffold) that is from only one parent while the priming fragments derive from other genes; the parent scaffold is selected against. Thus, no reannealing with parental fragments occurs. Overlapping fragments are trimmed with an exonuclease. Otherwise, this is conceptually similar to DNA shuffling and StEP. Therefore, there should be no siblings, few inactives, and no unshuffled parentals. This technique has advantages in that few or no parental genes are created and many more crossovers can result relative to standard DNA shuffling.

Recombined Extension on Truncated templates (RETT) entails template switching of unidirectionally growing strands from primers in the presence of unidirectional ssDNA fragments used as a pool of templates. (Lee et al., *J. Molec. Catalysis* 26:119-129 (2003).) No DNA endonucleases are used. Unidirectional ssDNA is made by DNA polymerase with random primers or serial deletion with exonuclease. Unidirectional ssDNA are only templates and not primers. Random priming and exonucleases don't introduce sequence bias as true of enzymatic cleavage of DNA shuffling/RA-CHITT. RETT can be easier to optimize than StEP because it uses normal PCR conditions instead of very short extensions. Recombination occurs as a component of the PCR steps—no direct shuffling. This method can also be more random than StEP due to the absence of pauses.

In Degenerate Oligonucleotide Gene Shuffling (DOGS) degenerate primers are used to control recombination between molecules; (Bergquist et al., *Methods Mol. Biol.* 352:191-204 (2007); Bergquist et al., *Biomol. Eng* 22:63-72 (2005); Gibbs et al., *Gene* 271:13-20 (2001)) This can be used to control the tendency of other methods such as DNA shuffling to regenerate parental genes. This method can be combined with random mutagenesis (epPCR) of selected gene segments. This can be a good method to block the reformation of parental sequences. No endonucleases are needed. By adjusting input concentrations of segments made, one can bias towards a desired backbone. This method allows DNA shuffling from unrelated parents without restriction enzyme digests and allows a choice of random mutagenesis methods.

Incremental Truncation for the Creation of Hybrid Enzymes (ITCHY) creates a combinatorial library with 1 base pair deletions of a gene or gene fragment of interest. (Ostermeier et al., *Proc Natl Acad Sci US.A* 96:3562-3567 (1999); Ostermeier et al., *Nat. Biotechnol* 17:1205-1209 (1999).) Truncations are introduced in opposite direction on pieces of 2 different genes. These are ligated together and the fusions are cloned. This technique does not require homology between the 2 parental genes. When ITCHY is combined with DNA shuffling, the system is called SCRATCHY (see below). A major advantage of both is no need for homology between parental genes; for example, functional fusions between an *E. coli* and a human gene were created via ITCHY. When ITCHY libraries are made, all possible crossovers are captured.

Thio-Incremental Truncation for the Creation of Hybrid Enzymes (THIO-ITCHY) is almost the same as ITCHY except that phosphothioate dNTPs are used to generate truncations. (Lutz et al., *Nucleic Acids Res* 29:E16 (2001).) Relative to ITCHY, THIO-ITCHY can be easier to optimize, provide more reproducibility, and adjustability.

SCRATCHY-ITCHY combined with DNA shuffling is a combination of DNA shuffling and ITCHY; therefore, allowing multiple crossovers. (Lutz et al. 2001, *Proc Natl Acad Sci U.S.A.* 98:11248-11253 (2001).) SCRATCHY combines the best features of ITCHY and DNA shuffling. Computational predictions can be used in optimization. SCRATCHY is more effective than DNA shuffling when sequence identity is below 80%.

In Random Drift Mutagenesis (RNDM) mutations made via epPCR followed by screening/selection for those retaining usable activity. (Bergquist et al., *Biomol. Eng* 22:63-72 (2005).) Then, these are used in DOGS to generate recombinants with fusions between multiple active mutants or between active mutants and some other desirable parent. Designed to promote isolation of neutral mutations; its purpose is to screen for retained catalytic activity whether or not this activity is higher or lower than in the original gene. RNDM is usable in high throughput assays when screening is capable of detecting activity above background. RNDM has been used as a front end to DOGS in generating diversity. The technique imposes a requirement for activity prior to shuffling or other subsequent steps; neutral drift libraries are indicated to result in higher/quicker improvements in activity from smaller libraries. Though published using epPCR, this could be applied to other large-scale mutagenesis methods.

Sequence Saturation Mutagenesis (SeSaM) is a random mutagenesis method that: 1) generates pool of random length fragments using random incorporation of a phosphothioate nucleotide and cleavage; this pool is used as a template to 2) extend in the presence of "universal" bases such as inosine; 3) replication of a inosine-containing complement gives random base incorporation and, consequently, mutagenesis. (Wong et al., *Biotechnol J* 3:74-82 (2008); Wong et al., *Nucleic Acids Res* 32:e26 (2004); and Wong et al., *Anal. Biochem.* 341:187-189 (2005).) Using this technique it can be possible to generate a large library of mutants within 2-3 days using simple methods. This is very non-directed compared to mutational bias of DNA polymerases. Differences in this approach makes this technique complementary (or alternative) to epPCR.

In Synthetic Shuffling, overlapping oligonucleotides are designed to encode "all genetic diversity in targets" and allow a very high diversity for the shuffled progeny. (Ness et al., *Nat. Biotechnol* 20:1251-1255 (2002).) In this technique, one can design the fragments to be shuffled. This aids in increasing the resulting diversity of the progeny. One can design sequence/codon biases to make more distantly related sequences recombine at rates approaching more closely related sequences and it doesn't require possessing the template genes physically.

Nucleotide Exchange and Excision Technology NexT exploits a combination of dUTP incorporation followed by treatment with uracil DNA glycosylase and then piperidine to perform endpoint DNA fragmentation. (Muller et al., Nucleic Acids Res 33:e117 (2005).) The gene is reassembled using internal PCR primer extension with proofreading polymerase. The sizes for shuffling are directly controllable using varying dUPT::dTTP ratios. This is an end point reaction using simple methods for uracil incorporation and cleavage. One can use other nucleotide analogs such as 8-oxo-guanine with this method. Additionally, the technique works well with very short fragments (86 bp) and has a low error rate. Chemical cleavage of DNA means very few unshuffled clones.

In Sequence Homology-Independent Protein Recombination (SHIPREC) a linker is used to facilitate fusion between 2 distantly/unrelated genes; nuclease treatment is used to generate a range of chimeras between the two. Result is a single crossover library of these fusions. (Sieber et al., *Nat. Biotechnol* 19:456-460 (2001).) This produces a limited type of shuffling; mutagenesis is a separate process. This technique can create a library of chimeras with varying fractions of each of 2 unrelated parent genes. No homology is needed. SHIPREC was tested with a heme-binding domain of a bacterial CP450 fused to N-terminal regions of a mammalian CP450; this produced mammalian activity in a more soluble enzyme.

In Gene Site Saturation Mutagenesis (GSSM) the starting materials are a supercoiled dsDNA plasmid with insert and 2 primers degenerate at the desired site for mutations. (Kretz et al., *Methods Enzymol.* 388:3-11 (2004).) Primers carry the mutation of interest and anneal to the same sequence on opposite strands of DNA; mutation in the middle of the primer and ~20 nucleotides of correct sequence flanking on each side. The sequence in the primer is or NNK (coding) and MNN (noncoding) (N=all 4, K=G, T. M=A, C). After extension, DpnI is used to digest dam-methylated DNA to eliminate the wild-type template. This technique explores all possible amino acid substitutions at a given locus (i.e., one codon). The technique facilitates the generation of all possible replacements at one site with no nonsense codons and equal or near-equal representation of most possible alleles. It does not require prior knowledge of structure, mechanism, or domains of the target enzyme. If followed by shuffling or Gene Reassembly, this technology creates a diverse library of recombinants containing all possible combinations of single-site up-mutations. The utility of this technology combination has been demonstrated for the successful evolution of over 50 different enzymes, and also for more than one property in a given enzyme.

Combinatorial Cassette Mutagenesis (CCM) involves the use of short oligonucleotide cassettes to replace limited regions with a large number of possible amino acid sequence alterations. (Reidhaar-Olson et al., Methods Enzymol. 208: 564-586 (1991); and Reidhaar-Olson et al., Science 241:53-57 (1988).) Simultaneous substitutions at 2 or 3 sites are possible using this technique. Additionally, the method tests a large multiplicity of possible sequence changes at a limited range of sites. It has been used to explore the information content of lambda repressor DNA-binding domain.

Combinatorial Multiple Cassette Mutagenesis (CMCM) is essentially similar to CCM except it is employed as part of a larger program: 1) Use of epPCR at high mutation rate to 2) ID hot spots and hot regions and then 3) extension by CMCM to cover a defined region of protein sequence space. (Reetz et al., Angew. Chem. Int. Ed Engl. 40:3589-3591 (2001).) As with CCM, this method can test virtually all possible alterations over a target region. If used along with methods to create random mutations and shuffled genes, it provides an excellent means of generating diverse, shuffled proteins. This approach was successful in increasing, by 51-fold, the enantioselectivity of an enzyme.

In the Mutator Strains technique conditional is mutator plasmids allow increases of 20- to 4000-X in random and natural mutation frequency during selection and to block accumulation of deleterious mutations when selection is not required. (Selifonova et al., Appl Environ Microbiol 67:3645-3649 (2001).) This technology is based on a plasmid-derived mutD5 gene, which encodes a mutant subunit of DNA polymerase III. This subunit binds to endogenous DNA polymerase III and compromises the proofreading ability of polymerase III in any of the strain that harbors the plasmid. A broad-spectrum of base substitutions and frameshift mutations occur. In order for effective use, the mutator plasmid should be removed once the desired phenotype is achieved; this is accomplished through a temperature sensitive origin of replication, which allows plasmid curing at 41° C. It should be noted that mutator strains have been explored for quite some time (e.g., see Winter and coworkers, J. Mol. Biol. 260:359-3680 (1996). In this technique very high spontaneous mutation rates are observed. The conditional property minimizes non-desired background mutations. This technology could be combined with adaptive evolution to enhance mutagenesis rates and more rapidly achieve desired phenotypes.

"Look-Through Mutagenesis (LTM) is a multidimensional mutagenesis method that assesses and optimizes combinatorial mutations of selected amino acids." (Rajpal et al., Proc Natl Acad Sci USA 102:8466-8471 (2005.) Rather than saturating each site with all possible amino acid changes, a set of 9 is chosen to cover the range of amino acid R-group chemistry. Fewer changes per site allows multiple sites to be subjected to this type of mutagenesis. A >800-fold increase in binding affinity for an antibody from low nanomolar to picomolar has been achieved through this method. This is a rational approach to minimize the number of random combinations and should increase the ability to find improved traits by greatly decreasing the numbers of clones to be screened. This has been applied to antibody engineering, specifically to increase the binding affinity and/or reduce dissociation. The technique can be combined with either screens or selections.

Gene Reassembly is a DNA shuffling method that can be applied to multiple genes at one time or to creating a large library of chimeras (multiple mutations) of a single gene. (on the world-wide web at verenium.com/Pages/Technology/EnzymeTech/TechEnzyTGR.html) Typically this technology is used in combination with ultra-high-throughput screening to query the represented sequence space for desired improvements. This technique allows multiple gene recombination independent of homology. The exact number and position of cross-over events can be pre-determined using fragments designed via bioinformatic analysis. This technology leads to a very high level of diversity with virtually no parental gene reformation and a low level of inactive genes. Combined with GSSM, a large range of mutations can be tested for improved activity. The method allows "blending" and "fine tuning" of DNA shuffling, e.g. codon usage can be optimized.

In Silico Protein Design Automation PDA is an optimization algorithm that anchors the structurally defined protein backbone possessing a particular fold, and searches sequence space for amino acid substitutions that can stabilize the fold and overall protein energetics. (Hayes et al.,. Proc Natl Acad Sci U.S.A. 99:15926-15931 (2002).) This technology allows in silico structure-based entropy predictions in order to search for structural tolerance toward protein amino acid variations. Statistical mechanics is applied to calculate coupling interactions at each position—structural tolerance toward amino acid substitution is a measure of coupling. Ultimately, this technology is designed to yield desired modifications of protein properties while maintaining the integrity of structural characteristics. The method computationally assesses and allows filtering of a very large number of possible sequence variants) ($10^{50}$) Choice of sequence variants to test is related to predictions based on most favorable thermodynamics and ostensibly only stability or properties that are linked to stability can be effectively addressed with this technology. The method has been successfully used in some therapeutic proteins, especially in engineering immunoglobulins. In silico predictions avoid testing extraordinarily large numbers of potential variants. Predictions based on existing three-dimensional structures are more likely to succeed than predictions based on hypothetical structures. This technology can readily predict and allow targeted screening of multiple simultaneous mutations, something not possible with purely experimental technologies due to exponential increases in numbers.

Iterative Saturation Mutagenesis (ISM) involves 1) Use knowledge of structure/function to choose a likely site for enzyme improvement. 2) Saturation mutagenesis at chosen site using Stratagene QuikChange (or other suitable means). 3) Screen/select for desired properties. 4) With improved clone(s), start over at another site and continue repeating. (Reetz et al., Nat. Protoc. 2:891-903 (2007); and Reetz et al., Angew. Chem. Int. Ed Engl. 45:7745-7751 (2006).) This is a proven methodology assures all possible replacements at a given position are made for screening/selection.

Any of the aforementioned methods for mutagenesis can be used alone or in any combination. Additionally, any one or combination of the directed evolution methods can be used in conjunction with adaptive evolution techniques.

To generate better producers, metabolic modeling can be utilized to optimize growth conditions. Modeling can also be used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of cyclohexanone.

One computational method for identifying and designing metabolic alterations favoring biosynthesis of a desired product is the OptKnock computational framework (Burgard et al., Biotechnol. Bioeng. 84:647-657 (2003)). OptKnock is a metabolic modeling and simulation program that suggests gene deletion strategies that result in genetically stable microorganisms which overproduce the target product. Specifically, the framework examines the complete metabolic and/or biochemical network of a microorganism in order to suggest genetic manipulations that force the desired biochemical to become an obligatory byproduct of cell growth. By coupling biochemical production with cell growth through strategically placed gene deletions or other functional gene disruption, the growth selection pressures imposed on the engineered strains after long periods of time in a bioreactor lead to improvements in performance as a result of the compulsory growth-coupled biochemical production. Lastly, when gene deletions are constructed there is a negligible possibility of the designed strains reverting to their wild-type states because the genes selected by OptKnock are to be completely removed from the genome. Therefore, this computational methodology can be used to either identify alternative pathways that lead to biosynthesis of a desired product or used in connection with the non-naturally occurring microbial organisms for further optimization of biosynthesis of a desired product.

Briefly, OptKnock is a term used herein to refer to a computational method and system for modeling cellular metabolism. The OptKnock program relates to a framework of models and methods that incorporate particular constraints into flux balance analysis (FBA) models. These constraints include, for example, qualitative kinetic information, qualitative regulatory information, and/or DNA microarray experimental data. OptKnock also computes solutions to various metabolic problems by, for example, tightening the flux boundaries derived through flux balance models and subsequently probing the performance limits of metabolic networks in the presence of gene additions or deletions. OptKnock computational framework allows the construction of model formulations that enable an effective query of the performance limits of metabolic networks and provides methods for solving the resulting mixed-integer linear programming problems. The metabolic modeling and simulation methods referred to herein as OptKnock are described in, for example, U.S. publication 2002/0168654, filed Jan. 10, 2002, in International Patent No. PCT/US02/00660, filed Jan. 10, 2002, and U.S. publication 2009/0047719, filed Aug. 10, 2007.

Another computational method for identifying and designing metabolic alterations favoring biosynthetic production of a product is a metabolic modeling and simulation system termed SimPheny®. This computational method and system is described in, for example, U.S. publication 2003/0233218, filed Jun. 14, 2002, and in International Patent Application No. PCT/US03/18838, filed Jun. 13, 2003. SimPheny® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components.

These computational approaches are consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement biosynthesis of a desired compound in host microbial organisms. Such metabolic modeling and simulation methods include, for example, the computational systems exemplified above as SimPheny® and OptKnock. For illustration of the invention, some methods are described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

The methods described above will provide one set of metabolic reactions to disrupt. Elimination of each reaction within the set or metabolic modification can result in a desired product as an obligatory product during the growth phase of the organism. Because the reactions are known, a solution to the bilevel OptKnock problem also will provide the associated gene or genes encoding one or more enzymes that catalyze each reaction within the set of reactions. Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve production of a desired product are implemented in the target cell or organism by functional disruption of at least one gene encoding each metabolic reaction within the set. One particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the coupling of a product are desired or when genetic reversion is less likely to occur.

To identify additional productive solutions to the above described bilevel OptKnock problem which lead to further sets of reactions to disrupt or metabolic modifications that can result in the biosynthesis, including growth-coupled biosynthesis of a desired product, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that obligatorily couples product biosynthesis to growth. For example, if a previously identified growth-coupled metabolic modification specifies reactions 1, 2, and 3 for disruption, then the following constraint prevents the same reactions from being simultaneously considered in subsequent solutions. The integer cut method is well known in the art and can be found described in, for example, Burgard et al., *Biotechnol. Prog.* 17:791-797 (2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SimPheny®.

The methods exemplified herein allow the construction of cells and organisms that biosynthetically produce a desired product, including the obligatory coupling of production of a target biochemical product to growth of the cell or organism engineered to harbor the identified genetic alterations. Therefore, the computational methods described herein allow the identification and implementation of metabolic modifications that are identified by an in silico method selected from Opt-Knock or SimPheny®. The set of metabolic modifications can include, for example, addition of one or more biosynthetic pathway enzymes and/or functional disruption of one or more metabolic reactions including, for example, disruption by gene deletion.

As discussed above, the OptKnock methodology was developed on the premise that mutant microbial networks can be evolved towards their computationally predicted maximum-growth phenotypes when subjected to long periods of growth selection. In other words, the approach leverages an organism's ability to self-optimize under selective pressures. The OptKnock framework allows for the exhaustive enumeration of gene deletion combinations that force a coupling between biochemical production and cell growth based on network stoichiometry. The identification of optimal gene/reaction knockouts requires the solution of a bilevel optimization problem that chooses the set of active reactions such that an optimal growth solution for the resulting network overproduces the biochemical of interest (Burgard et al., *Biotechnol. Bioeng.* 84:647-657 (2003)).

An in silico stoichiometric model of *E. coli* metabolism can be employed to identify essential genes for metabolic pathways as exemplified previously and described in, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379. As disclosed herein, the OptKnock mathematical framework can be applied to pinpoint gene deletions leading to the growth-coupled production of a desired product. Further, the solution of the bilevel OptKnock problem provides only one set of deletions. To enumerate all meaningful solutions, that is, all sets of knockouts leading to growth-coupled production formation, an optimization technique, termed integer cuts, can be implemented. This entails iteratively solving the OptKnock problem with the incorporation of an additional constraint referred to as an integer cut at each iteration, as discussed above.

EXAMPLE I

Preparation of a Cyclohexanone Producing Microbial Organism Having a Pimeloyl-CoA Pathway This example describes the generation of a microbial organism capable of producing cyclohexanone from pimeloyl-CoA, as demonstrated in FIG. 1.

*Escherichia coli* is used as a target organism to engineer a cyclohexanone-producing pathway from pimeloyl-CoA as shown in FIG. 1. *E. coli* provides a good host for generating a non-naturally occurring microorganism capable of producing cyclohexanone. *E. coli* is amenable to genetic manipulation and is known to be capable of producing various products, like ethanol, acetic acid, formic acid, lactic acid, and succinic acid, effectively under anaerobic or microaerobic conditions. Moreover, pimeloyl-CoA is naturally produced in *E. coli* as an intermediate in biotin biosynthesis.

To generate an *E. coli* strain engineered to produce cyclohexanone from pimeloyl-CoA, nucleic acids encoding the enzymes utilized in the pathway of FIG. 1, described previously, are expressed in *E. coli* using well known molecular biology techniques (see, for example, Sambrook, supra, 2001; Ausubel supra, 1999; Roberts et al., supra, 1989). In particular, the syn_01653 (YP_463074.1), adc (NP_149328.1), pcaIJ (Q01103.2 and P0A102.2), and pckA (P43923.1) genes encoding the 2-ketocyclohexane-1-carboxyl-CoA hydrolase (acting on C—C bond), 2-ketocyclohexane-1-carboxylate decarboxylase, 2-ketocyclohexane-1-carboxyl-CoA transferase and phosphoenolpyruvate carboxykinase, respectively, are cloned into the pZE13 vector (Expressys, Ruelzheim, Germany), under the control of the PA1/lacO promoter. This plasmid is then transformed into a host strain containing lacI$^Q$, which allows inducible expression by addition of isopropyl-beta-D-1-thiogalactopyranoside (IPTG).

The resulting genetically engineered organism is cultured in glucose containing medium following procedures well known in the art (see, for example, Sambrook et al., supra, 2001). The expression of cyclohexanone pathway genes is corroborated using methods well known in the art for determining polypeptide expression or enzymatic activity, including for example, Northern blots, PCR amplification of mRNA and immunoblotting. Enzymatic activities of the expressed enzymes are confirmed using assays specific for the individually activities. The ability of the engineered *E. coli* strain to produce cyclohexanone is confirmed using HPLC, gas chromatography-mass spectrometry (GCMS) or liquid chromatography-mass spectrometry (LCMS).

Microbial strains engineered to have a functional cyclohexanone synthesis pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers. Strategies are also applied to improve production of cyclohexanone precursor pimeloyl-CoA, such as mutagenesis, cloning and/or overexpression of native genes involved in the early stages of pimeloyl-CoA synthesis.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379). Modeling analysis allows reliable predictions of the effects on cell growth of shifting the metabolism towards more efficient production of cyclohexanone. One modeling method is the bilevel optimization approach, OptKnock (Burgard et al., *Biotechnol. Bioengineer.* 84:647-657 (2003)), which is applied to select gene knockouts that collectively result in better production of cyclohexanone. Adaptive evolution also can be used to generate better producers of, for example, the pimeloyl-CoA intermediate or the cyclohexanone product. Adaptive evolution is performed to improve both growth and production characteristics (Fong and Palsson, *Nat. Genet.* 36:1056-1058 (2004); Alper et al., *Science* 314:1565-1568 (2006)). Based on the results, subsequent rounds of modeling, genetic engineering and adaptive evolution can be applied to the cyclohexanone producer to further increase production.

For large-scale production of cyclohexanone, the above cyclohexanone pathway-containing organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing culture vessel (e.g., flasks can be sealed with a septum and crimp-cap). Microaerobic conditions also can be utilized by providing a small hole for limited aeration. The pH of the medium is maintained at a pH of 7 by addition of an acid, such as H2SO4. The growth rate is determined by measuring optical density using a spectrophotometer (600 nm), and the glucose uptake rate by monitoring carbon source depletion over time. Byproducts such as undesirable alcohols, organic acids, and residual glucose can be quantified by HPLC (Shimadzu) with an HPX-087 column (BioRad), using a refractive index detector for glucose and alcohols, and a UV detector for organic acids, Lin et al., *Biotechnol. Bioeng.*, 775-779 (2005).

EXAMPLE II

Preparation of a Cyclohexanone Producing Microbial Organism, in which the Cyclohexanone is Derived from Acetoacetyl-CoA Via Pimeloyl-CoA This example describes the generation of a microbial organism that has been engineered to produce enhanced levels of the cyclohexanone precursor pimeloyl-CoA from acetoacetyl-CoA, shown in FIG. 2. This engineered strain is then used as a host organism and further engineered to express enzymes or proteins for producing cyclohexanone from pimeloyl-CoA, via the pathway of FIG. 1.

*Escherichia coli* is used as a target organism to engineer a cyclohexanone-producing pathway as shown in FIG. 1. *E. coli* provides a good host for generating a non-naturally occurring microorganism capable of producing cyclohexanone. *E. coli* is amenable to genetic manipulation and is known to be capable of producing various products, like ethanol, acetic acid, formic acid, lactic acid, and succinic acid, effectively under anaerobic or microaerobic conditions.

To generate an *E. coli* strain engineered to produce cyclohexanone, nucleic acids encoding the enzymes utilized in the pathways of FIG. 1 and FIG. 2, described previously, are expressed in *E. coli* using well known molecular biology techniques (see, for example, Sambrook, supra, 2001; Ausubel supra, 1999; Roberts et al., supra, 1989).

In particular, an *E. coli* strain is engineered to produce pimeloyl-CoA from acetoacetyl-CoA via the route outlined in FIG. 2. For the first stage of pathway construction, genes encoding enzymes to transform acetoacetyl-CoA to pimeloyl-CoA (FIG. 2) are assembled onto vectors. In particular, the genes pckA (P43923.1), phbB (P23238), crt (NP_349318.1), gcdH (ABM69268.1) and gcdR (ABM69269.1) encoding phosphoenolpyruvate carboxykinase, acetoacetyl-CoA reductase, 3-hydroxybutyryl-CoA dehydratase, a glutaryl-CoA dehydrogenase, and the cognate transcriptional regulator of the glutaryl-CoA dehydrogenase, respectively, are cloned into the pZE13 vector (Expressys, Ruelzheim, Germany), under the control of the PA1/lacO promoter. The genes syn_02642 (YP_462685.1), hbd (NP_349314.1), syn_01309 (YP_461962) and syn_23587 (ABC76101) encoding oxopimeloyl-CoA:glutaryl-CoA acyltransferase, 3-hydroxypimeloyl-CoA dehydrogenase, 3-hydroxypimeloyl-CoA dehydratase, and a pimeloyl-CoA dehydrogenase, respectively, are cloned into the pZA33 vector (Expressys, Ruelzheim, Germany) under the PA1/lacO promoter. Further, the syn_02637 (ABC78522.1) and syn_02636 (ABC78523.1) genes encoding alpha and beta subunits of an electron transfer flavoprotein are cloned into a third compatible plasmid, pZS23, under the PA1/lacO promoter. pZS23 is obtained by replacing the ampicillin resistance module of the pZS13 vector (Expressys, Ruelzheim, Germany) with a kanamycin resistance module by well-known molecular biology techniques. The three sets of plasmids are transformed into *E. coli* strain MG1655 to express the proteins and enzymes required for pimeloyl-CoA synthesis from acetoacetyl-CoA.

The resulting genetically engineered organism is cultured in glucose containing medium following procedures well known in the art (see, for example, Sambrook et al., supra, 2001). The expression of pimeloyl-CoA pathway genes is corroborated using methods well known in the art for determining polypeptide expression or enzymatic activity, including for example, Northern blots, PCR amplification of mRNA and immunoblotting. Enzymatic activities of the expressed enzymes are confirmed using assays specific for the individually activities. The ability of the engineered *E. coli* strain to produce pimeloyl-CoA through this pathway is confirmed using HPLC, gas chromatography-mass spectrometry (GCMS) or liquid chromatography-mass spectrometry (LCMS).

Microbial strains engineered to have a functional pimeloyl-CoA synthesis pathway from acetoacetyl-CoA are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

After successful demonstration of enhanced pimeloyl-CoA production via the activities of the exogenous enzymes, the genes encoding these enzymes are inserted into the chromosome of a wild type *E. coli* host using methods known in the art. Such methods include, for example, sequential single crossover (Gay et al., *J. Bacteriol.* 153:1424-1431 (1983)) and Red/ET methods from GeneBridges (Zhang et al., Improved RecT or RecET doing and subcloning method (2001)). Chromosomal insertion provides several advantages over a plasmid-based system, including greater stability and the ability to co-localize expression of pathway genes.

The pimeloyl-CoA-overproducing host strain is further engineered to produce cyclohexanone. To generate a cyclohexanone-producing strain, nucleic acids encoding the enzymes utilized in the pathway of FIG. 1, described previously, are expressed in the host using well known molecular biology techniques (see, for example, Sambrook, supra, 2001; Ausubel supra, 1999; Roberts et al., supra, 1989).

In particular, the syn_01653 (YP_463074.1), adc (NP_149328.1), pcaIJ (Q01103.2 and P0A102.2) genes encoding the 2-ketocyclohexane-1-carboxyl-CoA hydrolase (acting on C—C bond), 2-ketocyclohexane-1-carboxylate decarboxylase, and 2-ketocyclohexane-1-carboxyl-CoA transferase, respectively, are cloned into the pZE13 vector (Expressys, Ruelzheim, Germany), under the control of the PA1/lacO promoter. This plasmid is then transformed into a host strain containing lacI$^Q$, which allows inducible expression by addition of isopropyl-beta-D-1-thiogalactopyranoside (IPTG).

The resulting genetically engineered organism is cultured in glucose containing medium following procedures well known in the art (see, for example, Sambrook et al., supra, 2001). The expression of cyclohexanone pathway genes is corroborated using methods well known in the art for determining polypeptide expression or enzymatic activity, including for example, Northern blots, PCR amplification of mRNA and immunoblotting. Enzymatic activities of the expressed enzymes are confirmed using assays specific for the individually activities. The ability of the engineered *E. coli* strain to produce cyclohexanone through this pathway is confirmed using HPLC, gas chromatography-mass spectrometry (GCMS) or liquid chromatography-mass spectrometry (LCMS).

Microbial strains engineered to have a functional cyclohexanone synthesis pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379). Modeling analysis allows reliable predictions of the effects on cell growth of shifting the metabolism towards more efficient production of cyclohexanone. One modeling method is the bilevel optimization approach, OptKnock (Burgard et al., *Biotechnol. Bioengineer.* 84:647-657 (2003)), which is applied to select gene knockouts that collectively result in better production of cyclohexanone. Adaptive evolution also can be used to generate better producers of, for example, the pimeloyl-CoA intermediate or the cyclohexanone product. Adaptive evolution is performed to improve both growth and production characteristics (Fong and Palsson, *Nat. Genet.* 36:1056-1058 (2004); Alper et al., *Science* 314:1565-1568 (2006)). Based on the results, subsequent rounds of modeling, genetic engineering and adaptive evolution can be applied to the cyclohexanone producer to further increase production.

For large-scale production of cyclohexanone, the above cyclohexanone pathway-containing organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing culture vessel (e.g., flasks can be sealed with a septum and crimp-cap). Microaerobic conditions also can be utilized by providing a small hole for limited aeration. The pH of the medium is maintained at a pH of 7 by addition of an acid, such as H2SO4. The growth rate is determined by measuring optical density using a spectrophotometer (600 nm), and the glucose uptake rate by monitoring carbon source depletion over time. Byproducts such as undesirable alcohols, organic acids, and residual glucose can be quantified by HPLC (Shimadzu) with an HPX-087 column (BioRad), using a refractive index detector for glucose and alcohols, and a UV detector for organic acids, Lin et al., *Biotechnol. Bioeng.*, 775-779 (2005).

EXAMPLE III

Preparation of a Cyclohexanone Producing Microbial Organism, in which the Cyclohexanone is Derived from Acetoacetyl-CoA and 3-Hydroxypimeloyl-CoA is a Pathway Intermediate This example describes the generation of a microbial organism that has been engineered to produce cyclohexanone from acetoacetyl-CoA via 3-hydroxypimelate as an intermediate. 3-Hydroxypimelate is produced from acetoacetyl-CoA in five enzymatic steps, as shown in FIG. 2 (Steps 1-5). Cyclohexanone is then produced from 3-hydroxypimelate as shown in the pathway of FIG. 3 (Steps 1, 5, 6 and 7).

*Escherichia coli* is used as a target organism to engineer a cyclohexanone-producing pathway as shown in FIGS. 2 and 3. *E. coli* provides a good host for generating a non-naturally occurring microorganism capable of producing cyclohexanone. *E. coli* is amenable to genetic manipulation and is known to be capable of producing various products, like ethanol, acetic acid, formic acid, lactic acid, and succinic acid, effectively under anaerobic or microaerobic conditions.

To generate an *E. coli* strain engineered to produce cyclohexanone, nucleic acids encoding the enzymes utilized in the pathways of FIG. 2 (Steps 1-5) and FIG. 3 (Steps 1, 5, 6 and 7), described previously, are expressed in *E. coli* using well known molecular biology techniques (see, for example, Sambrook, supra, 2001; Ausubel supra, 1999; Roberts et al., supra, 1989).

To generate an *E. coli* strain for producing cyclohexanone from acetoacetyl-CoA via 3-hydroxypimeloyl-CoA, genes encoding enzymes to transform acetoacetyl-CoA to 3-hydroxypimeloyl-CoA (FIG. 2) and 3-hydroxypimeloyl-CoA to cyclohexanone (FIG. 3) are assembled onto vectors. In particular, the genes pckA (P43923.1), phbB (P23238), crt (NP_349318.1), gcdH (ABM69268.1) and gcdR (ABM69269.1) genes encoding phosphoenolpyruvate carboxykinase, acetoacetyl-CoA reductase, 3-hydroxybutyryl-CoA dehydratase, a glutaryl-CoA dehydrogenase, and the cognate transcriptional regulator of the glutaryl-CoA dehydrogenase, respectively, are cloned into the pZE13 vector (Expressys, Ruelzheim, Germany), under the control of the PA1/lacO promoter. The genes syn_02642 (YP_462685.1), hbd (NP_349314.1), band (YP_463073.1) and pcaIJ (Q01103.2 and P0A102.2) encoding oxopimeloyl-CoA:glutaryl-CoA acyltransferase, 3-hydroxypimeloyl-CoA dehydrogenase, 6-ketocyclohex-1-ene-1-carboxyl-CoA hydrolases (acting on CC bond) and 2-ketoeyclohexane-1-catboxyl-CoA transferase, respectively, are cloned into the pZA33 vector (Expressys, Ruelzheim, Germany) under the PA1/lacO promoter. Further, the genes acad1 (AAC48316.1), acad (AAA16096.1) and adc (NP_149328.1), encoding 6-ketocyclohex-1-ene-1-carboxyl-CoA reductase and 2-ketocyclohexane-1-carboxylate decarboxylase, respectively, are cloned into a third compatible plasmid, pZS23, under the PA1/lacO promoter. pZS23 is obtained by replacing the ampicillin resistance module of the pZS13 vector (Expressys, Ruelzheim, Germany) with a kanamycin resistance module by well-known molecular biology techniques. The three sets of plasmids are transformed into *E. coli* strain MG 1655 to express the proteins and enzymes required for cyclohexanone synthesis from acetoacetyl-CoA.

The resulting genetically engineered organism is cultured in glucose containing medium following procedures well known in the art (see, for example, Sambrook et al., supra, 2001). The expression of cyclohexanone pathway genes is corroborated using methods well known in the art for determining polypeptide expression or enzymatic activity, including for example, Northern blots, PCR amplification of mRNA and immunoblotting. Enzymatic activities of the expressed enzymes are confirmed using assays specific for the individually activities. The ability of the engineered *E. coli* strain to produce cyclohexanone through this pathway is confirmed using HPLC, gas chromatography-mass spectrometry (GCMS) or liquid chromatography-mass spectrometry (LCMS).

Microbial strains engineered to have a functional cyclohexanone synthesis pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379). Modeling analysis allows reliable predictions of the effects on cell growth of shifting the metabolism towards more efficient production of cyclohexanone. One modeling method is the bilevel optimization approach, OptKnock (Burgard et al., *Biotechnol. Bioengineer.* 84:647-657 (2003)), which is applied to select gene knockouts that collectively result in better production of cyclohexanone. Adaptive evolution also can be used to generate better producers of, for example, the 3-hydroxypimeloyl-CoA intermediate or the cyclohexanone product. Adaptive evolution is performed to improve both growth and production characteristics (Fong and Palsson, *Nat. Genet.* 36:1056-1058 (2004); Alper et al., *Science* 314: 1565-1568 (2006)). Based on the results, subsequent rounds of modeling, genetic engineering and adaptive evolution can be applied to the cyclohexanone producer to further increase production.

For large-scale production of cyclohexanone, the above cyclohexanone pathway-containing organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing culture vessel (e.g., flasks can be sealed with a septum and crimp-cap). Microaerobic conditions also can be utilized by providing a small hole for limited aeration. The pH of the medium is maintained at a pH of 7 by addition of an acid, such as H2SO4. The growth rate is determined by measuring optical density using a spectrophotometer (600 nm), and the glucose uptake rate by monitoring carbon source depletion over time. Byproducts such as undesirable alcohols, organic acids, and residual glucose can be quantified by HPLC (Shimadzu) with an HPX-087 column (BioRad), using a refractive index detector for glucose and alcohols, and a UV detector for organic acids, Lin et al., *Biotechnol. Bioeng.*, 775-779 (2005).

EXAMPLE IV

Preparation of a Cyclohexanone Producing Microbial Organism, in which the Cyclohexanone is Derived from Adipate Semialdehyde This example describes the generation of a microbial organism that has been engineered to produce cyclohexanone from adipate semialdehyde, as shown in FIG. 4. First, an *E. coli* host strain is engineered to overproduce the cyclohexanone precursor adipate semialdehyde, according to the teachings of U.S. patent application Ser. No. 12/413,355. The adipate semialdehyde-overproducing host is further engineered to overproduce cyclohexanone.

*Escherichia coli* is used as a target organism to engineer a cyclohexanone-producing pathway as shown in FIG. 4. *E. coli* provides a good host for generating a non-naturally occurring microorganism capable of producing cyclohexanone. *E. coli* is amenable to genetic manipulation and is known to be capable of producing various products, like ethanol, acetic acid, formic acid, lactic acid, and succinic acid, effectively under anaerobic or microaerobic conditions.

Adipate semialdehyde is not a naturally occurring metabolite in *Escherichia coli*. However, a number of biosynthetic routes for adipate biosynthesis have recently been disclosed [U.S. patent application Ser. No. 12/413,355]. In one route, termed the "reverse degradation pathway", adipate semialdehyde is produced from molar equivalents of acetyl-CoA and succinyl-CoA, joined by a beta-ketothiolase to form oxoadipyl-CoA. Oxoadipyl-CoA is then converted to adipyl-CoA in three enzymatic steps: reduction of the ketone, dehydration, and reduction of the enoyl-CoA. Once formed, adipyl-CoA is converted to adipate semialdehyde by a CoA-dependent aldehyde dehydrogenase.

To generate an *E. coli* strain engineered to produce adipate semialdehyde, nucleic acids encoding the enzymes of the reverse degradation pathway are expressed in *E. coli* using well known molecular biology techniques (see, for example, Sambrook, supra, 2001; Ausubel supra, 1999). In particular, the paaJ (NP_415915.1), paaH (NP_415913.1), maoC (NP_415905.1) and pckA (P43923.1) genes encoding a succinyl-CoA:acetyl-CoA acyl transferase, 3-hydroxyacyl-CoA dehydrogenase, 3-hydroxyadipyl-CoA dehydratase and phosphoenolpyruvate carboxykinase activities, respectively, are cloned into the pZE13 vector (Expressys, Ruelzheim, Germany) under the PA1/lacO promoter. In addition, the bcd (NP_349317.1), etfAB (349315.1 and 349316.1), and sucD (P38947.1) genes encoding 5-carboxy-2-pentenoyl-CoA reductase and adipyl-CoA aldehyde dehydrogenase activities, respectively, are cloned into the pZA33 vector (Expressys, Ruelzheim, Germany) under the PA1/lacO promoter. The two sets of plasmids are transformed into *E. coli* strain MG1655 to express the proteins and enzymes required for adipate synthesis via the reverse degradation pathway.

The resulting genetically engineered organism is cultured in glucose containing medium following procedures well known in the art (see, for example, Sambrook et al., supra, 2001). The expression of adipate semialdehyde pathway genes is corroborated using methods well known in the art for determining polypeptide expression or enzymatic activity, including for example, Northern blots, PCR amplification of mRNA and immunoblotting. Enzymatic activities of the expressed enzymes are confirmed using assays specific for the individually activities. The ability of the engineered *E. coli* strain to produce adipate semialdehyde through this pathway is confirmed using HPLC, gas chromatography-mass spectrometry (GCMS) or liquid chromatography-mass spectrometry (LCMS).

Microbial strains engineered to have a functional adipate semialdehyde synthesis pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

After successful demonstration of enhanced adipate semialdehyde production via the activities of the exogenous enzymes, the genes encoding these enzymes are inserted into the chromosome of a wild type *E. coli* host using methods known in the art. Such methods include, for example, sequential single crossover (Gay et al., supra) and Red/ET methods from GeneBridges (Zhang et al., supra). The resulting strain is then utilized in subsequent efforts to engineer a cyclohexanone-overproducing pathway.

A requirement for engineering a cyclohexanone producing organism that utilizes the adipate semialdehyde pathway is identification of a gene with adipate semialdehyde dehydratase activity, that is, catalyzing the dehydration and concurrent cyclization of adipate semialdehyde to cyclohexane-1,2-dione. This activity has been demonstrated in the ring-opening direction in cell extracts of *Azoarcus* 22Lin (Harder, J., supra), but the gene associated with this activity has not been identified to date. To identify an enzyme with adipate semialdehyde dehydratase activity, a plasmid-based library composed of fragments of the *Azoarcus* 22Lin genome is constructed. Plasmids are transformed into *E. coli* and resulting colonies are isolated, supplied with cyclohexan-1,2-dione and screened for adipate semialdehyde dehydratase activity. Strains bearing plasmids with enzyme activity are isolated and the plasmids are sequenced. The sequences are examined to identify likely protein-encoding open reading frames (ORFs). Gene candidates are BLASTed against non-redundant protein sequences to determine potential function. Promising gene candidates encoded by the plasmid(s) are isolated by PCR, cloned into new vectors, transformed into *E. coli* and tested for adipate semialdehyde dehydratase activity.

Nucleic acids encoding the enzymes utilized in the pathway of FIG. 4, described previously, are expressed in *E. coli* using well known molecular biology techniques (see, for example, Sambrook, supra, 2001; Ausubel supra, 1999; Roberts et al., supra, 1989). In particular, the ARA1 (NP_009707.1) and pddCBA (AAC98386.1, AAC98385.1 and AAC98384.1) genes encoding the cyclohexane-1,2-diol dehydrogenase and cyclohexane-1,2-diol dehydratase, respectively, are cloned into the pZE13 vector (Expressys, Ruelzheim, Germany), under the control of the PA1/lacO promoter. Further, the newly identified adipate semialdehyde dehydrogenase gene is cloned into the pZA33 vector (Expressys, Ruelzheim, Germany) under the PA1/lacO promoter. The two sets of plasmids are transformed into the adipate semialdehyde-overproducing *E. coli* host to express the proteins and enzymes required for adipate synthesis via the reverse degradation pathway.

The resulting genetically engineered organism is cultured in glucose containing medium following procedures well known in the art (see, for example, Sambrook et al., supra, 2001). The expression of cyclohexanone pathway genes is corroborated using methods well known in the art for determining polypeptide expression or enzymatic activity, including for example, Northern blots, PCR amplification of mRNA and immunoblotting. Enzymatic activities of the expressed enzymes are confirmed using assays specific for the individually activities. The ability of the engineered *E. coli* strain to produce cyclohexanone through this pathway is confirmed using HPLC, gas chromatography-mass spectrometry (GCMS) or liquid chromatography-mass spectrometry (LCMS).

Microbial strains engineered to have a functional cyclohexanone synthesis pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379). Modeling analysis allows reliable predictions of the effects on cell growth of shifting the metabolism towards more efficient production of cyclohexanone. One modeling method is the bilevel optimization approach, OptKnock (Burgard et al., *Biotechnol. Bioengineer.* 84:647-657 (2003)), which is applied to select gene knockouts that collectively result in better production of cyclohexanone. Adaptive evolution also can be used to generate better producers of for example, the cyclohexane-1,2-dione intermediate or the cyclohexanone product. Adaptive evolution is performed to improve both growth and production characteristics (Fong and Palsson, *Nat. Genet.* 36:1056-1058 (2004); Alper et al., *Science* 314: 1565-1568 (2006)). Based on the results, subsequent rounds of modeling, genetic engineering and adaptive evolution can be applied to the cyclohexanone producer to further increase production.

For large-scale production of cyclohexanone, the above cyclohexanone pathway-containing organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing culture vessel (e.g., flasks can be sealed with a septum and crimp-cap). Microaerobic conditions also can be utilized by providing a small hole for limited aeration. The pH of the medium is maintained at a pH of 7 by addition of an acid, such as H2SO4. The growth rate is determined by measuring optical density using a spectrophotometer (600 nm), and the glucose uptake rate by monitoring carbon source depletion over time. Byproducts such as undesirable alcohols, organic acids, and residual glucose can be quantified by HPLC (Shimadzu) with an HPX-087 column (BioRad), using a refractive index detector for glucose and alcohols, and a UV detector for organic acids, Lin et al., *Biotechnol. Bioeng.*, 775-779 (2005).

EXAMPLE V

Preparation of a Cyclohexanone Producing Microbial Organism, in which the Cyclohexanone is Derived from 4-Acetylbutyrate This example describes the generation of a microbial organism that has been engineered to produce cyclohexanone from 4-acetylbutyrate via 3-oxopimeloyl-CoA, as shown in FIG. 5. This example also teaches a method for engineering a strain that overproduces the pathway precursor 3-oxopimeloyl-CoA.

*Escherichia coli* is used as a target organism to engineer a cyclohexanone-producing pathway as shown in FIG. 5. *E. coli* provides a good host for generating a non-naturally occurring microorganism capable of producing cyclohexanone. *E. coli* is amenable to genetic manipulation and is known to be capable of producing various products, like ethanol, acetic acid, formic acid, lactic acid, and succinic acid, effectively under anaerobic or microaerobic conditions.

First, an *E. coli* strain is engineered to produce 3-oxopimeloyl-CoA from acetoacetyl-CoA via the route outlined in FIG. 2. For the first stage of pathway construction, genes encoding enzymes to transform acetoacetyl-CoA to 3-oxopimeloyl-CoA (FIG. 2, Steps 1-4) is assembled onto vectors. In particular, the genes phbB (P23238), crt (NP_349318.1), gcdH (ABM69268.1) and gcdR (ABM69269.1) genes encoding acetoacetyl-CoA reductase, 3-hydroxybutyryl-CoA dehydratase, a glutaryl-CoA dehydrogenase, and the cognate transcriptional regulator of the glutaryl-CoA dehydrogenase, respectively, are cloned into the pZE13 vector (Expressys, Ruelzheim, Germany), under the control of the PA1/lacO promoter. The genes pckA (P43923.1) and syn_02642 (YP_462685.1), encoding phosphoenolpyruvate carboxykinase and oxopimeloyl-CoA:glutaryl-CoA acyltransferase, respectively, are cloned into the pZA33 vector (Expressys, Ruelzheim, Germany) under the PA1/lacO promoter. The two sets of plasmids are transformed into *E. coli* strain MG1655 to express the proteins and enzymes required for 3-oxopimeloyl-CoA synthesis from acetoacetyl-CoA.

The resulting genetically engineered organism is cultured in glucose containing medium following procedures well known in the art (see, for example, Sambrook et al., supra, 2001). The expression of 3-oxopimeloyl-CoA pathway genes is corroborated using methods well known in the art for determining polypeptide expression or enzymatic activity, including for example, Northern blots, PCR amplification of mRNA and immunoblotting. Enzymatic activities of the expressed enzymes are confirmed using assays specific for the individually activities. The ability of the engineered *E. coli* strain to produce 3-oxopimeloyl-CoA through this pathway is confirmed using HPLC, gas chromatography-mass spectrometry (GCMS) or liquid chromatography-mass spectrometry (LCMS).

Microbial strains engineered to have a functional 3-oxopimeloyl-CoA synthesis pathway from acetoacetyl-CoA are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

After successful demonstration of enhanced 3-oxopimeloyl-CoA production via the activities of the exogenous enzymes, the genes encoding these enzymes are inserted into the chromosome of a wild type *E. coli* host using methods known in the art. Such methods include, for example, sequential single crossover (Gay et al., supra) and Red/ET methods from GeneBridges (Zhang et al, supra). Chromosomal insertion provides several advantages over a plasmid-based system, including greater stability and the ability to co-localize expression of pathway genes.

A requirement for engineering a cyclohexanone producing organism that utilizes the 4-acetylbutyrate pathway is identification of a gene with 4-acetylbutyrate dehydratase activity, that is, catalyzing the dehydration and concurrent cyclization of 4-acetylbutyrate to cyclohexane-1,3-dione. This activity has been demonstrated in the hydrolytic cleavage (ring-opening) direction in cell extracts of *Alicycliphilus denitrificans* (Dangel et al., (1989) supra), but the gene associated with this activity has not been identified to date. To identify an enzyme with 4-acetylbutyrate dehydratase activity, a plasmid-based library composed of fragments of the *Alicycliphilus denitrificans* genome is constructed. Plasmids are transformed into *E. coli* and resulting colonies are isolated, supplied with cyclohexan-1,3-dione and screened for 4-acetylbutyrate dehydratase activity. Strains bearing plasmids with enzyme activity are isolated and the plasmids are sequenced. The sequences are examined to identify likely protein-encoding open reading frames (ORFs). Gene candidates are BLASTed against non-redundant protein sequences to determine potential function. Promising gene candidates encoded by the plasmid(s) are isolated by PCR, cloned into new vectors, transformed into *E. coli* and tested for 4-acetylbutyrate dehydratase activity.

To generate an *E. coli* strain engineered to produce cyclohexanone from 3-oxopimeloyl-CoA, nucleic acids encoding the enzymes utilized in the pathway of FIG. 5, described previously, are expressed in *E. coli* using well known molecular biology techniques (see, for example, Sambrook, supra, 2001; Ausubel supra, 1999; Roberts et al., supra, 1989). In particular, the pcaIJ (Q01103.2 and P0A102.2), adc (NP_149328.1) and YMR226c (NP_013953.1) genes encoding the 3-oxopimeloyl-CoA transferase, 3-oxopimelate decarboxylase and 3-hydroxycyclohexanone dehydrogenase, respectively, are cloned into the pZE13 vector (Expressys, Ruelzheim, Germany), under the control of the PA1/lacO promoter. Additionally, the genes HIDH (BAD80840.1) and YML131W (AAS56318.1), encoding 2-cyclohexenone hydratase and cyclohexanone dehydrogenase, respectively, and also the newly identified 4-acetylbutyrate dehydratase gene, are cloned into the pZA33 vector (Expressys, Ruelzheim, Germany) under the PA1/lacO promoter. The two sets of plasmids are transformed into *E. coli* strain MG1655 to express the proteins and enzymes required for cyclohexanone synthesis from 3-oxopimeloyl-CoA.

The resulting genetically engineered organism is cultured in glucose containing medium following procedures well known in the art (see, for example, Sambrook et al., supra, 2001). The expression of cyclohexanone pathway genes is corroborated using methods well known in the art for determining polypeptide expression or enzymatic activity, including for example, Northern blots, PCR amplification of mRNA and immunoblotting. Enzymatic activities of the expressed enzymes are confirmed using assays specific for the individually activities. The ability of the engineered *E. coli* strain to produce cyclohexanone through this pathway is confirmed using HPLC, gas chromatography-mass spectrometry (GCMS) or liquid chromatography-mass spectrometry (LCMS).

Microbial strains engineered to have a functional cyclohexanone synthesis pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379). Modeling analysis allows reliable predictions of the effects on cell growth of shifting the metabolism towards more efficient production of cyclohexanone. One modeling method is the bilevel optimization approach, OptKnock (Burgard et al., *Biotechnol. Bioengineer.* 84:647-657 (2003)), which is applied to select gene knockouts that collectively result in better production of cyclohexanone. Adaptive evolution also can be used to generate better producers of, for example, the 4-acetylbutyrate intermediate or the cyclohexanone product. Adaptive evolution is performed to improve both growth and production characteristics (Fong and Palsson, *Nat. Genet.* 36:1056-1058 (2004); Alper et al., *Science* 314:1565-1568 (2006)). Based on the results, subsequent rounds of modeling, genetic engineering and adaptive evolution can be applied to the cyclohexanone producer to further increase production.

For large-scale production of cyclohexanone, the above cyclohexanone pathway-containing organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing culture vessel (e.g., flasks can be sealed with a septum and crimp-cap). Microaerobic conditions also can be utilized by providing a small hole for limited aeration. The pH of the medium is maintained at a pH of 7 by addition of an acid, such as H2SO4. The growth rate is determined by measuring optical density using a spectrophotometer (600 nm), and the glucose uptake rate by monitoring carbon source depletion over time. Byproducts such as undesirable alcohols, organic acids, and residual glucose can be quantified by HPLC (Shimadzu) with an HPX-087 column (BioRad), using a refractive index detector for glucose and alcohols, and a UV detector for organic acids, Lin et al., *Biotechnol. Bioeng.*, 775-779 (2005).

Throughout this application various publications have been referenced. The disclosures of these publications in their entireties, including GenBank and GI number publications, are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A non-naturally occurring microbial organism comprising exogenous nucleic acids encoding each of the following cyclohexanone pathway enzymes: a PEP carboxykinase, an adipate semialdehyde dehydratase, a cyclohexane-1,2-diol dehydrogenase, and a cyclohexane-1,2-diol dehydratase, wherein said cyclohexanone pathway enzymes are expressed in sufficient amount to produce cyclohexanone.

2. The non-naturally occurring microbial organism of claim 1, wherein at least one of said exogenous nucleic acids is a heterologous nucleic acid.

3. The non-naturally occurring microbial organism of claim 1, wherein said non-naturally occurring microbial organism is in a substantially anaerobic culture medium.

4. A method for producing cyclohexanone, comprising culturing a non-naturally occurring microbial organism comprising exogenous nucleic acids encoding each of the following cyclohexanone pathway enzymes: a PEP carboxykinase, an adipate semialdehyde dehydratase, a cyclohexane-1,2-diol dehydrogenase, and a cyclohexane-1,2-diol dehydratase, wherein said cyclohexanone pathway enzymes are expressed in a sufficient amount to produce cyclohexanone, under conditions and for a sufficient period of time to produce cyclohexanone.

5. The method of claim 4, wherein at least one of said exogenous nucleic acid is a heterologous nucleic acid.

6. The method of claim 4, wherein said non-naturally occurring microbial organism is in a substantially anaerobic culture medium.

\* \* \* \* \*